United States Patent [19]

Higashi et al.

[11] Patent Number: 5,264,151
[45] Date of Patent: Nov. 23, 1993

[54] OPTICALLY ACTIVE ESTER DERIVATIVES, PREPARATION PROCESS THEREOF, LIQUID CRYSTAL MATERIALS AND A LIGHT SWITCHING ELEMENT

[75] Inventors: Takayuki Higashi, Kishiwada; Isao Kurimoto, Toyonaka; Shoji Toda, Takarazuka; Masayoshi Minai, Moriyama; Takeshi Tani, Tsukuba; Chizu Kawakami, Tsukuba; Koichi Fujisawa, Tsukuba; Kiyoshi Imamura, Toyonaka, all of Japan

[73] Assignee: Sumitomo Chemical Company, Limited, Osaka, Japan

[21] Appl. No.: 854,585

[22] Filed: Mar. 20, 1992

Related U.S. Application Data

[62] Division of Ser. No. 398,984, Aug. 28, 1989, Pat. No. 5,124,070.

[30] Foreign Application Priority Data

| Aug. 29, 1988 | [JP] | Japan | 63-215986 |
| Aug. 30, 1988 | [JP] | Japan | 63-217189 |
| Sep. 6, 1988 | [JP] | Japan | 63-223853 |
| Sep. 29, 1988 | [JP] | Japan | 63-248671 |
| Oct. 3, 1988 | [JP] | Japan | 63-249529 |

[51] Int. Cl.$^5$ ............ C09K 19/12; C07C 39/00; C07C 69/66; C07C 67/02
[52] U.S. Cl. ............ 252/299.65; 252/299.67; 568/716; 568/774; 560/184; 560/188; 560/228; 560/254

[58] Field of Search ............ 252/299.01, 299.64, 252/299.65, 299.67; 568/716, 774; 560/129, 179, 184, 188, 226, 228, 254

[56] References Cited

U.S. PATENT DOCUMENTS

| 4,837,357 | 6/1989 | Merger et al. | 560/226 |
| 4,985,590 | 1/1991 | Minai et al. | 560/184 |

FOREIGN PATENT DOCUMENTS

| 0294852 | 6/1988 | European Pat. Off. |
| 257638 | 6/1988 | Fed. Rep. of Germany | 252/299.65 |
| 61-195187 | 8/1986 | Japan |
| 6393749 | 4/1988 | Japan | 252/299.65 |
| 2174820 | 4/1986 | United Kingdom |
| 8704426 | 7/1987 | World Int. Prop. O. |

*Primary Examiner*—Philip Tucker
*Attorney, Agent, or Firm*—Stevens, Davis, Miller & Mosher

[57] ABSTRACT

Disclosed herein are optically active phenols of formula (V) which are useful as precursors for esters used in liquid crystalline crystalline mixtures:

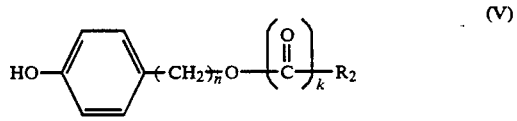

wherein $R_2$ represents an optically active alkyl or alkoxyalkyl group having 3 to 15 carbon atoms optionally substituted by halogen atoms; k represents a number of 0 or 1; n represents a number of 1 to 6.

3 Claims, No Drawings

OPTICALLY ACTIVE ESTER DERIVATIVES, PREPARATION PROCESS THEREOF, LIQUID CRYSTAL MATERIALS AND A LIGHT SWITCHING ELEMENT

This is a division of application Ser. No. 07/398,984, filed Aug. 28, 1989 now U.S. Pat. No. 5,124,070.

BACKGROUND OF THE INVENTION

1. Field of the Invention

This invention relates to optically active ester derivatives, process for producing the same, liquid crystal composition containing said derivatives as active ingredient and light switching element employing said liquid crystal composition.

The optically active ester derivatives are useful as liquid crystal compounds, especially ones showing excellent responsiveness in video display. Further, the optically active ester derivatives can be worked into liquid crystal compositions that can be utilized as a liquid crystal element for producing a light switching element.

When the term "liquid crystal compounds" is used in this specification, it means not only those derivatives which are per se capable of forming a liquid crystal phase but also the derivatives which are useful as a component to blended for a liquid crystal even if they per se cannot be observed as a liquid crystal phase.

2. Description of the Prior Art

Image display devices utilizing liquid crystal are now widely provided for practical application, and particularly, TN (twisted nematic) type display system is popularly employed for such devices.

This system has many advantages such as small power consumption and softness to the eye because of the light-receiving type display panel which itself is not luminous, but on the other hand it has the defect that the response speed in image display is low.

High-speed response is however, especially required in the recent image displays, and many efforts have been made for improving the response characteristics of the liquid crystal compounds. However, the above-mentioned twisted nematic type display system still can not stand comparison with the luminescent type display systems such as light-emitting diode, electroluminescence or plasma displays in response time.

Efforts have been continued for finding out a new display system which is capable of high-speed response while making full use of the advantages of liquid crystal displays which are light-receiving type and low in power consumption, and one result thereof has been the proposal of a display device utilizing the optical switching phenomenon of ferroelectric liquid crystal such as disclosed in Applied Physical Letter, 36, 899 (1980).

This system utilizes chiral smectic phases such as chiral smectic C phase which shows ferroelectricity (hereinafter referred to as "Sc*"). It is known that not only the Sc*, but also chiral smectic F, G, H, and I phases show ferroelectricity.

Ferroelectric liquid crystals to be used for actually used ferroelectric liquid crystal display devices are required to have many characteristics. However, at present these requirements cannot be satisfied by only one compound and ferroelectric liquid crystal compositions obtained by mixing some liquid crystal compounds or non-liquid crystal compounds must be used for satisfying them.

Such ferroelectric liquid crystal compositions may be not only those which comprise only ferroelectric liquid crystal compounds. Japanese Patent Kokai (Laid-open) No. 61-195187 has reported to obtain ferroelectric liquid crystal compositions by mixing compound or composition which forms non-chiral smectic C, F, G, H, or I phase (hereinafter referred to as "phase such as Sc") as a basic substance with one or more compounds which forms ferroelectric liquid crystal phase, thereby to make the whole a ferroelectric liquid crystal composition. Furthermore, a report has been made to mix a compound or composition which forms a phase such as Sc as a basic substance with one or more compounds which are optically active, but show no ferroelectric liquid crystal phase to make the whole a ferroelectric liquid crystal composition. (Mol. Cryst. Liq. Cryst. 89, 827 (1982)).

From the above, it is seen that a ferroelectric liquid crystal composition can be produced by mixing a basic substance with one or more compounds which is optically active irrespective of forming ferroelectric liquid crystal phase or not. However, the optically active substance is preferably capable of forming liquid crystal phase and even if it cannot form liquid crystal phase, it is preferably one having structure which resembles a liquid crystal compound, so to speak, a quasi-liquid crystal substance. However, there have not yet been found liquid crystal materials which have spontaneous polarization necessary for high speed response and have liquid crystallinity in the lower temperature region.

Under the circumstances, the present invention provides a ferroelectric liquid crystal material which has sufficient spontaneous polarization, has high speed responsiveness and besides has liquid crystallinity in the lower temperature region.

SUMMARY OF THE INVENTION

The present invention provides the optically active ester derivatives represented by the formula (I):

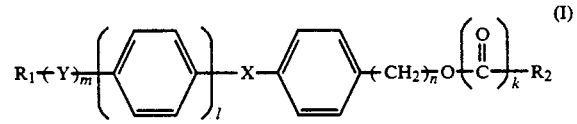

(wherein $R_1$ represents an alkyl group having 3 to 20 carbon atoms; $R_2$ represents an optically active alkyl or alkoxyalkyl group having 3 to 15 carbon atoms optionally substituted by halogen atoms; Y represents —O—, —COO— or —OCO—; X represents —COO— or —OCO—; l represents a number of 1 or 2; k and m each represents a number of 0 or 1; n represents a number of 1 to 6), preparation processes therefor, liquid crystal compositions containing such ester derivatives as active ingredient, and a light switching element using said liquid crystal compositions as liquid crystal element.

DETAILED DESCRIPTION OF THE INVENTION

The optically active ester derivatives represented by the formula (I) according to this invention can be produced by reacting phenols represented by the formula (II):

 (II)

(wherein $R_1$, Y, l and m have the meanings given above) with optically active carboxylic acid compounds represented by the formula (III):

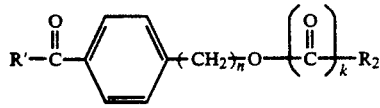 (III)

(wherein $R_2$, k and n have the meanings given above and R' represents a hydroxyl group or a halogen atom), or by reacting carboxylic acid compounds represented by the formula (IV):

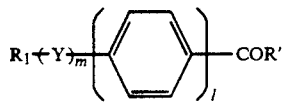 (IV)

(wherein $R_1$, Y, l and m have the meanings given above and R' represents a hydroxyl group or a halogen atom) with optically active phenols represented by the formula (V):

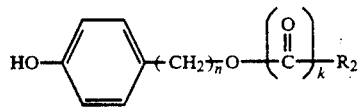 (V)

(wherein $R_2$, k and n have the meanings given above).

The optically active carboxylic acid compounds (III) containing asymmetric carbon can be produced, for instance, i) k=0 and n=1 or 2

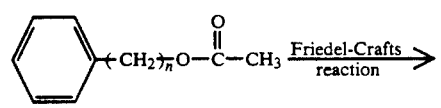 (III-a)

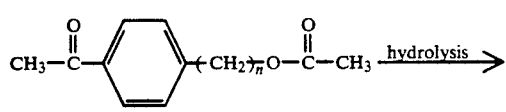

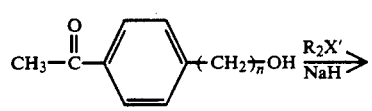

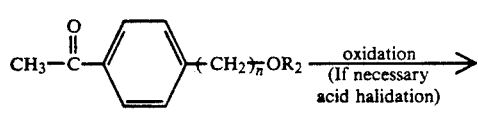

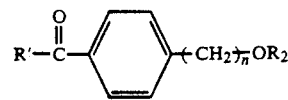

(in the above reaction formulas, X' represents a halogen atom)

ii) k=0 and n=3, 4, 5 or 6

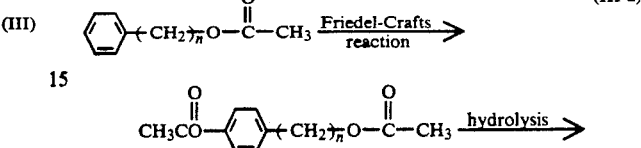 (III-a)

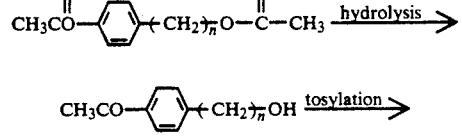

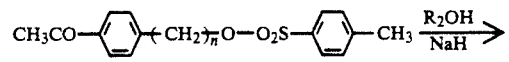

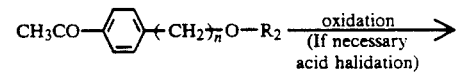

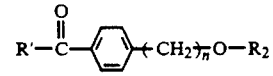

iii) k = 1

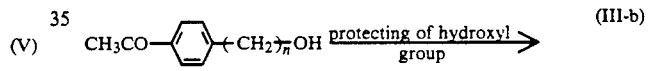 (III-b)

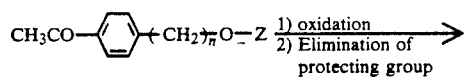

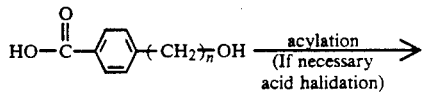

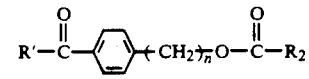

(in the above reaction formulas, Z represents a tetrahydropyranyl group, a t-butyldimethylsilyl group, a benzyl group, etc.).

Another process for producing the optically active carboxylic acid compounds (III) is as follows.

i) k=0 and n=1

It can be produced by hydrolysis of an optically active benzoate represented by the formula (IX):

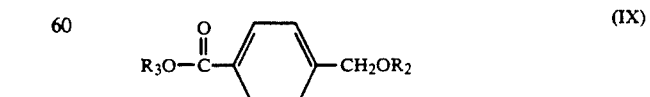 (IX)

(wherein $R_2$ has the meaning given above and $R_3$ represents a lower alkyl group).

This hydrolysis reaction is carried out in the presence of water and usually in the presence of acids or alkalis.

The acids used here include, for example, inorganic acids such as sulfuric acid, phosphoric acid and hydrochloric acid and organic acids such as toluene-sulfonic acid and methanesulfonic acid. The alkalis include, for example, organic and inorganic bases such as sodium hydroxide, potassium hydroxide, barium hydroxide, potassium carbonate, and 1,8-diazabicyclo[5,4,0]7-undecene.

Amounts of these acids or alkalis are as follows. The acids are used preferably in an amount of 0.02 to 10 mols per 1 mol of the starting compound (IX) and alkalis are used preferably in an amount of at least 1 mol and preferably 5 mols or less per 1 mol of the compound (IX), but, of course, may be used in an amount of more than 5 mols. These are normally used together with solvents and examples of such solvents are as follows.

Water and aliphatic or aromatic hydrocarbons, ethers, alcohols, ketones, amides, and halogenated hydrocarbons such as methanol, ethanol, propanol, acetone, methyl, ethyl ketone, chloroform, dichloromethane, toluene, xylene, hexane, heptane, ethyl ether, tetrahydrofuran, dioxane, dimethylformamide, and N-methylpyrrolidone which are inert to the reaction. These may be used alone or in combination of two or more. Amount thereof is not critical.

Reaction temperatures is usually $-30°$ C.$-120°$ C., preferably $-20°$ C.$-100°$ C.

Reaction time is not critical. After completion of the reaction, the optically active carboxylic acid compounds (III) are obtained in high yields by ordinary separating means such as extraction, separation of liquid phase, concentration and recrystallization and, if necessary, the products may be purified by column chromatography, etc.

The above hydrolysis reaction is more preferably carried out in the presence of an alkali because both the product carboxylic acid compound (III) and the starting compound (IX) have an ether linkage.

The optically active benzoates represented by the formula (IX) can be produced by one of the following two processes.

The first process comprises reacting a benzyl alcohol represented by the formula (X):

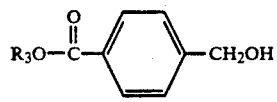

(X)

(wherein $R_3$ has the meaning given above) with an optically active alkylating agent represented by the formula (XI):

(XI)

(wherein $R_2$ has the meaning given above and $X_1$ represents a halogen atom or $-O-O_2SR'''$ in which $R'''$ represents a lower alkyl group or a phenyl group which may be substituted with a lower alkyl group).

The above alkylation reaction is carried out usually in the presence of a basic substance, which includes, for example, alkali metal hydrides such as sodium hydride and potassium hydride, alkali metals such as lithium, sodium and potassium, alkali metal alcoholates such as sodium ethylate and sodium methylate, alkali metal carbonates such as sodium carbonate and potassium carbonate, and butyl lithium.

The basic substance must be used in an amount of at least 1 equivalent to the benzyl alcohol (X) and preferably 3 equivalents or less though there is no special upper limit.

The starting compound benzyl alcohol (X) and the optically active alkylating agent (XI) may be used in various amounts depending on difficulty in availability.

That is, in general the benzyl alcohol (X) is inexpensive and easier in availability than the optically active alkylating agent (XI). Therefore, it is preferred to use the benzyl alcohol in excess amount over the amount of the optically active alkylating agent (XI) and amount of the benzyl alcohol (X) is 1-5 equivalents, especially preferably 1-3 equivalents to the optically active alkylating agent (XI).

However, in case the alkylating agent (XI) is cheaper than the benzyl alcohol (X), it is preferred to use the alkylating agent in an excess amount over the amount of the benzyl alcohol.

The alkylating agent used in the reaction includes, for example, halides such as chlorides, bromides and iodides or sulfuric esters (such as methanesulfonates, ethanesulfonates, benzenesulfonates and toluenesulfonates) which have an optically active alkyl group or alkoxyalkyl group having 3 to 15 carbon atoms optionally substituted with halogen atom as mentioned later.

The optically active alkylating agents (XI) can be produced by halogenation or esterification with sulfonic acid of optically active alcohols (XII) which will be referred to hereafter.

In case of substituent $R_2$ in the formula (XI) being an optically active alkyl group containing bromine or iodine atom, in general, sulfonic acid esters are favorably used as the alkylating agent from the point of yield.

On the other hand, in case the substituent $R_2$ being an optically active alkyl group containing fluorine or chlorine atom, bromides or iodides as alkylating agent can be used without any problems owing to difference in reactivity.

As reaction solvents, there may be used those which are inert to the reaction, for example, aliphatic or aromatic hydrocarbons, ethers, and halogenated hydrocarbons such as tetrahydrofuran, ethyl ether, acetone, methyl ethyl ketone, toluene, benzene, chlorobenzene, dimethylformamide, and hexane. These are used alone or in combination and amount thereof is not critical.

It is also possible to use polar solvents such as dimethylsulfoxide, hexamethylphosphoryl amide, and N-methylpyrrolidone.

Reaction temperature is usually $-50°$ C. to $120°$ C., preferably $-30°$ C. to $100°$ C.

The second process comprises reacting an optically active alcohol represented by the formula (XII):

(XII)

(wherein $R_2$ has the meaning given above) with a benzoic acid ester derivative represented by the formula (XIII):

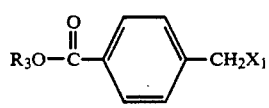

(XIII)

(wherein $R_3$ and $X_1$ have the meanings given above).

The above benzoic acid ester derivative (XIII) can be produced by halogenation of benzyl alcohol represented by the formula (X) with phosphorus tribromide or esterification of the benzyl alcohol (X) with methanesulfonyl chloride or toluenesulfonyl chloride.

With reference to the optically active alcohols (XII), commercially available products can be used for some of them, but, if necessary, they can be easily obtained by asymmetric reduction of corresponding ketones with asymmetric metal catalyst, microorganism, or enzyme.

Further, some of them can be derived from the following optically active amino acids and optically active oxyacids which occur in nature or the obtained by resolution.

Valine, leucine, isoleucine, phenylalanine, threonine, allothreonine, homoserine, alloisoleucine, tert-leucine, 2-aminobutyric acid, norvaline, norleucine, ornithine, lysine, hydroxylsine, phenylglycine, aspartic acid, glutamic acid, mandelic acid, tropic acid, 3-hydroxybutyric acid, malic acid, tartaric acid, isopropylmalic acid, etc.

The reaction conditions for alkylation in the first process explained above as they are can be employed for the reaction of the optically active alcohol (XII) with the benzoic acid ester derivative (XIII).

Regarding the amounts of the optically active alcohol (XII) and the benzoic acid ester derivative (XIII), it is generally, preferred to use the derivative (XIII) in an excess amount over the amount the alcohol (XII) because the former is cheaper and easier in availability than the latter. Amount of the derivative (XIII) is 1 to 5 equivalents, especially preferably 1-3 equivalents to the alcohol (XII).

The substituent $R_2$ of the optically active alcohol (XII) includes optically active alkyl or alkoxyalkyl group exemplified later.

ii) k=0 and n=2, 3, 4, 5 or 6

The optically active carboxylic acid compounds (III) can be produced by oxidizing an optically active acetophenone represented by the formula (VI):

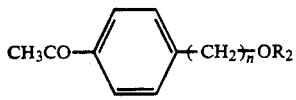

(VI)

(wherein $R_2$ has the meaning given above) with an oxidizing agent.

As the oxidizing agent used in the above reaction, there may be used any of those which oxidize an acetyl group to produce a carboxylic acid and there is no special limitation. Such oxidizing agents include, for example, potassium bichromate, sodium bichromate, potassium permanganate, sodium permanganate, potassium hydrochlorite, sodium hypochlorite, potassium hypobromite, and sodium hypobromite.

Amount of the oxidizing agent is at least 1 equivalent to the optically active acetophenone (VI) and preferably is 10 equivalents or less though there is no special limitation in upper limit.

Solvents which are normally inert to oxidation reaction are used for this reaction and examples of such solvents are water, dioxane, tetrahydrofuran and N-methylpyrrolidone.

Reaction temperature is usually −20° C. to 130° C., preferably −10° C. to 100° C.

After completion of the reaction, the optically active carboxylic acid compound (III) can be obtained in high yields by usual separating means such as filtration, acidification, extraction, separation of liquid phase, and concentration and, if necessary, this etc.

The optically active acetophenone (VI) can be produced by reacting an alkanol compound represented by the formula (XV):

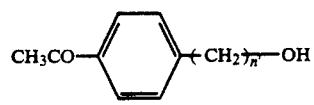

(XV)

(wherein n' represents a number of 2 to 6) with the above-mentioned optically active alkylating agent represented by the formula (XI).

Conditions for this reaction are similar to those for the aforementioned reaction of benzyl alcohol (X) and alkylating agent (XI).

The alkanol compound represented by the formula (XV) can be produced by hydrolysis of a lower alkanoic acid ester represented by the formula (XVI):

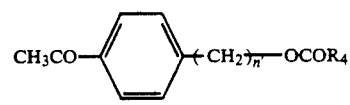

(XVI)

(wherein $R_4$ represents a lower alkyl group; n' has the meaning given above).

The conditions for the aforementioned hydrolysis of the optically active benzoic acid ester (IX) can be applied to this reaction.

The lower alkanoic acid ester represented by the formula (XVI) can be produced by acetylation of a benzene compound represented by the formula (XVII):

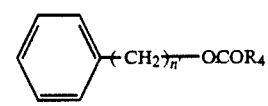

(XVII)

(wherein $R_4$ and n' have the meaning given above).

The ordinary Friedel-Crafts reaction is applied to this acetylation.

Acetic acid derivatives used for the acetylation include, for example, acetic acid, acetyl chloride and acetyl bromide. Amount of the acetic acid derivative used is at least 1 mol per 1 mol of the benzene compound (XVII) and preferably is 3 mols or less per 1 mol of the benzene compound. Catalysts used for the acetylation are those which are used for ordinary Friedel-Crafts reaction and examples thereof are aluminum chloride, aluminum bromide, zinc chloride, zinc bromide, titanium tetrachloride, polyphosphoric acid and boron trifluoride. These are used in an amount of 0.3 to 3 mols per 1 mol of benzene compound (XVII).

Reaction temperature is usually −30° C. to 150° C., preferably −10° C. to 100° C.

Reaction time is not critical.

From the thus obtained reaction mixture, the lower alkanoic acid ester represented by the formula (XVI) can be obtained in high yields by operations such as separation of liquid phase, concentration, distillation and recrystallization.

The above-mentioned optically active carboxylic acid compound (III) include, for example, 4-(alkoxymethyl)benzoic acid, 4-(2-alkoxyethyl)benzoic acid, 4-(3-alkoxypropyl)benzoic acid, 4-(4-alkoxybutyl)benzoic acid, 4-(5-alkoxypentyl)benzoic acid, 4-(6-alkoxyhexyl)benzoic acid, 4-(alkoxyalkoxymethyl)benzoic acid, 4-(2-alkoxyalkoxyethyl)benzoic acid, 4-(alkanoyloxymethyl)benzoic acid, 4-(2-alkanoyloxyethyl)benzoic acid, 4-alkoxyalkanoyloxymethyl)benzoic acid, 4-(2-alkoxyalkanoyloxyethyl)benzoic acid, 4-(3-alkoxyalkoxypropyl)benzoic acid, 4-(4-alkoxyalkoxybutyl)benzoic acid, 4-(5-alkoxyalkoxypentyl)benzoic acid, 4-(6-alkoxyalkoxyhexyl)benzoic acid, 4-(3-alkanoyloxypropyl)benzoic acid, 4-(4-alkanoyloxybutyl)benzoic acid, 4-(5-alkanoyloxypentyl)benzoic acid, 4-(6-alkanoyloxyhexyl)benzoic acid, 4-(3-alkoxyalkanoyloxypropyl)benzoic acid, 4-(4-alkoxyalkanoyloxybutyl)benzoic acid, 4-(5-alkoxyalkanoyloxypentyl)benzoic acid, and 4-(6-alkoxyalkanoyloxyhexyl)benzoic acid.

The above alkyl, alkoxyalkoxy, alkanoyloxy or alkoxyalkanoyloxy corresponds to

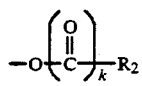

in the formula (III) and the substituent $R_2$ is an optically active alkyl or alkoxyalkyl group having an asymmetric carbon and having 3 to 15 carbon atoms which may be substituted with a halogen atom.

In case of k=0, specific examples of the above alkyl group and alkoxyalkyl group are 1-methylpropyl, 1-methylbutyl, 2-methylbutyl, 1,2-dimethylbutyl, 1,3-dimethylbutyl, 2,3-dimethylbutyl, 2,3,3-trimethylbutyl, 1,2,2-trimethylbutyl, 2-methylpentyl, 1-methylpentyl, 3-methylpentyl, 1,2-dimethylpentyl, 2,3-dimethylpentyl, 2,4-dimethylpentyl, 1,2,2,3-tetramethylpentyl, 2,3,3,4-tetramethylpentyl, 1-methylhexyl, 2-methylhexyl, 3-methylhexyl, 4-methylhexyl, 1,2-dimethylhexyl, 1,4-dimethylhexyl, 2,5-dimethylhexyl, 1-methylheptyl, 2-methylheptyl, 5-methylheptyl, 1,3-dimethylheptyl, 2-methyloctyl, 6-methyloctyl, 1,4-dimethyloctyl, 1-methylnonyl, 3-methylnonyl, 5-methylnonyl, 7-methylnonyl, 1,2-dimethylnonyl, 1-methyldecyl, 3-methyldecyl, 7-methyldecyl, 8-methyldecyl, 1-methylundecyl, 9-methylundecyl, 1-methyldodecyl, 10-methyldodecyl, methoxyethyl, methoxypropyl, methoxybutyl, methoxypentyl, methoxyhexyl, methoxyheptyl, methoxyoctyl, methoxynonyl, methoxydecyl, methoxyethyl, ethoxypropyl, ethoxybutyl, ethoxypentyl, ethoxyhexyl, ethoxyheptyl, ethoxyoctyl, ethoxynonyl, ethoxydecyl, propoxyethyl, propoxypropyl, propoxybutyl, propoxypentyl, propoxyhexyl, propoxyheptyl, propoxyoctyl, propoxynonyl, propoxydecyl, butoxyethyl, butoxypropyl, butoxybutyl, butoxypentyl, butoxyhexyl, butoxyheptyl, butoxyoctyl, butoxynonyl, butoxydecyl, pentyloxyethyl, pentyloxypropyl, pentyloxybutyl, pentyloxypentyl, pentyloxyhexyl, pentyloxyoctyl, pentyloxydecyl, hexyloxyethyl, hexyloxypropyl, hexyloxybutyl, hexyloxypentyl, hexyloxyhexyl, hexyloxyoctyl, heptyloxyethyl, heptyloxypropyl, heptyloxybutyl, heptyloxypentyl, octyloxyethyl, octyloxypropyl, decyloxyethyl, decyloxypropyl, 2-trihalomethylpentyl, 2-trihalomethylhexyl, 2-trihalomethylheptyl, 2-halopropyl, 3-halo-2-methylpropyl, 2,3-dihalopropyl, 2-halobutyl, 3-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 2-haloheptyl and 2-halooctyl (wherein "halo" indicates fluorine, chlorine, bromine or iodine).

In addition to the above substituents, when k is 1, there are recited 1-halopropyl, 1-halobutyl, 1-halopentyl, 1-halohexyl, 1-haloheptyl, 1-halooctyl, 1-halo-2-methylpropyl, 1-halo-2-methylbutyl, 1-halo-2-methylpentyl, 1-halo-2-methylhexyl, 1-halo-2-methylheptyl, 1-halo-2-methyloctyl and the like.

The optically active phenols (V) containing asymmetric carbon can be produced, for instance,
 i) k=0

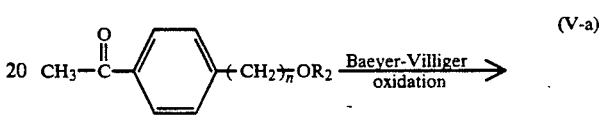

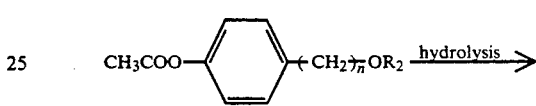

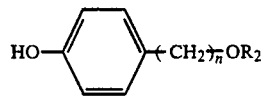

ii) k=1

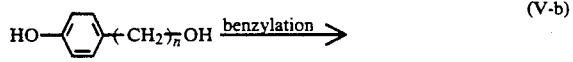

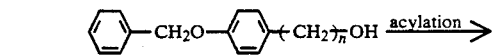

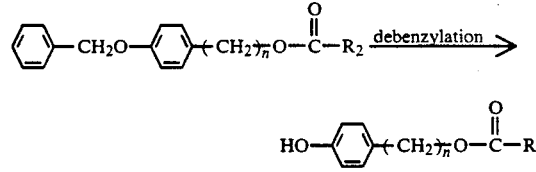

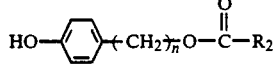

As such optically active phenols (V), mention may be made of, for example, 4-(alkoxymethyl)phenol, 4-(2-alkoxyethyl)phenol, 4-(3-alkoxypropyl)phenol, 4-(4-alkoxybutyl)phenol, 4-(5-alkoxypentyl)phenol, 4-(6-alkoxyhexyl)phenol, 4-(alkoxyalkoxymethyl)phenol, 4-(2-alkoxyalkoxyethyl)phenol, 4-(alkanoyloxymethyl)phenol, 4-(2-alkanoyloxyethyl)phenol, 4-(alkoxyalkanoyloxymethyl)phenol, 4-(2-alkoxyalkanoyloxyethyl)phenol, 4-(3-alkoxyalkoxypropyl)phenol, 4-(4-alkoxyalkoxybutyl)phenol, 4-(5-alkoxyalkoxypentyl)phenol, 4-(6-alkoxyalkoxyhexyl)phenol, 4-(3-alkanoyloxypropyl)phenol, 4-(4-alkanoyloxybutyl)phenol, 4-(5-alkanoyloxypentyl)phenol, 4-(6-alkanoyloxyhexyl)phenol, 4-(3-alkoxyalkanoyloxypropyl)phenol, 4-(4-alkoxyalkanoyloxybutyl)phenol, 4-(5-alkoxyalkanoyloxypentyl)phenol, and 4-(6-alkoxyalkanoyloxyhexyl)phenol. These may also be used as metal phenolate or tosylate.

The above alkoxy, alkoxyalkoxy, alkanoyloxy or alkoxyalkanoyloxy corresponds to

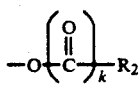

in the formula (V) and the substituent $R_2$ includes those which are exemplified above as $R_2$ in the formula (III).

Production of the optically active phenols (V) will be explained in detail.

i) $k=0$

They can be produced by hydrolysis of an optically active acetyloxybenzene compound represented by the formula (VIII):

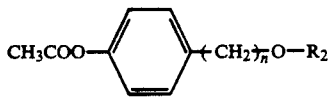

(VIII)

(wherein $R_2$ and n have the meanings given above).

The same conditions as used for hydrolysis of the optically active benzoic acid esters (IX) mentioned above can be applied to this reaction.

The optically active acetyloxybenzene compounds represented by the formula (VIII) can be produced by Baeyer-Villiger oxidation of the above-mentioned optically active acetophenone represented by the formula (VI) with a peracid.

The peracid includes, for example, peracetic acid, performic acid, m-chloroperbenzoic acid, and perbenzoic acid. These peracids can be produced, for example, from a corresponding acid and hydrogen peroxide. The Bayer-Villiger oxidation can also be conducted while a peracid is produced in the reaction system.

Amount of the peracid is ordinarily at least 1 equivalent to the optically active acetophenone represented by the formula (VI) and is preferably 5 equivalents or less though there is no special limitation in upper limit.

As solvents used in this reaction, normally those which are inert to the oxidation reaction are used and examples thereof are water and ethers, ketones, esters, halogenated hydrocarbons and aromatic or aliphatic hydrocarbons such as dioxane, tetrahydrofuran, N-methylpyrrolidone, di-n-butyl ether, ether, ethyl acetate, n-propyl acetate, dichloromethane, dichloroethane, chloroform, chlorobenzene, benzene, toluene, xylene, hexane, and cyclohexane. These may be used singly or in combination.

Reaction temperature is usually $-10°$ C. to $100°$ C., preferably $0°$ C. to $90°$ C.

ii) $k=1$

The optically active phenols can be produced by carrying out reaction of an optically active benzyloxyphenyl compound represented by the formula (VII):

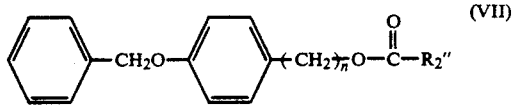

(VII)

(wherein $R_2$ and n have the meanings given above) in a solvent in the presence of a hydrogenation catalyst and hydrogen gas.

As the hydrogenation catalyst, mentioned may be made of, for example, platinum based catalysts such as $PtO_2$ and Pt-C, palladium based catalysts such as Pd-C, Pd-BaSO$_4$, and palladium black, rhodium based catalysts such as Rh-C and Rh-Al$_2$O$_3$, ruthenium based catalysts such as RuO$_2$ and Ru-C and nickel based catalysts such as Raney nickel. Preferred are palladium based catalysts.

The hydrogenation catalyst is used generally in an amount of 0.01 to 100% by weight, preferably 0.1 to 50% by weight of the optically active benzyloxyphenyl compound represented by the formula (VII).

As examples of the solvent, mention may be made of alcohols such as methanol and ethanol, ethers such as dioxane and tetrahydrofuran, aromatic hydrocarbons such as benzene and toluene, aliphatic hydrocarbons such as n-hexane and cyclohexane, esters such as ethyl acetate, amides such as dimethylformamide, fatty acids such as acetic acid, and water. These may be used singly or in combination. These may be used singly or in combination. Hydrogen pressure is usually 1 to 200 atm.

The reaction is carried out usually at 0° to 200° C., more preferably 20° to 180° C. Reaction time varies depending on kind of hydrogenation catalyst, reaction temperature and hydrogen pressure and is not critical, but end point of the reaction is normally determined by disappearance of the benzyloxyphenyl compound (VII) from the reaction system or termination of hydrogen absorption.

Separation of the optically active phenol represented by the formula (V) from the reaction mixture is carried out by usual aftertreatment such as filtration, concentration, recrystallization, distillation and column chromatography.

The optically active benzyloxyphenyl compound represented by the formula (VII) can be produced by reacting a phenylalkyl alcohol represented by the formula (XVIII):

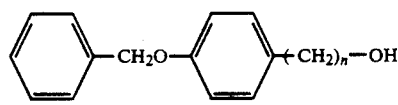

(XVIII)

(wherein n has the meaning given above) with an optically active carboxylic acid represented by the formula (XIX):

R$_2$COOH    (XIX)

(wherein R$_2$ represents an optically active alkyl or alkoxyalkyl group which may be substituted with a halogen atom and which has 3 to 15 carbon atoms) or a derivative thereof in the presence of a catalyst or a condensing agent.

Examples of the phenylalkyl alcohols (XVIII) are as follows:
1-benzyloxy-4-hydromethylbenzene,
1-benzyloxy-4-(2-hydroxyethyl)benzene,
1-benzyloxy-4-(3-hydroxypropyl)benzene,
1-benzyloxy-4-(4-hydroxybutyl)benzene,
1-benzyloxy-4-(5-hydroxypentyl)benzene, and
1-benzyloxy-4-(6-hydroxyhexyl)benzene.

These phenylalkyl alcohols (XVIII) can be produced by reacting a corresponding 4-hydroxyalkylphenol with benzyl chloride, for example, in the presence of sodium hydride.

In the reaction of the phenylalkyl alcohol (XVIII) with the optically active aliphatic carboxylic acid or a derivative thereof, a free carboxylic acid, acid anhydride thereof or an acid halide such as acid chloride or acid bromide is used.

Some of the optically active aliphatic carboxylic acids (XIX) can be obtained by oxidation of corresponding alcohols or reductive deamination of amino acid and some of others can be derived from the following optically active amino acids or optically active oxyacids which occur in nature or are obtained by resolution.

Alanine, valine, leucine, isoleucine, phenylalanine, serine, threonine, allothreonine, homoserine, alloisoleucine, tert-leucine, 2-aminobutyric acid, norvaline, norleucine, ornithine, lysine, hydroxylysine, phenylglycine, trifluoroalanine, aspartic acid, glutamic acid, lactic acid, mandelic acid, tropic acid, 3-hydroxybutyric acid, malic acid, tartaric acid and isopropylmalic acid.

Conditions for the reaction of phenylalkyl alcohols (XVIII) with the optically active aliphatic acids or derivatives thereof are similar to those for the reaction of carboxylic acid compounds (IV) and the optically active phenols (V).

The phenols (II) and carboxylic acid compounds (IV) used as another starting material in said reactions are mostly the known compounds and can be produced according to the methods disclosed in the literature.

Examples of such phenols (II) and carboxylic acid compounds (IV) are as follows: 4-alkoxyphenol, 4-alkylphenol, 4'-alkoxy-4-hydroxybiphenyl, 4'-alkyl-4-hydroxybiphenyl, 4-alkoxycarbonylphenol, 4-alkylcarbonyloxyphenol, 4'-alkoxycarbonyl-4-hydroxybiphenyl, 4'-alkylcarbonyloxy-4-hydroxybiphenyl, 4-alkoxybenzoic acid, 4-alkylbenzoic acid, 4'-alkoxy-4-biphenylcarboxylic acid, 4'-alkyl-4-biphenylcarboxylic acid, 4-alkoxycarbonylbenzoic acid, 4-alkylcarbonyloxybenzoic acid, 4'-alkoxycarbonyl-4-biphenylcarboxylic acid, and 4'-alkylcarbonyloxy-4-biphenylcarboxylic acid.

The above alkyl and alkoxy have a straight chain alkyl group having 3 to 20 carbon atoms. Typical examples of the alkyl groups are as follows.

Propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

The phenols (II) can be reacted with the optically active carboxylic acids (III) as metal phenolates.

Furthermore, carboxylic acids (IV) can also be utilized as acid halides, namely, acid chloride, acid bromide, etc.

An ordinary esterification method can be applied for the reaction of optically active phenols (V) and carboxylic acid compounds (IV) or the reaction of optically active carboxylic acids (III) and phenols (II), and such reaction can be carried out in the presence or absence of a solvent by using a catalyst.

In case of using a solvent in these reactions, such solvent is selected from those which are inert to the reaction, such as aliphatic or aromatic hydrocarbons, ethers, halogenated hydrocarbons and the like, the typical examples thereof being tetrahydrofuran, ethyl ether, acetone, methyl ethyl ketone, toluene, benzene, chlorobenzene, dichloromethane, dichloroethane, chloroform, carbon tetrachloride, dimethylformamide, hexane and the like. These solvents may be used either singly or in combination. No specific limitations are imposed on the amount of such solvent(s) used.

Since the optically active phenols (V) and the optically active carboxylic acids (III) used in the reaction are expensive, it is advisable to use the other starting material, viz. carboxylic acid compounds (IV) or phenols (II), in an excess amount, usually 1 to 4 equivalents, preferably 1 to 2 equivalents to the optically active phenols (V) or optically active carboxylic acids (III).

As the catalyst, there can be used organic or inorganic basic materials such as dimethylaminopyridine, triethylamine, tri-n-butylamine, pyridine, picoline, collidine, imidazole, sodium carbonate, sodium methylate, potassium hydrogencarbonate and the like.

Organic or inorganic acids such as toluenesulfonic acid, methanesulfonic acid, sulfuric acid, etc., are also usable as catalyst.

It is also possible to use a condensing reagent in the case of dehydration for the free carboxylic acids and phenols.

As the condensing reagent, there can be used organic materials such as N,N'-dicyclohexyl carbodiimide, N-cyclohexyl-N'-(4-diethylamino)-cyclohexyl carbodiimide, carbodiimide, imidazoylimidazole and the like.

If necessary there can be used organic amines such as 4-pyrollidinopyridine, pyridine, triethylamine and the like.

The amount of a condensing reagent is usually 1 to 1.2 equivalents to the carboxylic acid.

The amount of the organic amine is usually 0.01 to 0.2 equivalent to a condensing reagent.

The amount of the catalyst to be used is not specified as it varies depending on the type of the starting materials used, their combination with the catalyst used and other factors, but in case of using an acid halide as a starting material, a basic material is used as catalyst in an amount not less than one equivalent to said acid halide.

The reaction temperature is usually $-30°$ to $100°$ C. The reaction time is not subject to any specific limitations.

After the reaction has been completed, the reaction product is subjected to the ordinary separating means such as extraction, separation of liquid phase, concentration, etc., to isolate the objective optically active ester derivatives of the formula (I). If necessary, the product may be purified by column chromatography, recrystallization or other means.

The optically active ester derivative to be thus obtained are actually exemplified as follows:

In the following examples, "$(C_{3-15})$" and "$(C_{3-20})$" mean "having 3-15 carbon atoms" and "having 3-20 carbon atoms", respectively.

4-[alkyl($C_{3-15}$)oxymethyl]benzoic acid 4-[alkyl($C_{3-20}$)oxy]phenyl ester, 4-[2-alkyl($C_{3-15}$)oxymethyl]benzoic acid 4-[alkyl($C_{3-20}$)oxy]phenyl ester, 4-[alkyl($C_{3-15}$)oxymethyl]benzoic acid 4-[alkyl($C_{3-20}$)]phenyl ester, 4-[2-alkyl($C_{3-15}$)oxyethyl]benzoic acid 4-[alkyl($C_{3-20}$)]phenyl ester, 4-[alkyl($C_{3-15}$)oxymethyl]benzoic acid 4'-[alkyl($C_{3-20}$)oxy]biphenyl ester, 4-[2-alkyl($C_{3-15}$)oxyethyl]benzoic acid 4'-[alkyl($C_{3-20}$)oxy]biphenylyl ester, 4-[alkyl($C_{3-15}$)oxymethyl]benzoic acid 4'-[alkyl($C_{3-20}$)]biphenylyl ester, 4-[2-alkyl($C_{3-15}$)oxyethyl]benzoic acid 4'-[alkyl($C_{3-20}$)]biphenylyl ester, 4-[alkyl($C_{3-15}$)oxymethyl]benzoic acid 4-[alkyl($C_{3-20}$)oxycarbonyl]phenyl ester, 4-[2-alkyl($C_{3-15}$)oxyethyl]benzoic acid 4-[alkyl($C_{3-20}$)oxycarbonyl]phenyl ester,
4-[alkyl($C_{3-15}$)oxymethyl]benzoic acid 4'-[alkyl($C_{3-20}$)oxycarbonyl]biphenylyl ester,
4-[2-alkyl($C_{3-15}$)oxyethyl]benzoic acid 4'-[alkyl($C_{3-20}$)oxycarbonyl]biphenylyl ester,
4-[alkyl($C_{3-15}$)oxymethyl]benzoic acid 4-alkyl($C_{3-20}$)carbonyloxy]phenyl ester,
4-[2-alkyl($C_{3-15}$)oxyethyl]benzoic acid 4-[alkyl($C_{3-20}$)carbonyloxy]phenyl ester,
4-[alkyl($C_{3-15}$)oxymethyl]benzoic acid 4'-[alkyl($C_{3-20}$)carbonyloxy]biphenylyl ester,
4-[alkyl($C_{3-15}$)oxyethyl]benzoic acid 4'-[alkyl($C_{3-20}$)carbonyloxy]biphenylyl ester,
4-[3-alkyl($C_{3-15}$)oxypropyl]benzoic acid 4-[alkyl($C_{3-20}$)oxy]phenyl ester,
4-[alkyl($C_{3-15}$)oxybutyl]benzoic acid 4-[alkyl($C_{3-20}$)oxy]phenyl ester
4-[5-alkyl($C_{3-15}$)oxypentyl]benzoic acid 4-[alkyl($C_{3-20}$)oxy]phenyl ester,
4-[6-alkyl($C_{3-15}$)oxyhexyl]benzoic acid 4-[alkyl($C_{3-20}$)oxy]phenyl ester,
4-[3-alkyl($C_{3-15}$)oxypropyl]benzoic acid 4-[alkyl($C_{3-20}$)]phenyl ester,
4-[4-alkyl($C_{3-15}$)oxybutyl]benzoic acid 4-[alkyl($C_{3-20}$)]phenyl ester,
4-[5-alkyl($C_{3-15}$)oxypentyl]benzoic acid 4-[alkyl($C_{3-20}$)]phenyl ester,
4-[6-alkyl($C_{3-15}$)oxyhexyl]benzoic acid 4-[alkyl($C_{3-20}$)]phenyl ester,
4-[3-alkyl($C_{3-15}$)oxypropyl]benzoic acid 4'-[alkyl($C_{3-20}$)oxy]biphenylyl ester,
4-[4-alkyl($C_{3-15}$)oxybutyl]benzoic acid 4'-[alkyl($C_{3-20}$)oxy]biphenylyl ester,
4-[5-alkyl($C_{3-15}$)oxypentyl]benzoic acid 4'-[alkyl($C_{3-20}$)oxy]biphenylyl ester,
4-[6-alkyl($C_{3-15}$)oxyhexyl]benzoic acid 4'-[alkyl($C_{3-20}$)oxy]biphenylyl ester,
4-[3-alkyl($C_{3-15}$)oxypropyl]benzoic acid 4'-[alkyl($C_{3-20}$)]biphenylyl ester,
4-[4-alkyl($C_{3-15}$)oxybutyl]benzoic acid 4'-[alkyl($C_{3-20}$)]biphenylyl ester,
4-[5-alkyl($C_{3-15}$)oxypentyl]benzoic acid 4'-[alkyl($C_{3-20}$)]diphenylyl ester,
4-[6-alkyl($C_{3-15}$)oxyhexyl]benzoic acid 4'-[alkyl($C_{3-20}$)]biphenylyl ester,
4-[3-alkyl($C_{3-15}$)oxypropyl]phenyl 4-[alkyl($C_{3-20}$)]phenylcarboxylate,
4-[4-alkyl($C_{3-15}$)oxybutyl]phenyl 4-[alkyl($C_{3-20}$)]phenylcarboxylate,
4-[5-alkyl($C_{3-15}$)oxypentyl]phenyl 4-[alkyl($C_{3-20}$)]phenylcarboxyliate,
4-[6-alkyl($C_{3-15}$)oxyhexyl]phenyl 4-[alkyl($C_{3-20}$)]phenylcarboxylate,
4-[3-alkyl($C_{3-15}$)oxypropyl]phenyl 4-[alkyl($C_{3-20}$)oxy]phenylcarboxylate,
4-[4-alkyl($C_{3-15}$)oxybutyl]phenyl 4-[alkyl($C_{3-20}$)oxy]phenylcarboxylate,
4-[5-alkyl($C_{3-15}$)oxypentyl]phenyl 4-[alkyl($C_{3-20}$)oxy]phenylcarboxylate,
4-[6-alkyl($C_{3-15}$)oxyhexyl]phenyl 4-[alkyl($C_{3-20}$)oxy]phenylcarboxylate,
4-[3-alkyl($C_{3-15}$)oxypropyl]phenyl 4'-[alkyl($C_{3-20}$)oxy]biphenylcarboxylate,
4-[4-alkyl($C_{3-15}$)oxybutyl]phenyl 4'-[alkyl($C_{3-20}$)oxy]biphenylylcarboxylate,
4-[5-alkyl($C_{3-15}$)oxypentyl]phenyl 4'-[alkyl($C_{3-20}$)oxy]biphenylcarboxylate,
4-[6-alkyl($C_{3-15}$)oxyhexyl]phenyl 4'-[alkyl($C_{3-20}$)oxy]biphenylcarboxylate,
4-[3-alkyl($C_{3-15}$)oxypropyl]phenyl 4'-[alkyl($C_{3-20}$)]biphenylcarboxylate,
4-[4-alkyl($C_{3-15}$)oxybutyl]phenyl 4'-[alkyl($C_{3-20}$)]biphenylcarboxylate,
4-[5-alkyl($C_{3-15}$)oxypentyl]phenyl 4'-[alkyl($C_{3-20}$)]biphenylcarboxylate,
4-[6-alkyl($C_{3-15}$)oxyhexyl]phenyl 4'-[alkyl($C_{3-20}$)]biphenylcarboxylate,
4-[3-alkyl($C_{3-15}$)oxypropyl]benzoic acid 4-[alkyl($C_{3-20}$)oxycarbonyl]phenyl ester,
4-[4-alkyl($C_{3-15}$)oxybutyl]benzoic acid 4-[alkyl($C_{3-20}$)oxycarbonyl]phenyl ester,
4-[5-alkyl($C_{3-15}$)oxypentyl]benzoic acid 4-[alkyl($C_{3-20}$)oxycarbonyl]phenyl ester,
4-[6-alkyl($C_{3-15}$)oxyhexyl]benzoic acid 4-[alkyl($C_{3-20}$)oxycarbonyl]phenyl ester,
4-[3-alkyl($C_{3-15}$)oxypropyl]benzoic acid 4'-[alkyl($C_{3-20}$)oxycarbonyl]biphenylyl ester,
4-[4-alkyl($C_{3-15}$)oxybutyl]benzoic acid 4'-[alkyl($C_{3-20}$)oxycarbonyl]biphenyl ester,
4-[5-alkyl($C_{3-15}$)oxypentyl]benzoic acid 4'-[alkyl($C_{3-20}$)oxycarbonyl]biphenylyl ester,
4-[6-alkyl($C_{3-15}$)oxyhexyl]benzoic acid 4'-[alkyl($C_{3-20}$)oxycarbonyl]biphenylyl ester,
4-[alkyl($C_{3-15}$)oxymethyl]phenyl 4-[alkyl($C_{3-20}$)oxyphenylcarboxylate,
4-[2-alkyl($C_{3-15}$)oxyethyl]phenyl 4-[alkyl($C_{3-20}$)oxy]phenylcarboxylate,
4-[alkyl($C_{3-15}$)oxymethyl]phenyl 4-[alkyl($C_{3-20}$)]phenylcarboxylate,
4-[2-alkyl($C_{3-15}$)oxyethyl]phenyl 4-[alkyl($C_{3-20}$)]phenylcarboxylate,
4-[alkyl($C_{3-15}$)oxymethyl]phenyl 4'-[alkyl($C_{3-20}$)oxy]biphenylcarboxylate,
4-[2-alkyl($C_{3-15}$)oxyethyl]phenyl 4'-[alkyl($C_{3-20}$)oxy]biphenylcarboxylate,
4-[alkyl($C_{3-15}$)oxymethyl]phenyl 4'-[alkyl($C_{3-20}$)]biphenylcarboxylate,
4-[2-alkyl($C_{3-15}$)oxyethyl]phenyl 4'-[alkyl($C_{3-20}$)]biphenylcarboxylate,
4-[alkyl($C_{3-15}$)oxymethyl]phenyl 4-[alkyl($C_{3-20}$)oxycarbonyl]phenylcarboxylate,
4-[2-alkyl($C_{3-15}$)oxyethyl]phenyl 4-[alkyl($C_{3-20}$)oxycarbonyl]phenylcarboxylate,
4-[alkyl($C_{3-15}$)oxymethyl]phenyl 4'-[alkyl($C_{3-20}$)oxycarbonyl]biphenylcarbxylate,
4-[2-alkyl($C_{3-15}$)oxyethyl]phenyl 4'-[alkyl($C_{3-20}$)oxycarbonyl]biphenylcarbxylate,
4-[alkyl($C_{3-15}$)oxymethyl]phenyl 4-[alkyl($C_{3-20}$)carbonyloxy]phenylcarboxylate,
4-[2-alkyl($C_{3-15}$)oxyethyl]phenyl 4-[alkyl($C_{3-20}$)carbonyloxy]phenylcarboxylate,
4-[alkyl($C_{3-15}$)oxymethyl]phenyl 4-[alkyl($C_{3-20}$)carbonyloxy]biphenylcarboxylate,
4-[2-alkyl($C_{3-15}$)oxyethyl]phenyl 4-[alkyl($C_{3-20}$)carbonyloxy]biphenylcarboxylate,
4-[alkoxyalkyl($C_{3-15}$)oxymethyl]benzoic acid 4-[alkyl($C_{3-20}$)oxy]phenyl ester,
4-[2-alkoxyalkyl($C_{3-15}$)oxyethyl]benzoic acid 4-[alkyl($C_{3-20}$)oxy]phenyl ester,
4-[alkoxyalkyl($C_{3-15}$)oxymethyl]benzoic acid 4-[alkyl($C_{3-20}$)]phenyl ester,
4-[2-alkoxyalkyl($C_{3-15}$)oxyethyl]benzoic acid 4-[alkyl($C_{3-20}$)]phenyl ester,
4-[alkylalkyl($C_{3-15}$)oxymethyl]benzoic acid 4'-[alkyl($C_{3-20}$)oxy]biphenylyl ester, 4-[2-alkoxyalkyl($C_{3-15}$)oxyethyl]benzoic acid 4'-[alkyl($C_{3-20}$)oxy]biphenylyl ester,
4-[alkoxyalkyl($C_{3-15}$)oxymethyl]benzoic acid 4'-[alkyl($C_{3-20}$)]biphenylyl ester,
4-[2-alkoxyalkyl($C_{3-15}$)oxyethyl]benzoic acid 4'-[alkyl($C_{3-20}$)]biphenylyl ester,
4-[alkoxyalkyl($C_{3-15}$)oxymethyl]benzoic acid 4-[alkyl($C_{3-20}$)oxycarbonyl]phenyl ester,
4-[2-alkoxyalkyl($C_{3-15}$)oxyethyl]benzoic acid 4-[alkyl($C_{3-20}$)oxycarbonyl]phenyl ester,
4-[alkoxyalkyl($C_{3-15}$)oxymethyl]benzoic acid 4'-[alkyl($C_{3-20}$)oxycarbonyl]biphenylyl ester,
4-[2-alkoxyalkyl($C_{3-15}$)oxyethyl]benzoic acid 4'-[alkyl($C_{3-20}$)oxycarbonyl]biphenylyl ester,
4-[alkoxyalkyl($C_{3-15}$)oxymethyl]benzoic acid 4-alkyl($C_{3-20}$)carbonyloxy]phenyl ester,
4-[2-alkoxyalkyl($C_{3-15}$)oxyethyl]benzoic acid 4-[alkyl($C_{3-20}$)carbonyloxy]phenyl ester,
4-[alkoxyalkyl($C_{3-15}$)oxymethyl]benzoic acid 4'-[alkyl($C_{3-20}$)carbonyloxy]biphenylyl ester,
4-[2-alkoxyalkyl($C_{3-15}$)oxyethyl]benzoic acid 4'-[alkyl($C_{3-20}$)carbonyloxy]biphenylyl ester,
4-[alkyl($C_{3-15}$)carbonyloxymethyl]benzoic acid 4-[alkyl($C_{3-20}$)oxy]phenyl ester,
4-[2-alkyl($C_{3-15}$)carbonyloxyethyl]benzoic acid 4-[alkyl($C_{3-20}$)oxy]phenyl ester,
4-[alkyl($C_{3-15}$)carbonyloxymethyl]benzoic acid 4-[alkyl($C_{3-20}$)]phenyl ester,
4-[alkyl($C_{3-15}$)carbonyloxyethyl]benzoic acid 4-[alkyl($C_{3-20}$)]phenyl ester,
4-[alkyl($C_{3-15}$)carbonyloxymethyl]benzoic acid 4'-[alkyl($C_{3-20}$)oxy]biphenylyl ester,
4-[2-alkyl($C_{3-15}$)carbonyloxyethyl]benzoic acid 4'-[alkyl($C_{3-20}$)oxy]biphenylyl ester,
4-[alkyl($C_{3-15}$)carbonyloxymethyl]benzoic acid 4'-[alkyl($C_{3-20}$)]biphenylyl ester,
4-[2-alkyl($C_{3-15}$)carbonyloxyethyl]benzoic acid 4'-[alkyl($C_{3-20}$)]biphenylyl ester,
4-[alkyl($C_{3-15}$)carbonyloxymethyl]benzoic acid 4-[alkyl($C_{3-20}$)oxycarbonyl]phenyl ester,
4-[2-alkyl($C_{3-15}$)carbonyloxyethyl]benzoic acid 4-[alkyl($C_{3-20}$)oxycarbonyl]phenyl ester,
4-[alkyl($C_{3-15}$)carbonyloxymethyl]benzoic acid 4'-[alkyl($C_{3-20}$)oxycarbonyl]biphenylyl ester,
4-[2-alkyl($C_{3-15}$)carbonyloxyethyl]benzoic acid 4'-[alkyl($C_{3-20}$)oxycarbonyl]biphenylyl ester,
4-[alkyl($C_{3-15}$)carbonyloxymethyl]benzoic acid 4-[alkyl($C_{3-20}$)carbonyloxy]phenyl ester,
4-[2-alkyl($C_{3-15}$)carbonyloxyethyl]benzoic acid 4-[alkyl($C_{3-20}$)carbonyloxy]phenyl ester,
4-[alkyl($C_{3-20}$)carbonyloxymethyl]benzoic acid 4'-[alkyl($C_{3-20}$)carbonyloxy]biphenylyl ester,
4-[2-alkyl($C_{3-15}$)carbonyloxyethyl]benzoic acid 4'-[alkyl($C_{3-20}$)carbonyloxy]biphenylyl ester,
4-[alkoxyalkyl($C_{3-15}$)carbonyloxymethyl]benzoic acid 4-[alkyl($C_{3-20}$)oxy]phenyl ester,
4-[2-alkoxyalkyl($C_{3-15}$)carbonyloxyethyl]benzoic acid 4-[alkyl($C_{3-20}$)oxy]phenyl ester,
4-[alkoxyalkyl($C_{3-15}$)carbonyloxymethyl]benzoic acid 4-[alkyl($C_{3-20}$)]phenyl ester,
4-[2-alkoxyalkyl($C_{3-15}$)carbonyloxyethyl]benzoic acid 4-[alkyl($C_{3-20}$)]phenyl ester,
4-[alkoxyalkyl($C_{3-15}$)carbonyloxymethyl]benzoic acid 4'-[alkyl($C_{3-20}$)oxy]biphenylyl ester,
4-[2-alkoxyalkyl($C_{3-15}$)carbonyloxyethyl]benzoic acid 4'-[alkyl($C_{3-20}$)oxy]biphenylyl ester,
4-[alkoxyalkyl($C_{3-15}$)carbonyloxymethyl]benzoic acid 4'-[alkyl($C_{3-20}$)]biphenylyl ester,
4-[2-alkoxyalkyl($C_{3-15}$)carbonyloxyethyl]benzoic acid 4'-[alkyl($C_{3-20}$)]biphenylyl ester,
4-[alkoxyalkyl($C_{3-15}$)carbonyloxymethyl]benzoic acid 4-[alkyl($C_{3-20}$)oxycarbonyl]phenyl ester,
4-[2-alkoxyalkyl($C_{3-15}$)carbonyloxyethyl]benzoic acid 4-[alkyl($C_{3-20}$)oxycarbonyl]phenyl ester,
4-[alkoxyalkyl($C_{3-15}$)carbonyloxymethyl]benzoic acid 4'-[alkyl($C_{3-20}$)oxycarbonyl]biphenylyl ester,
4-[2-alkoxyalkyl($C_{3-15}$)carbonyloxyethyl]benzoic acid 4'-[alkyl($C_{3-20}$)oxycarbonyl]biphenylyl ester,
4-[alkoxyalkyl($C_{3-15}$)carbonyloxymethyl]benzoic acid 4-alkyl($C_{3-20}$)carbonyloxy]phenyl ester,
4-[2-alkoxyalkyl($C_{3-15}$)carbonyloxyethyl]benzoic acid 4-[alkyl($C_{3-20}$)carbonyloxy]phenyl ester,
4-[alkoxyalkyl($C_{3-15}$)carbonyloxymethyl]benzoic acid 4'-[alkyl($C_{3-20}$)carbonyloxy]biphenylyl ester,
4-[2-alkoxyalkyl($C_{3-15}$)carbonyloxyethyl]benzoic acid 4'-[alkyl($C_{3-20}$)carbonyloxy]biphenylyl ester,
4-[3-alkoxyalkyl($C_{3-15}$)oxypropyl]benzoic acid 4-[alkyl($C_{3-20}$)oxy]phenyl ester,
4-[4-alkoxyalkyl($C_{3-15}$)oxybutyl]benzoic acid 4-[alkyl($C_{3-20}$)oxy]phenyl ester,
4-[5-alkoxyalkyl($C_{3-15}$)oxypentyl]benzoic acid 4-[alkyl($C_{3-20}$)oxy]phenyl ester,
4-[6-alkoxyalkyl($C_{3-15}$)oxyhexyl]benzoic acid 4-[alkyl($C_{3-20}$)oxy]phenyl ester,
4-[3-alkoxyalkyl($C_{3-15}$)oxypropyl]benzoic acid 4-[alkyl($C_{3-20}$)]phenyl ester,
4-[4-alkoxyalkyl($C_{3-15}$)oxybutyl]benzoic acid 4-[alkyl($C_{3-20}$)]phenyl ester,
4-[5-alkoxyalkyl($C_{3-15}$)oxypentyl]benzoic acid 4-[alkyl($C_{3-20}$)]phenyl ester,
4-[6-alkoxyalkyl($C_{3-15}$)oxyhexyl]benzoic acid 4-[alkyl($C_{3-20}$)]phenyl ester,
4-[3-alkoxyalkyl($C_{3-15}$)oxypropyl]benzoic acid 4'-[alkyl($C_{3-20}$)oxy]biphenylyl ester,
4-[4-alkoxyalkyl($C_{3-15}$)oxybutyl]benzoic acid 4'-[alkyl($C_{3-20}$)oxy]biphenylyl ester,
4-[5-alkoxyalkyl($C_{3-15}$)oxypentyl]benzoic acid 4'-[alkyl($C_{3-20}$)oxy]biphenylyl ester,
4-[6-alkoxyalkyl($C_{3-15}$)oxyhexyl]benzoic acid 4'-[alkyl($C_{3-20}$)oxy]biphenylyl ester,
4-[3-alkoxyalkyl($C_{3-15}$)oxypropyl]benzoic acid 4'-alkyl($C_{3-20}$)]biphenylyl ester,
4-[4-alkoxyalkyl($C_{3-15}$)oxybutyl]benzoic acid 4'-[alkyl($C_{3-20}$)]biphenylyl ester,
4-[alkoxyalkyl($C_{3-15}$)oxypentyl]benzoic acid 4'-[alkyl($C_{3-20}$)]biphenylyl ester,
4-[6-alkoxyalkyl($C_{3-15}$)oxyhexyl]benzoic acid 4'-[alkyl($C_{3-20}$)]biphenylyl ester,
4-[3-alkoxyalkyl($C_{3-15}$)oxypropyl]phenyl 4-[alkyl($C_{3-20}$)]phenylcarboxylate,
4-[4-alkoxyalkyl($C_{3-15}$)oxybutyl]phenyl 4-[alkyl($C_{3-20}$)]phenylcarboxylate,
4-[5-alkoxyalkyl($C_{3-15}$)oxypentyl]phenyl 4-[alkyl($C_{3-20}$)]phenylcarboxylate,
4-[6-alkoxyalkyl($C_{3-15}$)oxyhexyl]phenyl 4-[alkyl($C_{3-20}$)]phenylcarboxylate,
4-[3-alkoxyalkyl($C_{3-15}$)oxypropyl]phenyl 4-[alkyl($C_{3-20}$)oxy]phenylcarboxylate,
4-[4-alkoxyalkyl($C_{3-15}$)oxybutyl]phenyl 4-[alkyl($C_{3-20}$)oxy]phenylcarboxylate,
4-[5-alkoxyalkyl($C_{3-15}$)oxypentyl]phenyl 4-[alkyl($C_{3-20}$)oxy]phenylcarboxylate,
4-[6-alkoxyalkyl($C_{3-15}$)oxyhexyl]phenyl 4-[alkyl($C_{3-20}$)oxy]phenylcarboxylate,
4-[3-alkoxyalkyl($C_{3-15}$)oxypropyl]phenyl 4'-[alkyl($C_{3-20}$)oxy]biphenylcarboxylate, 4-[4-alkoxyalkyl($C_{3-15}$)oxybutyl]phenyl 4'-[alkyl($C_{3-20}$)oxy]biphenylcarboxylate,
4-[5-alkoxyalkyl($C_{3-15}$)oxypentyl]phenyl 4'-[alkyl($C_{3-20}$)oxy]biphenylcarboxylate,
4-[6-alkoxyalkyl($C_{3-15}$)oxyhexyl]phenyl 4'-[alkyl($C_{3-20}$)oxy]biphenylcarboxylate,
4-[3-alkoxyalkyl($C_{3-15}$)oxypropyl]phenyl 4'-[alkyl($C_{3-20}$)]biphenylcarboxylate,
4-[4-alkoxyalkyl($C_{3-15}$)oxybutyl]phenyl 4'-[alkyl($C_{3-20}$)]biphenylcarboxylate,
4-[5-alkoxyalkyl($C_{3-15}$)oxypentyl]phenyl 4'-[alkyl($C_{3-20}$)]biphenylcarboxylate,
4-[6-alkoxyalkyl($C_{3-15}$)oxyhexyl]phenyl 4'-[alkyl($C_{3-20}$)]biphenylcarboxylate,
4-[3-alkoxyalkyl($C_{3-15}$)oxypropyl]benzoic acid 4-[alkyl($C_{3-20}$)oxycarbonyl]phenyl ester,
4-[4-alkoxyalkyl($C_{3-15}$)oxybutyl]benzoic acid 4-[alkyl($C_{3-20}$)oxycarbonyl]phenyl ester,
4-[5-alkoxyalkyl($C_{3-15}$)oxypentyl]benzoic acid 4-[alkyl($C_{3-20}$)oxycarbonyl]phenyl ester,
4-[6-alkoxyalkyl($C_{3-15}$)oxyhexyl]benzoic acid 4-[alkyl($C_{3-20}$)oxycarbonyl]phenyl ester,
4-[3-alkoxyalkyl($C_{3-15}$)oxypropyl]benzoic acid 4'-[alkyl($C_{3-20}$)oxycarbonyl]biphenylyl ester,
4-[4-alkoxyalkyl($C_{3-15}$)oxybutyl]benzoic acid 4'-[alkyl($C_{3-20}$)oxycarbonyl]biphenylyl ester,
4-[5-alkoxyalkyl($C_{3-15}$)oxypentyl]benzoic acid 4'-[alkyl($C_{3-20}$)oxycarbonyl]biphenylyl ester,
4-[6-alkoxyalkyl($C_{3-15}$)oxyhexyl]benzoic acid 4'-[alkyl($C_{3-20}$)oxycarbonyl]biphenylyl ester,
4-[3-alkyl($C_{3-15}$)carbonyloxypropyl]benzoic acid 4-[alkyl($C_{3-20}$)oxy]phenyl ester,
4-[4-alkyl($C_{3-15}$)carbonyloxybutyl]benzoic acid 4-[alkyl($C_{3-20}$)oxy]phenyl ester,
4-[5-alkyl($C_{3-15}$)carbonyloxypentyl]benzoic acid 4-[alkyl($C_{3-20}$)oxy]phenyl ester,
4-[6-alkoxyalkyl($C_{3-15}$)carbonyloxyhexyl]benzoic acid 4-[alkyl($C_{3-20}$)oxy]phenyl ester,
4-[3-alkyl($C_{3-15}$)carbonyloxypropyl]benzoic acid 4'-[alkyl($C_{3-20}$)]phenyl ester,
4-[4-alkyl($C_{3-15}$)carbonyloxybutyl]benzoic acid 4-[alkyl($C_{3-20}$)]phenyl ester,
4-[5-alkyl($C_{3-15}$)carbonyloxypentyl]benzoic acid 4-[alkyl($C_{3-20}$)]phenyl ester,
4-[6-alkyl($C_{3-15}$)carbonyloxyhexyl]benzoic acid 4-[alkyl($C_{3-20}$)]phenyl ester,
4-[3-alkyl($C_{3-15}$)carbonyloxypropyl]benzoic acid 4'-[alkyl($C_{3-20}$)oxy]biphenylyl ester,
4-[4-alkyl($C_{3-15}$)carbonyloxybutyl]benzoic acid 4'-[alkyl($C_{3-20}$)oxy]biphenylyl ester,
4-[5-alkyl($C_{3-15}$)carbonyloxypentyl)benzoic acid 4'-[alkyl($C_{3-20}$)oxy]biphenylyl ester,
4-[6-alkyl($C_{3-15}$)carbonyloxyhexyl]benzoic acid 4'-[alkyl($C_{3-20}$)oxy]biphenylyl ester,
4-[3-alkyl($C_{3-15}$)carbobyloxypropylbenzoic acid 4'-[alkyl($C_{3-20}$)oxy]biphenylyl ester,
4-[4-alkyl($C_{3-15}$)carbonyloxybutyl]benzoic acid 4'-[alkyl($C_{3-20}$)]biphenylyl ester,
4-[5-alkyl($C_{3-15}$)carbonyloxypentyl]benzoic acid 4'-[alkyl($C_{3-20}$)]biphenylyl ester,
4-[6-alkyl($C_{3-15}$)carbonyloxyhexyl]benzoic acid 4'-[alkyl($C_{3-20}$)]biphenylyl ester,
4-[3-alkyl($C_{3-15}$)carbonyloxypropyl]benzoic acid 4-[alkyl($C_{3-20}$)]phenylcarboxylate,
b 4-[4-alkyl($C_{3-15}$)carbonyloxybutyl]phenyl 4-[alkyl($C_{3-20}$)]phenylcarboxylate,
4-[5-alkyl($C_{3-15}$)carbonyloxypentyl]phenyl 4-[alkyl($C_{3-20}$)]phenylcarboxylate,
4-[6-alkyl($C_{3-15}$)carbonyloxyhexyl]phenyl 4-alkyl($C_{3-20}$)]phenylcarboxylate,
4-[3-alkyl($C_{3-15}$)carbonyloxypropyl]phenyl 4-[alkyl($C_{3-20}$)oxy]phenylcarboxylate,
4-[4-alkyl($C_{3-15}$)carbonyloxybutyl]phenyl 4-[alkyl($C_{3-20}$)oxy]phenylcarboxylate,
4-[5-alkyl($C_{3-15}$)carbonyloxypentyl]phenyl 4-[alkyl($C_{3-20}$)oxy]phenylcarboxylate,
4-[6-alkyl($C_{3-15}$)carbonyloxyhexyl]phenyl 4'-[alkyl($C_{3-20}$)oxy]phenylcarboxylate,
4-[3-alkyl($C_{3-15}$)carbonyloxypropyl]phenyl 4'-[alkyl($C_{3-20}$)oxy]biphenylcarboxylate,
4-[4-alkyl($C_{3-15}$)carbonyloxybutyl]phenyl 4'-[alkyl($C_{3-20}$)oxy]biphenylcarboxylate,
4-[5-alkyl($C_{3-15}$)carbonyloxypentyl]phenyl 4'-[alkyl($C_{3-20}$)oxy]biphenylcarboxylate,
4-[6-alkyl($C_{3-15}$)carbonyloxyhexyl]phenyl 4'-[alkyl($C_{3-20}$)oxy]biphenylcarboxylate,
4-[3-alkyl($C_{3-15}$)carbonyloxypropyl]phenyl 4'-[alkyl($C_{3-20}$)]biphenylcarboxylate,
4-[4-alkyl($C_{3-15}$)carbonyloxybutyl]phenyl 4'-[alkyl($C_{3-20}$)biphenylcarboxylate,
4-[5-alkyl($C_{3-15}$)carbonyloxypentyl]phenyl 4'-[alkyl($C_{3-20}$)]biphenylcarboxylate,
4-[6-alkyl($C_{3-15}$)carbonyloxyhexyl]phenyl 4'-[alkyl($C_{3-20}$)]biphenylcarboxylate,
4-[3-alkyl($C_{3-15}$)carbonyloxypropyl]benzoic acid 4-[alkyl($C_{3-20}$)oxycarbonyl]phenyl ester,
4-[alkyl($C_{3-15}$)carbonyloxybutyl]benzoic acid 4-[alkyl($C_{3-20}$)oxycarbonylphenyl ester,
4-[5-alkyl($C_{3-15}$)carbonyloxypentyl]benzoic acid 4-[alkyl($C_{3-20}$)oxycarbonyl]phenyl ester,
4-[6-alkyl($C_{3-15}$)carbonyloxyhexyl]benzoic acid 4-[alkyl($C_{3-20}$)oxycarbonyl]phenyl ester,
4-[3-alkyl($C_{3-15}$)carbonyloxypropyl]benzoic acid 4'-[alkyl($C_{3-20}$)oxycarbonyl]biphenylyl ester,
4-[4-alkyl($C_{3-15}$)carbonyloxybutyl]benzoic acid 4'-[alkyl($C_{3-20}$)oxycarbonyl]biphenylyl ester,
4-[5-alkyl($C_{3-15}$)carbonyloxypentyl]benzoic acid 4'-[alkyl($C_{3-20}$)oxycarbonyl]biphenylyl ester,
4-[6-alkyl($C_{3-15}$)carbonyloxyhexyl]benzoic acid 4'-[alkyl($C_{3-20}$)oxycarbonyl]biphenylyl ester,
4-[3-alkoxyalkyl($C_{3-15}$)carbonyloxypropyl]benzoic acid 4-[alkyl($C_{3-20}$)oxy]phenyl ester,
4-[4-alkoxyalkyl($C_{3-15}$)carbonyloxybutyl]benzoic acid 4-[alkyl($C_{3-20}$)oxy]phenyl ester,
4-[5-alkoxyalkyl($C_{3-15}$)carbonyloxypentyl]benzoic acid 4-[alkyl($C_{3-20}$)oxy]phenyl ester,
4-[6-alkoxyalkyl($C_{3-15}$)carbonyloxyhexyl]benzoic acid 4-[alkyl($C_{3-20}$)oxy]phenyl ester,
4-[3-alkoxyalkyl($C_{3-15}$)carbonyloxypropyl]benzoic acid 4'-[alkyl($C_{3-20}$)]phenyl ester,
4-[4-alkoxyalkyl($C_{3-15}$)carbonyloxybutyl]benzoic acid 4-[alkyl($C_{3-20}$)phenyl ester,
4-[5-alkoxyalkyl($C_{3-15}$)carbonyloxypentyl]benzoic acid 4-[alkyl($C_{3-20}$)]phenyl ester,
4-[6-alkoxyalkyl($C_{3-15}$)carbonyloxyhexyl]benzoic acid 4-[alkyl($C_{3-20}$)]phenyl ester,
4-[3-alkoxyalkyl($C_{3-15}$)carbonyloxypropyl]benzoic acid 4'-[alkyl($C_{3-20}$)oxy]biphenylyl ester,
4-[4-alkoxyalkyl($C_{3-15}$)carbonyloxybytyl]benzoic acid 4'-[alkyl($C_{3-20}$)oxy]biphenylyl ester,
4-[5-alkoxyalkyl($C_{3-15}$)carbonyloxyphentyl]-benzoic acid 4'-[alkyl($C_{3-20}$)oxy]biphenylyl ester,
4-[6-alkoxyalkyl($C_{3-15}$)carbonyloxyhexyl]benzoic acid 4'-[alkyl($C_{3-20}$)oxy]biphenylyl ester,
4-[3-alkoxyalkyl($C_{3-15}$)carbonyloxypropyl]benzoic acid 4'-[alkyl($C_{3-20}$)]biphenylyl ester, 4-[4-alkoxyalkyl($C_{3-15}$)carbonyloxybutyl]benzoic acid 4'-[alkyl($C_{3-20}$)]biphenylyl ester,
4-[5-alkoxyalkyl($C_{3-15}$)carbonyloxypentyl]benzoic acid 4'-[alkyl($C_{3-20}$)]biphenylyl ester,
4-[6-alkoxyalkyl($C_{3-15}$)carbonyloxyhexyl]benzoic acid 4'-[alkyl($C_{3-20}$)]biphenylyl ester,
4-[3-alkoxyalkyl($C_{3-15}$)carbonyloxypropyl]phenyl 4-[alkyl($C_{3-20}$)]phenylcarboxylate,
4-[4-alkoxyalkyl($C_{3-15}$)carbonyloxybutyl]phenyl 4-[alkyl($C_{3-20}$)]phenylcarboxylate,
4-[5-alkoxyalkyl($C_{3-15}$)carbonyloxypentyl]phenyl 4-[alkyl($C_{3-20}$)]phenylcarboxylate,
4-[6-alkoxyalkyl($C_{3-15}$)carbonyloxyhexyl]phenyl 4-[alkyl($C_{3-20}$)]phenylcarboxylate,
4-[3-alkoxyalkyl($C_{3-15}$)carbonyloxypropyl]phenyl 4-[alkyl($C_{3-20}$)oxy]phenylcarboxylate,
4-[4-alkoxyalkyl($C_{3-15}$)carbonyloxybutyl]phenyl 4-[alkyl($C_{3-20}$)oxy]phenylcarboxylate,
4-[5-alkoxyalkyl($C_{3-15}$)carbonyloxypentyl]phenyl 4-[alkyl($C_{3-20}$)oxy]phenylcarboxylate,
4-[6-alkoxyalkyl($C_{3-15}$)carbonyloxyhexyl]phenyl 4-[alkyl($C_{3-20}$)oxy]phenylcarboxylate,
4-[3-alkoxyalkyl($C_{3-15}$)carbonyloxypropyl]phenyl 4'-[alkyl($C_{3-20}$)oxy]biphenylcarboxylate,
4-[4-alkoxyalkyl($C_{3-15}$)carbonyloxybutyl]phenyl 4'-[alkyl($C_{3-20}$)oxy]biphenylcarboxylate,
4-[5-alkoxyalkyl($C_{3-15}$)carbonyloxypentyl]phenyl 4'-[alkyl($C_{3-20}$)oxy]biphenylcarboxylate,
4-[6-alkoxyalkyl($C_{3-15}$)carbonyloxyhexyl]phenyl 4'-[alkyl($C_{3-20}$)oxy]biphenylcarboxylate,
4-[3-alkoxyalkyl($C_{3-15}$)carbonyloxypropyl]phenyl 4'-[alkyl($C_{3-20}$)]biphenylcarboxylate,
4-[4-alkoxyalkyl($C_{3-15}$)carbonyloxybutyl]phenyl 4'-[alkyl($C_{3-20}$)]biphenylcarboxylate,
4-[5-alkoxyalkyl($C_{3-15}$)carbonyloxypentyl]phenyl 4'-[alkyl($C_{3-20}$)]biphenylcarboxylate,
4-[6-alkoxyalkyl($C_{3-15}$)carbonyloxyhexyl]phenyl 4'-[alkyl($C_{3-20}$)]biphenylcarboxylate,
4-[3-alkoxyalkyl($C_{3-15}$)carbonyloxypropyl]benzoic acid 4-alkyl($C_{3-20}$)oxycarbonyl]phenyl ester,
4-[4-alkoxyalkyl($C_{3-15}$)carbonyloxybutyl]benzoic acid 4-[alkyl($C_{3-20}$)oxycarbonyl]phenyl ester,
4-[5-alkoxyalkyl($C_{3-15}$)carbonyloxypentyl]benzoic acid 4-[alkyl($C_{3-20}$)oxycarbonyl]phenyl ester,
4-[6-alkoxyalkyl($C_{3-15}$)carbonyloxyhexyl]benzoic acid 4-[alkyl($C_{3-20}$)oxycarbonyl]phenyl ester,
4-[3-alkoxyalkyl($C_{3-15}$)carbonyloxypropyl]benzoic acid 4-[alkyl($C_{3-20}$)oxycarbonyl]biphenylyl ester,
4-[4-alkoxyalkyl($C_{3-15}$)carbonyloxybutyl]benzoic acid 4-[alkyl($C_{3-20}$)oxycarbonyl]biphenylyl ester,
4-[5-alkoxyalkyl($C_{3-15}$)carbonyloxypentyl]benzoic acid 4-[alkyl($C_{3-20}$)oxycarbonyl]biphenylyl ester,
4-[6-alkoxyalkyl($C_{3-15}$)carbonyloxyhexyl]benzoic acid 4-[alkyl($C_{3-20}$)oxycarbonyl]biphenylyl ester,
4-[alkoxyalkyl($C_{3-15}$)oxymethyl]phenyl 4-[alkyl($C_{3-20}$)oxy]phenylcarboxylate,
4-[2-alkoxyalkyl($C_{3-15}$)oxyethyl]phenyl 4-[alkyl($C_{3-20}$)oxy]phenylcarboxylate,
4-[alkoxyalkyl($C_{3-15}$)oxymethyl]phenyl 4-[alkyl($C_{3-20}$)]phenylcarboxylate,
4-[2-alkoxyalkyl($C_{3-15}$)oxyethyl]phenyl 4-[alkyl($C_{3-20}$)]phenylcarboxylate,
4-[alkoxyalkyl($C_{3-15}$)oxymethyl]phenyl 4'-[alkyl($C_{3-20}$)oxy]biphenylcarboxylate,
4-[2-alkoxyalkyl($C_{3-15}$)oxyethyl]phenyl 4'-[alkyl($C_{3-20}$)oxy]biphenylcarboxylate,
4-[alkoxyalkyl($C_{3-15}$)oxymethyl]phenyl 4'-[alkyl($C_{3-20}$)]biphenylcarboxylate,
4-[2-alkoxyalkyl($C_{3-15}$)oxyethyl]phenyl 4'-[alkyl($C_{3-20}$)]biphenylcarboxylate,
4-[alkoxyalkyl($C_{3-15}$)oxymethyl]phenyl 4-[alkyl($C_{3-20}$)oxycarbonyl]phenylcarboxylate,
4-[2-alkoxyalkyl($C_{3-15}$)oxyethyl]phenyl 4-[alkyl($C_{3-20}$)oxycarbonyl]phenylcarboxylate,
4-[alkoxyalkyl($C_{3-15}$)oxymethyl]phenyl 4'-[alkyl($C_{3-20}$)oxycarbonyl]biphenylcarboxylate,
4-[2-alkoxyalkyl($C_{3-15}$)oxyethyl]phenyl 4'-[alkyl($C_{3-20}$)oxycarbonyl]biphenylcarboxylate,
4-[alkoxyalkyl($C_{3-15}$)oxymethyl]phenyl 4-[alkyl($C_{3-20}$)carbonyloxy]phenylcarboxylate,
4-[2-alkoxyalkyl($C_{3-15}$)oxyethyl]phenyl 4-[alkyl($C_{3-20}$)carbonyloxy]phenylcarboxylate,
4-[alkoxyalkyl($C_{3-15}$)oxymethyl]phenyl 4'-[alkyl($C_{3-20}$)carbonyloxy]biphenylcarboxylate,
4-[2-alkoxyalkyl($C_{3-15}$)oxyethyl]phenyl 4'-[alkyl($C_{3-20}$)carbonyloxy]biphenylcarboxylate,
4-[alkyl($C_{3-15}$)carbonyloxymethyl]phenyl 4-[alkyl($C_{3-20}$)oxy]phenylcarboxylate,
4-[2-alkyl($C_{3-15}$)carbonyloxyethyl]phenyl 4-[alkyl($C_{3-20}$)oxy]phenylcarboxylate,
4-[alkyl($C_{3-15}$)carbonyloxymethyl]phenyl 4-[alkyl($C_{3-20}$)]phenylcarboxylate,
4-[2-alkyl($C_{3-15}$)carbonyloxyethyl]phenyl 4-[alkyl($C_{3-20}$)]phenylcarboxylate,
4-[alkyl($C_{3-15}$)carbonyloxymethyl]phenyl 4'-[alkyl($C_{3-20}$)oxy]biphenylcarboxylate,
4-[2-alkyl($C_{3-15}$)carbonyloxyethyl]phenyl 4'-[alkyl($C_{3-20}$)oxy]biphenylcarboxylate,
4-[alkyl($C_{3-15}$)carbonyloxymethyl]phenyl 4'-[alkyl($C_{3-20}$)]biphenylcarboxylate,
4-[alkyl($C_{3-15}$)carbonyloxyethyl]phenyl 4'-[alkyl($C_{3-20}$)]biphenylcarboxylate,
4-[alkyl($C_{3-15}$)carbonyloxymethyl]phenyl 4-[alkyl($C_{3-20}$)oxycarbonyl]phenylcarboxylate,
4-[2-alkyl($C_{3-15}$)carbonyloxyethyl]phenyl 4-[alkyl($C_{3-20}$)oxycarbonyl]phenylcarboxylate,
4-[alkyl($C_{3-15}$)carbonyloxymethyl]phenyl 4'-[alkyl($C_{3-20}$)oxycarbonyl]biphenylcarboxylate,
4-[2-alkyl($C_{3-15}$)carbonyloxyethyl]phenyl 4'-[alkyl($C_{3-20}$)oxycarbonyl]biphenylcarboxylate,
4-[alkyl($C_{3-15}$)carbonyloxymethyl]phenyl 4-[5-alkyl($C_{3-20}$)carbonyloxy]phenylcarboxylate,
4-[2-alkyl($C_{3-15}$)carbonyloxyethyl]phenyl 4-[alkyl($C_{3-20}$)carbonyloxy]phenylcarboxylate,
4-[alkyl($C_{3-15}$)carbonyloxymethyl]phenyl 4'-[alkyl($C_{3-20}$)carbonyloxy]biphenylcarboxylate,
4-[2-alkyl($C_{3-15}$)carbonyloxyethyl]phenyl 4'-[alkyl($C_{3-20}$)carbonyloxy]biphenylcarboxylate,
4-[alkoxyalkyl($C_{3-15}$)carbonyloxymethyl]phenyl 4-[alkyl($C_{3-20}$)oxy]phenylcarboxylate,
4-[2-alkoxyalkyl($C_{3-15}$)carbonyloxyethyl]phenyl 4-[alkyl($C_{3-20}$)oxy]phenylcarboxylate,
4-[alkoxyalkyl($C_{3-15}$)carbonyloxymethyl]phenyl 4-[alkyl($C_{3-20}$)]phenylcarboxylate,
4-[2-alkoxyalkyl($C_{3-15}$)carbonyloxyethyl]phenyl 4-[alkyl($C_{3-20}$)]phenylcarboxylate,
4-[alkoxyalkyl($C_{3-15}$)carbonyloxymethyl]phenyl 4'-[alkyl($C_{3-20}$)oxy]biphenylcarboxylate,
4-[2-alkoxyalkyl($C_{3-15}$)carbonyloxyethyl]phenyl 4'-[alkyl($C_{3-20}$)oxy]biphenylcarboxylate,
4-[alkoxyalkyl($C_{3-15}$)carbonyloxymethyl]phenyl 4'-[alkyl($C_{3-20}$)]biphenylcarboxylate,
4-[2-alkoxyalkyl($C_{3-15}$)carbonyloxyethyl]phenyl 4'-[alkyl($C_{3-20}$)]biphenylcarboxylate,
4-[alkoxyalkyl($C_{3-15}$)carbonyloxymethyl]phenyl 4-[alkyl($C_{3-20}$)oxycarbonyl]phenylcarboxylate, 4-[2-alkoxyalkyl($C_{3-15}$)carbonyloxyethyl]phenyl 4-[alkyl($C_{3-20}$)oxycarbonyl]phenylcarboxylate, 4-[alkoxyalkyl($C_{3-15}$)carbonyloxymethyl]phenyl 4'-[alkyl($C_{3-20}$)oxycarbonyl]biphenylcarboxylate, 4-[2-alkoxyalkyl($C_{3-15}$)carbonyloxyethyl]phenyl 4-[alkyl($C_{3-20}$)oxycarbonyl]biphenylcarboxylate, 4-[alkoxyalkyl($C_{3-15}$)carbonyloxymethyl]phenyl 4-[alkyl($C_{3-20}$)carbonyloxy]phenylcarboxylate, 4-[2-alkoxyalkyl($C_{3-15}$)carbonyloxyethyl]phenyl 4-[alkyl($C_{3-20}$)carbonyloxy]phenylcarboxylate, 4-[alkoxyalkyl($C_{3-15}$)carbonyloxymethyl]phenyl 4'-[alkyl($C_{3-20}$)carbonyloxy]biphenylcarboxylate, 4-[2-alkoxyalkyl($C_{3-15}$)carbonyloxyethyl]phenyl 4'-[alkyl($C_{3-20}$)carbonyloxy]biphenylcarboxylate, 4-[3-alkoxyalkyl($C_{3-15}$)oxypropyl]phenyl 4-[alkyl($C_{3-20}$)oxycarbonyl]phenylcarboxylate, 4-[4-alkoxyalkyl($C_{3-15}$)oxybutyl]phenyl 4-[alkyl($C_{3-20}$)oxycarbonyl]phenylcarboxylate, 4-[alkoxyalkyl($C_{3-15}$)oxypentyl]phenyl 4-[alkyl($C_{3-20}$)oxycarbonyl]phenylcarboxylate, 4-[6-alkoxyalkyl($C_{3-15}$)oxyhexyl]phenyl 4-[alkyl($C_{3-20}$)oxycarbonyl]phenylcarboxylate, 4-[3-alkoxyalkyl($C_{3-15}$)oxypropyl]phenyl 4'-[alkyl($C_{3-20}$)oxycarbonyl]biphenylcarboxylate, 4-[4-alkoxyalkyl($C_{3-15}$)oxybutyl]phenyl 4'-[alkyl($C_{3-20}$)oxycarbonyl]biphenylcarboxylate, 4-[5-alkoxyalkyl($C_{3-15}$)oxypentyl]phenyl 4'-[alkyl($C_{3-20}$)oxycarbonyl]biphenylcarboxylate, 4-[6-alkoxyalkyl($C_{3-15}$)oxyhexyl]phenyl 4'-[alkyl($C_{3-20}$)oxycarbonyl]biphenylcarboxylate, 4-[3-alkoxyalkyl($C_{3-15}$)oxypropyl]benzoic acid 4-[alkyl($C_{3-20}$)carbonyloxy]phenyl ester, 4-[4-alkoxyalkyl($C_{3-15}$)oxybutyl]benzoic acid 4-[alkyl($C_{3-20}$)carbonyloxyphenyl ester, 4-[5-alkoxyalkyl($C_{3-15}$)oxypentyl]benzoic acid 4-[alkyl($C_{3-20}$)carbonyloxy]phenyl ester, 4-[6-alkoxyalkyl($C_{3-15}$)oxyhexyl]benzoic acid 4-[alkyl($C_{3-20}$)carbonyloxy]phenyl ester, 4-[3-alkoxyalkyl($C_{3-15}$)oxypropyl]benzoic acid 4'-[alkyl($C_{3-20}$)carbonyloxy]biphenylyl ester, 4-[4-alkoxyalkyl($C_{3-15}$)oxybutyl]benzoic acid 4'-[alkyl($C_{3-20}$)carbonyloxy]biphenylyl ester, 4-[5-alkoxyalkyl($C_{3-15}$)oxypentyl]benzoic acid 4'-[alkyl($C_{3-20}$)carbonyloxy]biphenylyl ester, 4-[6-alkoxyalkyl($C_{3-15}$)oxyhexyl]benzoic acid 4'-[alkyl($C_{3-20}$)carbonyloxy]biphenylyl ester, 4-[3-alkoxyalkyl($C_{3-15}$)oxypropyl]phenyl 4-[alkyl($C_{3-20}$)carbonyloxy]phenylcarboxylate, 4-[4-alkoxyalkyl($C_{3-15}$)oxybutyl]phenyl 4-[alkyl($C_{3-20}$)carbonyloxy]phenylcarboxylate, 4-[5-alkoxyalkyl($C_{3-15}$)oxypentyl]phenyl 4-[alkyl($C_{3-20}$)carbonyloxy]phenylcarboxylate, 4-[6-alkoxyalkyl($C_{3-15}$)oxyhexyl]phenyl 4-[alkyl($C_{3-20}$)carbonyloxy]]phenylcarboxylate, 4-[3-alkoxyalkyl($C_{3-15}$)oxypropyl]phenyl 4'-[alkyl($C_{3-20}$)carbonyloxy]biphenylcarboxylate, 4-[4-alkoxyalkyl($C_{3-15}$)oxybutyl]phenyl 4'-[alkyl($C_{3-20}$)carbonyloxy]biphenylcarboxylate, 4-[5-alkoxyalkyl($C_{3-15}$)oxypentyl]phenyl 4'-[alkyl($C_{3-20}$)carbonyloxy]biphenylcarboxylate, 4-[6-alkoxyalkyl($C_{3-15}$)oxyhexyl]phenyl 4'-[alkyl($C_{3-20}$)carbonyloxy]biphenylcarboxylate, 4-[3-alkyl($C_{3-15}$)carbonyloxypropyl]phenyl 4-[alkyl($C_{3-20}$)oxycarbonyl]phenylcarboxylate, 4-[4-alkyl($C_{3-15}$)carbonyloxybutyl]phenyl 4-[alkyl($C_{3-20}$)oxycarbonyl]phenylcarboxylate, 4-[5-alkyl($C_{3-15}$)carbonyloxypentyl]phenyl 4-[alkyl($C_{3-20}$)oxycarbonyl]phenylcarboxylate, 4-[6-alkyl($C_{3-15}$)carbonyloxyhexyl]phenyl 4-[alkyl($C_{3-20}$)oxycarbonyl]phenylcarboxylate, 4-[3-alkyl($C_{3-15}$)carbonyloxypropyl]phenyl 4'-[alkyl($C_{3-20}$)oxycarbonyl]biphenylcarboxylate, 4-[4-alkyl($C_{3-15}$)carbonyloxybutyl]phenyl 4'-[alkyl($C_{3-20}$)oxycarbonyl]biphenylcarboxylate, 4-[5-alkyl($C_{3-15}$)carbonyloxypentyl]phenyl 4'-[alkyl($C_{3-20}$)oxycarbonylbiphenylcarboxylate, 4-[6-alkyl($C_{3-15}$)carbonyloxyhexyl]phenyl 4'-[alkyl($C_{3-20}$)oxycarbonyl]biphenylcarboxylate, 4-[3-alkyl($C_{3-15}$)carbonyloxypropyl]benzoic acid 4-[alkyl($C3020$)carbonyloxy]phenyl ester, 4-[4-alkyl($C_{3-15}$)carbonyloxybutyl]benzoic acid 4-[alkyl($C_{3-20}$)carbonyloxy]phenyl ester, 4-[5-alkyl($C_{3-15}$)carbonyloxypentyl]benzoic acid 4-[alkyl($C_{3-20}$)carbonyloxy]phenyl ester, 4-[6-alkyl($C_{3-15}$)carbonyloxyhexyl]benzoic acid 4-[alkyl($C_{3-20}$)carbonyloxy]phenyl ester, 4-[alkyl($C_{3-15}$)carbonyloxypropyl]benzoic acid 4'-[alkyl($C_{3-20}$)carbonyloxy]biphenylyl ester, 4-[4-alkyl($C_{3-15}$)carbonyloxybytyl]benzoic acid 4'-[alkyl($C_{3-20}$)carbonyloxy]biphenylyl ester, 4-[5-alkyl($C_{3-15}$)carbonyloxypentyl]benzoic acid 4'-[alkyl($C_{3-20}$)carbonyloxy]biphenylyl ester, 4-[6-alkyl($C_{3-15}$)carbonyloxyhexyl]benzoic acid 4'-[alkyl($C_{3-20}$)carbonyloxy]biphenylyl ester, 4-[3-alkyl($C_{3-15}$)carbonyloxypropyl]phenyl 4-[alkyl($C_{3-20}$)carbonyloxy]phenylcarboxylate, 4-[4-alkyl($C_{3-15}$)carbonyloxybytyl]phenyl 4-[alkyl($C_{3-20}$)carbonyloxy]phenylcarboxylate, 4-[5-alkyl($C_{3-15}$)carbonyloxypentyl]phenyl 4-[alkyl($C_{3-20}$)carbonyloxy]phenylcarboxylate, 4-[6-alkyl($C_{3-15}$)carbonyloxyhexyl]phenyl 4-[alkyl($C_{3-20}$)carbonyloxy]phenylcarboxylate, 4-[3-alkyl($C_{3-15}$)carbonyloxypropyl]phenyl 4'-[alkyl($C_{3-20}$)carbonyloxy]biphenylcarboxylate, 4-[4-alkyl($C_{3-15}$)carbonyloxybutyl]phenyl 4'-[alkyl($C_{3-20}$)carbonyloxy]biphenylcarboxylate, 4-[5-alkyl($C_{3-15}$)carbonyloxypentyl]phenyl 4'-[alkyl($C_{3-20}$)carbonyloxy]biphenylcarboxylate, 4-[6-alkyl($C_{3-15}$)carbonyloxyhexyl]phenyl 4'-[alkyl($C_{3-20}$)carbonyloxy]biphenylcarboxylate, 4-[3-alkoxyalkyl($C_{3-15}$)carbonyloxypropyl]phenyl 4-[alkyl($C_{3-20}$)oxycarbonyl]phenylcarboxylate, 4-[4-alkoxyalkyl($C_{3-15}$)carbonyloxybutyl]phenyl 4-[alkyl($C_{3-20}$)oxycarbonyl]phenylcarboxylate, 4-[5-alkoxyalkyl($C_{3-15}$)carbonyloxypentyl]phenyl 4-[alkyl($C_{3-20}$)oxycarbonyl]phenylcarboxylate, 4-[6-alkoxyalkyl($C_{3-15}$)carbonyloxyhexyl]phenyl 4-[alkyl($C_{3-20}$)oxycarbonyl]phenylcarboxylate, 4-[3-alkoxyalkyl($C_{3-15}$)carbonyloxypropyl]phenyl 4'-alkyl($C_{3-20}$)oxycarbonyl]biphenylcarboxylate, 4-[4-alkoxyalkyl($C_{3-15}$)carbonyloxybutyl]phenyl 4'-[alkyl($C_{3-20}$)oxycarbonyl]biphenylcarboxylate, 4-[5-alkoxyalkyl($C_{3-15}$)carbonyloxypentyl]phenyl 4'-[alkyl($C_{3-20}$)oxycarbonyl]biphenylcarboxylate, 4-[6-alkoxyalkyl($C_{3-15}$)carbonyloxyhexyl]phenyl 4'-[alkyl($C_{3-20}$)oxycarbonyl]biphenylcarboxylate, 4-[3-alkoxyalkyl($C_{3-15}$)carbonyloxypropyl]benzoic acid 4-[alkyl($C_{3-20}$)carbonyloxy]phenyl ester, 4-[4-alkoxyalkyl($C_{3-15}$)carbonyloxybutyl]benzoic acid 4-[alkyl($C_{3-20}$)carbonyloxy]phenyl ester, 4-[5-alkoxyalkyl($C_{3-15}$)carbonyloxypentyl]benzoic acid 4-[alkyl($C_{3-20}$)carbonyloxy]phenyl ester, 4-[6-alkoxyalkyl($C_{3-15}$)carbonyloxyhexyl]benzoic acid 4-[alkyl($C_{3-20}$)carbonyloxy]phenyl ester, 4-[3-alkoxyalkyl($C_{3-15}$)carbonyloxypropyl]benzoic acid 4'-[alkyl($C_{3-20}$)carbonyloxy]biphenylyl ester, 4-[4-alkoxyalkyl($C_{3-15}$)carbonyloxybutyl]benzoic acid 4'-[alkyl($C_{3-20}$)carbonyloxy]biphenylyl ester, 4-[5-alkoxyalkyl($C_{3-15}$)carbonyloxypentyl]benzoic acid 4'-[alkyl($C_{3-20}$)carbonyloxy]biphenylyl ester, 4-[6-alkoxyalkyl($C_{3-15}$)carbonyloxyhexyl]benzoic acid 4'-[alkyl($C_{3-20}$)carbonyloxy]biphenylyl ester, 4-[3-alkoxyalkyl($C_{3-15}$)carbonyloxypropyl]phenyl 4-[alkyl($C_{3-20}$)carbonyloxy]phenylcarboxylate, 4-[4-alkoxyalkyl($C_{3-15}$)carbonyloxybutyl]phenyl 4-[alkyl($C_{3-20}$)carbonyloxy]phenylcarboxylate, 4-[5-alkoxyalkyl($C_{3-15}$)carbonyloxypentyl]phenyl 4-[alkyl($C_{3-20}$)carbonyloxy]phenylcarboxylate, 4-[6-alkoxyalkyl($C_{3-15}$)carbonyloxyhexyl]phenyl 4-[alkyl($C_{3-20}$)carbonyloxy]phenylcarboxylate, 4-[3-alkoxyalkyl($C_{3-15}$)carbonyloxypropyl]phenyl 4'-[alkyl($C_{3-20}$)carbonyloxy]biphenylcarboxylate, 4-[4-alkoxyalkyl($C_{3-15}$)carbonyloxybutyl]phenyl 4'-[alkyl($C_{3-20}$)carbonyloxy]biphenylcarboxylate, 4-[5-alkoxyalkyl($C_{3-15}$)carbonyloxypentyl]phenyl 4'-[alkyl($C_{3-20}$)carbonyloxy]biphenylcarboxylate, 4-[6-alkoxyalkyl($C_{3-15}$)carbonyloxyhexyl]phenyl 4'-[alkyl($C_{3-20}$)carbonyloxy]biphenylcarboxylate, 4-[3-alkyl($C_{3-15}$)oxypropyl]phenyl 4-[alkyl($C_{3-20}$)oxycarbonyl]phenylcarboxylate, 4-[4-alkyl($C_{3-15}$)oxybutyl]phenyl 4-[alkyl($C_{3-20}$)oxycarbonyl]phenylcarboxylate, 4-[5-alkyl($C_{3-15}$)oxypentyl]phenyl 4-[alkyl($C_{3-20}$)oxycarbonyl]phenylcarboxylate, 4-[6-alkyl($C_{3-15}$)oxyhexyl]phenyl 4-[alkyl($C_{3-20}$)oxycarbonyl]phenylcarboxylate, 4-[3-alkyl($C_{3-15}$)oxypropyl]phenyl 4'-alkyl($C_{3-20}$)oxycarbonyl]biphenylcarboxylate, 4-[alkyl($C_{3-15}$)oxybutyl]phenyl 4'-[alkyl($C_{3-20}$)oxycarbonyl]biphenylcarboxylate, 4-[5-alkyl($C_{3-15}$)oxypentyl]phenyl 4'-[alkyl($C_{3-20}$)oxycarbonyl]biphenylcarboxylate, 4-[6-alkyl($C_{3-15}$)oxyhexyl]phenyl 4'-[alkyl($C_{3-20}$)oxycarbonyl]biphenylcarboxylate, 4-[3-alkyl($C_{3-15}$)oxypropyl]benzoic acid 4-[alkyl($C_{3-20}$)carbonyloxy]phenyl ester, 4-[4-alkyl($C_{3-15}$)oxybutyl]benzoic acid 4-[alkyl($C_{3-20}$)carbonyloxy]phenyl ester, 4-[5-alkyl($C_{3-15}$)oxypentyl]benzoic acid 4-[alkyl($C_{3-20}$)carbonyloxy]phenyl ester, 4-[6-alkyl($C_{3-15}$)oxyhexyl]benzoic acid 4-[alkyl($C_{3-20}$)carbonyloxy]phenyl ester, 4-[3-alkyl($C_{3-15}$)oxypropyl]benzoic acid 4'-[alkyl($C_{3-20}$)carbonyloxy]biphenylyl ester, 4-[4-alkyl($C_{3-15}$)oxybutyl]benzoic acid 4'-[alkyl($C_{3-20}$)carbonyloxy]biphenylyl ester, 4-[5-alkyl($C_{3-15}$)oxypentyl]benzoic acid 4'-[alkyl($C_{3-20}$)carbonyloxy]biphenyl ester, 4-[6-alkyl($C_{3-15}$)oxyhexyl]benzoic acid 4'-[alkyl($C_{3-20}$)carbonyloxy]biphenylyl ester, 4-[3-alkyl($C_{3-15}$)oxypropyl]phenyl 4-[alkyl($C_{3-20}$)carbonyloxy]phenylcarboxylate, 4-[4-alkyl($C_{3-15}$)oxybutyl]phenyl 4-alkyl($C_{3-20}$)carbonyloxy]phenylcarboxylate, 4-[5-alkyl($C_{3-15}$)oxypentyl]phenyl 4-[alkyl($C_{3-20}$)carbonyloxy]phenylcarboxylate, 4-[6-alkyl($C_{3-15}$)oxyhexyl]phenyl 4-[alkyl($C_{3-20}$)carbonyloxy]phenylcarboxylate, 4-[3-alkyl($C_{3-15}$)oxypropyl]phenyl 4'-alkyl($C_{3-20}$)carbonyloxy]biphenylcarboxylate, 4-[alkyl($C_{3-15}$)oxybutyl]phenyl 4'-[alkyl($C_{3-20}$)carbonyloxy]biphenylcarboxylate, 4-[5-alkyl($C_{3-15}$)oxypentyl]phenyl 4'-[alkyl($C_{3-20}$)carbonyloxy]biphenylcarboxylate, 4-[6-alkyl($C_{3-15}$)oxyhexyl]phenyl 4'-[alkyl($C_{3-20}$)carbonyloxy]biphenylcarboxylate.

In the above examples, the alkyl or the alkoxyalkyl (of 3 to 15 carbon atoms or 3 to 20 carbon atoms) is as exemplified hereinbefore.

Optically active ester derivatives represented by the formula (I) (X is —OCO— or —COO—) are obtained by the two processes explained above. When these derivatives are used as constituting elements of liquid crystal, especially as constituting elements of ferroelectric liquid crystal and when practical optical stability is taken into consideration, substituent $R_2$ in the formula (I) is preferably an alkyl group containing no halogen atom and furthermore, mention may be made of the compounds of X=—COO— and n=3 or more as those which exhibit more preferred properties in practical use.

Furthermore, in order to exhibit high-speed responsiveness which is a characteristic of ferroelectric liquid crystal, liquid crystalline compounds of low viscosity coefficient are desired and in case of the compounds represented by the formula (I), those of l=1 are especially preferred. Compounds of l=2 are wide in temperature range at which Sc* phase is formed and Sc* phase of liquid crystal composition can be widened by using these compounds as one component of liquid crystal composition.

The liquid crystal composition of the present invention contains at least one optically active compound represented by the formula (I) as a component. In this case, it is preferred to use the optically active ester derivative represented by the formula (I) in an amount of 0.1 to 99.9% by weight, especially preferably 1 to 99% by weight of the resulting liquid crystal composition.

Such liquid crystal composition can be effectively utilized as liquid crystal elements, especially light switching element and in this case, the liquid crystal composition can be used according to conventional methods as they are and the methods of use are not critical.

Thus, according to the present invention, the novel optically active ester derivatives represented by the formula (I) can be easily obtained in high yields and besides these derivatives have very excellent properties as liquid crystal compounds and can be effectively utilized as liquid crystal elements.

PREPARATION EXAMPLE 1

Starting materials

In a four-necked flask equipped with a thermometer and a stirrer were charged 4.85 g (20 mmols) of 1-benzyloxy-4-(3-hydroxypropyl)benzene, 2.45 g (24 mmoles) of 2S-methylbutanoic acid and 50 ml of dichloromethane and to the mixture were further added 4.95 g (24 mmols) of N,N'-dicyclohexylcarbodiimide and 20 mg of 4-pyrrolidinopyridine, followed by stirring at room temperature for 24 hours.

After completion of the reaction, the reaction mixture was filtered and the resulting filtrate was washed with 5% acetic acid, water, 5% aqueous sodium bicarbonate solution and saturated aqueous sodium chloride solution in succession, dried over anhydrous magnesium sulfate and then concentrated under reduced pressure. The resulting residue was silica gel column chromatographed (eluent: toluene/ethyl acetate=40/1) to obtain 5.55 g of 1-benzoyl-4-(3-(2S-methylbutanoyloxy)propyl)benzene (VII-1) (yield 85%, $[\alpha]_D^{20} = +7.6°$ (c=1, CHCl$_3$), $n_D^{20} = 1.5331$)

3.26 g (10 mmols) of the obtained (VII-1) was dissolved in 80 ml of ethanol and 0.3 g of 10% Pd/C was added to the solution, followed by vigorous stirring for 12 hours under a hydrogen pressure of 1 to 1.2 atm.

After completion of the reaction, Pd/C was filtered off and the resulting filtrate was concentrated under reduced pressure. The resulting residue was silica gel column chromatographed (eluent: toluene/ethyl acetate=10/1) to obtain 2.24 g (yield 95%) of 4-(3-2S-methylbutanoyloxy)propyl)phenol (V-1): $[\alpha]_D^{20} = +32.3°$ (c=1, CHCl$_3$), $n_D^{20} = 1.5058$.

PREPARATION EXAMPLES 2-5

Starting materials

Reaction, aftertreatment and purification were carried out in the same manner as in Preparation Example 1 except that optically active aliphatic carboxylic acids (XIX) as shown in Table (i) were used in place of 2S-methylbutanoic acid. The results are shown in Table (i).

was used in place of 1-benzyloxy-4-(3-hydroxypropyl)-benzene to obtain 5.50 g (yield 88%) of 1-benzyloxy-4-(2-(2S-methylbutanoyl)ethyl)benzene (VII-6).
$[\alpha]_D^{20} = +8.2°$ (c=1, CHCl$_3$),
$n_D^{20} = 1.5340$.

Further, reaction, aftertreatment and purification were carried out in the same manner as in Preparation Example 1 except that the above obtained (VII-6) was used in place of (VII-1) to obtain 2.18 g (yield 98%) of 4-(2-(2S-methylbutanoyloxy)ethyl)phenol (V-6).
$[\alpha]_D^{20} = +33.8°$ (c=1, CHCl$_3$),
$n_D^{20}$ 1.5066.

PREPARATION EXAMPLES 7-8

Starting materials

Reaction, aftertreatment and purification were carried out in the same manner as in Preparation Example 6 except that optically active aliphatic carboxylic acids (XIX) as shown in Table (ii) were used in place of 2S-methylbutanoic acid. The results are shown in Table (ii).

TABLE (ii)

| Preparation Example | Optically active aliphatic carboxylic acid (XIX) | | Optically active benzyloxy phenyl compound (VII) | | Optically active phenols (V) | |
|---|---|---|---|---|---|---|
| | Name | Amount | Name | Yield and properties | Name | Yield and properties |
| 7 | 4S-propoxy-propionic acid | 3.17 g (24 mmol) | 1-benzyloxy-4-(2-(2S-propoxy-propanoyl)-ethyl)benzene (VII-7) | 5.96 g (87%) $[\alpha]_D^{20} +6.1°$ (c = 1, CHCl$_3$) $n_D^{20}$ 1.5281 | 4-(2-(2S-propoxy-propanoyl)ethyl)-phenole (V-7) | 2.40 g (95%) $[\alpha]_D^{20} +19.6°$ (c = 1, CHCl$_3$) $n_D^{20}$ 1.5063 |
| 8 | 2S-chloro-3S-methyl-pentanoic acid | 3.61 g (24 mmol) | 1-benzyloxy-4-(2-(2S-chloro-3S-methyl-pentanoyl)-ethyl)benzene (VII-8) | 6.21 g (86%) $[\alpha]_D^{20} -4.0°$ (c = 1, CHCl$_3$) $n_D^{20}$ 1.5382 | 4-(2-(2S-chloro-3S-methyl-pentanoyl)ethyl)-phenole (V-8) | 2.46 g (91%) $[\alpha]_D^{20} -8.1°$ (c = 1, CHCl$_3$) $n_D^{20}$ 1.5178 |

TABLE (i)

| Preparation Example | Optically active aliphatic carboxylic acid (XIX) | | Optically active benzyloxy phenyl compound (VII) | | Optically active phenols (V) | |
|---|---|---|---|---|---|---|
| | Name | Amount | Name | Yield and properties | Name | Yield and properties |
| 2 | 4S-methyl-hexanoic acid | 3.12 g (24 mmol) | 1-benzoyl-4-(3-(4S-methyl-hexanoyl)-propyl)benzene (VII-2) | 5.88 g (83%) $[\alpha]_D^{20} +6.2°$ (c = 1, CHCl$_3$) $n_D^{20}$ 1.5248 | 4-(3-(4S-methyl-hexanoyl)-propyl)-phenole (V-2) | 2.56 g (97%) $[\alpha]_D^{20} +22.3°$ (c = 1, CHCl$_3$) $n_D^{20}$ 1.5034 |
| 3 | 2S-propoxy-propionic acid | 3.17 g (24 mmol) | 1-benzyloxy-4-(3-(2S-propoxy-propanoyl)-propyl)benzene (VII-3) | 6.27 g (88%) $[\alpha]_D^{20} +5.9°$ (c = 1, CHCl$_3$) $n_D^{20}$ 1.5260 | 4-(3-(2S-propoxy-propanoyl)-propyl)-phenole (V-3) | 2.56 g (96%) $[\alpha]_D^{20} +18.7°$ (c = 1, CHCl$_3$) $n_D^{20}$ 1.5046 |
| 4 | 2S-octyloxy-propionic acid | 4.86 g (24 mmol) | 1-benzyloxy-4-(3-(2S-octyloxy-propanoyl)-propyl)benzene (VII-4) | 7.00 g (82%) $[\alpha]_D^{20} +4.3°$ (c = 1, CHCl$_3$) $n_D^{20}$ 1.5204 | 4-(3-(2S-octyloxy-propanoyl)-propyl)-phenole (V-4) | 3.16 g (94%) $[\alpha]_D^{20} +11.8°$ (c = 1, CHCl$_3$) $n_D^{20}$ 1.5018 |
| 5 | 2S-chloro-3S-methyl-pentanoic acid | 3.61 g (24 mmol) | 1-benzyloxy-4-(3-(2S-chloro-3S-methyl-pentanoyl)-propyl)benzene (VII-5) | 6.00 g (80%) $[\alpha]_D^{20} -3.8°$ (c = 1, CHCl$_3$) $n_D^{20}$ 1.5372 | 4-(3-(2S-chloro-3S-methyl-pentanoyl)propyl)phenol (V-5) | 3.62 g (92%) $[\alpha]_D^{20} -7.9°$ (c = 1, CHCl$_3$) $n_D^{20}$ 1.5188 |

PREPARATION EXAMPLE 6

Starting materials

Reaction, aftertreatment and purification were carried out in the same manner as in Preparation Example 1 except that 1-benzyloxy-4-(2-hydroxyethyl)benzene

PREPARATION EXAMPLE 9

Starting materials

Reaction, aftertreatment and purification were carried out in the same manner as in Preparation Example 1 except that 1-benzoyl-4-(4-hyxroxybutyl)benzene was used in place of 1-benzyloxy-4-(3-hydroxypropyl)benzene to obtain 5.72 g (yield 84%) of 1-benzyloxy-4-(4-(2S-methylbutanoyl)butyl)benzene (VII-9).

$[\alpha]_D^{20} = +7.1°$ (c=1, CHCl$_3$), $n_D^{20} = 1.5322$.

Further, reaction, aftertreatment and purification were carried out in the same manner as in Preparation Example 1 except that the above obtained (VII-9) was used in place of (VII-1) to obtain 2.40 g (yield 96%) of 4-(4-(2S-methylbutanoyloxy)butyl)phenol (V-9).

$[\alpha]_D^{20} = +29.8°$ (c=1, CHCl$_3$), $n_D^{20} = 1.5049$.

PREPARATION EXAMPLES 10-11

Starting materials

Reaction, aftertreatment and purification were carried out in the same manner as in Preparation Example 9 except that optically active aliphatic carboxylic acids (XIX) as shown in Table (iii) were used in place of 2S-methylbutanoic acid. The results are shown in Table (iii).

for 1 hour and additionally for 2 hours at 20° C. Then, thereto was added 12.1 g (0.05 mol) of 2S-methylbutyl tosylate at 15°-25° C. over a period of 30 minutes and this was kept at that temperature for 30 minutes and then for 2 hours at 30°-35° C. After completion of the reaction, the reaction mixture was poured into ice water and extracted with 60 ml of ethyl acetate. The organic layer was separated, washed with water and concentrated under reduced pressure and purified by column chromatography using toluene to obtain 7.30 g (yield 65%) of 4-{2-(2S-methylbutoxy)ethyl}acetophenone (VI-12).

$[\alpha]_D^{20} = 4.5°$ (c=1, CHCl$_3$), $n_D^{20} = 1.5118$.

Then, 2.34 g (0.01 mol) of the obtained (VI-12), 3.44 g (0.02 mol) of meta-chloroperbenzoic acid and 20 ml of dichloromethane were charged in the flask and reaction was allowed to proceed at 20°-30° C. for 24 hours. The moment at which the starting material (VI-12) disappeared was taken as a reaction end and reaction was completed.

TABLE (iii)

| Preparation Example | Optically active aliphatic carboxylic acid (XIX) | | Optically active benzyloxy phenyl compound (VII) | | Optically active phenols (V) | |
|---|---|---|---|---|---|---|
| | Name | Amount | Name | Yield and properties | Name | Yield and properties |
| 10 | 2S-propoxy-propionic acid | 3.17 g (24 mmol) | 1-benzyloxy-4-(4-(2S-propoxy-propanoyl)-butyl)benzene (VII-10) | 6.15 g (83%) $[\alpha]_D^{20}$ +5.5° (c = 1, CHCl$_3$) $n_D^{20}$ 1.5249 | 4-(4-(2S-propoxy-propanoyl)butyl)-phenole (V-10) | 2.69 g (96%) $[\alpha]_D^{20}$ +17.6° (c = 1, CHCl$_3$) $n_D^{20}$ 1.5044 |
| 11 | 2S-chloro-3S-methyl-pentanoic acid | 3.61 g (24 mmol) | 1-benzyloxy-4-(4-(2S-chloro-3S-methyl-pentanoyl)-butyl)benzene (VII-11) | 6.61 g (85%) $[\alpha]_D^{20}$ −3.1° (c = 1, CHCl$_3$) $n_D^{20}$ 1.5320 | 4-(4-(2S-chloro-3S-methyl-pentanoyl)butyl)-phenole (V-11) | 2.69 g (90%) $[\alpha]_D^{20}$ −7.2° (c = 1, CHCl$_3$) $n_D^{20}$ 1.5143 |

PREPARATION EXAMPLE 12

Starting materials 84.0 g (0.63 mol) of aluminum chloride and 400 ml of dichloromethane were charged in a four-necked flask provided with a stirrer and a thermometer and then thereto was added 51.8 g (0.66 mol) of acetyl chloride at 10°-20° C. over a period of 2 hours. This was kept at that temperature for 1 hour and then thereto was added 49.2 g (0.3 mol) of β-phentyl acetate at 10°-25° C. over a period of 3 hours. The content was kept at 20°-30° C. and then was taken out into ice water and 100 ml of dichloromethane was added thereto to separate an organic layer. This organic layer was washed with water, 3% aqueous sodium carbonate solution and water in succession, dried over magnesium sulfate and then concentrated under reduced pressure to obtain 43.0 g (yield 93%) of 4-(β-acetoxyethyl)acetophenone (XVI-12).

51.5 g (0.25 mol) of the resulting 4-(β-acetoxyethyl)acetophenone (XVI-12), 65 g of 20% sodium hydroxide and 150 ml of methanol were charged in the flask and stirred at room temperature for 4 hours. After completion of the reaction, the reaction mixture was poured into water and extracted with 200 ml of toluene. Organic layer separated was washed with water and then concentrated under reduced pressure to obtain 40.6 g (yield 99%) of 4-(β-hydroxyethyl)acetophenone (XV-12).

Subsequently, 7.88 g (0.048 mol) of the resulting (XV-12) and 80° C. Thereto was added 1.16 g (0.048 mol) of sodium hydride and this was kept at that temperature The reaction mixture was washed with 3% sodium carbonate and then with water and then concentrated. The concentrated residue was purified by column chromatography using toluene to obtain 2.25 g (yield 90%) of 4-{2-(2S-methylbutoxy)ethyl}phenylacetate (VIII-12).

$[\alpha]_D^{20} = +3.8°$ (c=1, CHCl$_3$), $n_D^{20} = 1.4982$.

Subsequently, 1.25 g (5 mmols) of the obtained (VIII-12), 1.5 g (7.5 mmols) of 20% sodium hydroxide and 5 ml of methanol were charged in the flask and stirred at room temperature for 4 hours. After completion of the reaction, methanol was distilled off and the residue was rendered weakly acidic with 2N-aqueous hydrochloric acid and extracted with 20 ml of ethyl acetate. The organic layer was washed with water and then concentrated under reduced pressure. The concentrated residue was purified by chromatography using toluene: ethyl acetate=5:1 to obtain 0.92 g (yield 96%) of 4-{2-(2S-methylbutoxy)ethyl}phenol (V-12).

$[\alpha]_D^{20} = +6.1°$ (c=1, CHCl$_3$), $n_D^{20} = 1.5130$.

PREPARATION EXAMPLE 13

Starting materials 7.88 g (0.048 mol) of (XV-12) obtained in Preparation Example 12 and 70 ml of N-methylpyrrolidone were charged in the flask and cooled to 0°-5° C. Thereto was added 1.16 g (0.048 mol) of sodium hydride and this was kept at that temperature for 1 hour and furthermore for 2 hours at 20° C. Then, thereto was added 17.06 g (0.06 mol) of 1R-methylheptyl tosylate at 15°-20° C. over a period of 2 hours and this was kept at that temperature for 1 hour and then for 2 hours at 30°-35° C. After completion of the reaction, the reaction mixture was subjected to aftertreatment and purification as in Preparation Example 12 to obtain 5.96 g (yield 45%) of 4-{-(1S-methylheptyloxy)ethyl}acetophenone (VI-13).

$[\alpha]_D^{20} = +3.8°$ (c=1, CHCl$_3$),
$n_D^{20} = 1.5047$.

Then, 2.76 g (0.01 mol) of the resulting (VI-13), 4.3 g (0.025 mol) of m-perchlorobenzoic acid and 20 ml of dichloroethane were charged in the flask and reaction was allowed to proceed for 20 hours at 20°-30° C. After completion of the reaction, the reaction mixture was washed with 3% sodium carbonate, followed by aftertreatment and purification as in Preparation Example 12, thereby to obtain 2.69 g (yield 92%) of 4-{2-(1S-methylheptyloxy)ethyl}phenylacetate (VIII-13).

$[\alpha]_D^{20} = +3.1°$ (c=1, CHCl$_3$),
$n_D^{20} = 1.4966$.

Thereafter, 1.46 g (5 mmols) of the obtained (VIII-13), 2.1 g (7.5 mmols) of 20% potassium hydroxide, 3 ml of methanol and 1 ml of tetrahydrofuran were stirred at 30° C. for 4 hours. After completion of the reaction, ethanol and tetrahydrofuran were distilled off and the residue was rendered weakly acidic with 2N-aqueous hydrochloric acid, followed by aftertreatment and purification as in Preparation Example 12, thereby to obtain 1.20 g (yield 95.5%) of 4-{2-(1S-methylheptyloxy)ethyl}phenol (V-13). $[\alpha]_D^{20} = +55°$ (c=1, CHCl$_3$),
$n_D^{20} = 1.5102$.

PREPARATION EXAMPLE 14

Starting material 7.88 g (0.048 mole) of the (XV-12) obtained in the Starting-material Preparation Example 12 and 80 ml of dimethylformamide were charged, followed by cooling to 0° to 5° C. After 1.16 g (0.048 mole) of sodium hydride were added thereto and the resulting mixture was maintained at the same temperature for 1 hour, the temperature was raised to room temperature. Subsequently, 16.34 g (0.06 mole) of 2S-propoxypropyl tosylate were added dropwise. The resulting mixture was maintained at room temperature for 1 hour and then at 25° to 30° C. for 3 hours. After completion of the reaction, post-treatment and purification were carried out similarly to in the Starting-material Preparation Example 12, to obtain 6.98 g (yield: 55%) of 4-{2-(2S-propoxypropoxy)ethyl}-acetophenone (VI-14).

$[\alpha]_D^{20} = +4.8°$ (c=1, CHCl$_3$),
$n_D^{20} = 1.5103$.

Next, 2.64 g (0.01 mole) of the VI-14) obtained above, 4.3 g (0.025 mole) of methachloroperbenzoic acid and 20 ml of 1,2-dichloroethane were charged, followed by stirring at 20° to 30° C. for 15 hours. After completion of the reaction, post-treatment and purification were carried out similarly to in the Starting-material Preparation Example 12, to obtain 2.61 g (yield: 93%) of 4-{2-(2S-propoxypropoxy)ethyl}phenyl acetate (VIII-14).

$[\alpha]_D^{20} = +4.2°$ (c=1, CHCl$_3$),
$n_D^{20} = 1.4938$.

Next, 1.40 g (5 milimole) of the (VIII-14) obtained above, 2.1 g (7.5 milimole) of 20% potassium hydroxide and 5 ml of methanol were stirred at room temperature for 3 hours. After completion of the reaction, the methanol was distilled off and post-treatment and purification were carried out similarly to in the Starting-material Preparation Example 12, to obtain 1.17 g (yield: 98%) of 4-{2-(2S-propoxypropoxy)ethyl}phenol (V-14).

$[\alpha]_D^{20} = +7.3°$ (c=1, CHCl$_3$),
$n_D^{20} = 1.5087$.

PREPARATION EXAMPLE 15

Starting material

Into an apparatus similar to in the Starting-material Preparation Example 12, 84.0 g (0.63 mole) of aluminum chloride and 450 ml of dichloromethane were charged, followed by adding 51.8 g (0.66 mole) of acetyl chloride at 10° to 15° C. over 2 hours. After maintained at the same temperature for 1 hour, 53.4 g (0.3 mole) of 3-phenylpropyl acetate were added thereto at 10° to 20° C. over 3 hours. After maintained at 25° C. for 4 hours, the reaction mixture was poured into ice-water, followed by addition of 100 ml of dichloromethane to separate the organic phase. The organic phase was washed subsequently with water, 3% aqueous sodium carbonate solution and water. The organic phase was dried over magnesium sulfate and then concentrated under reduced pressure to obtain 62.4 g (yield: 94.5%) of 4-(3-acetoxypropyl)acetophenone (XVI-15)

55.0 g (0.25 mole) of the (XVI-15) obtained above, 65 g of 10% potassium hydroxide, 20 ml of tetrahydrofuran and 60 ml of methanol were charged, followed by stirring at room temperature for 5 hours. After completion of the reaction, the reaction mixture was concentrated under reduced pressure to distill the tetrahydrofuran and methanol off. The residue was extracted with toluene. The organic phase was further washed with water and then concentrated under reduced pressure to obtain 43.9 g (yield: 98.5%) of 4-(3-hydroxypropyl)acetophenone (XV-15).

Next, 8.54 g (0–48 mole) of the XV-15) obtained above and 80 ml of dimethylformamide were charged, followed by cooling to 0° to 5° C. After 1.16 g (0.048 mole) of sodium hydride were added thereto, the resulting mixture was maintained at the same temperature for 1 hour and further at 25° C. for 2 hours. Subsequently, 12.1 g (0.05 mole) of 2S-methylbutyl tosylate were added thereto at 20° to 30° C. over 3 hours. The resulting mixture was maintained at the same temperature for 30 minutes and then at 30° to 40° C. for 2 hours. After completion of the reaction, post-treatment and purification were carried out similarly to in the Starting-material Preparation Example 12, to obtain 8.44 g (yield: 71%) of 4-{3-(2S-methylbutoxy)propyl}acetophenone (VI-15).

$[\alpha]_D^{20} = +3.3°$ (c=1, CHCl$_3$),
$n_D^{20} = 1.5048$.

Next, to a solution of 2.48 g (0.01 mole) of the (VI-15) obtained above and 20 ml of propyl ether, were added 1.14 g of 60% peracetic acid at 20° C. over 2 hours, followed by stirring at 20° to 30° C. for 15 hours. After completion of the reaction, the reaction mixture was washed subsequently with water, 2% aqueous sodium carbonate solution, water, 2% aqueous hydrochloric acid solution and water. Subsequently, similarly to in the Starting-material Preparation Example 12, post-treatment and purification were carried out to obtain 2.44 g (yield: 92.5%) of 4-{3-(2S-methylbutoxy)propyl} phenyl acetate (VIII-15).

$[\alpha]_D^{20} = +2.8°$ (c=1, CHCl$_3$),
$n_D^{20} = 1.4923$.

Next, 1.32 g (5 millimole) of the VIII-15) obtained above, 2 g (0.01 mole) of 20% sodium hydroxide and 0.1 g of tetrabutylammonium bromide were stirred at 30° C. for 10 hours. After completion of the reaction, the reaction mixture was adjusted to weak acidic with 2N-aqueous hydrochloric acid solution and extracted with 20 ml of ethyl acetate. Subsequently, similarly to in the Starting-material Preparation Example 12, post-treatment and purification were carried out to obtain 1.06 g (yield: 95.5%) of 4-{3-(2S-methylbutoxy)propyl}phenol (V-15).

$[\alpha]_D^{20} = +3.5°$ (c=1, CHCl$_3$),
$n_D^{20} = 1.5070$.

PREPARATION EXAMPLE 16

Starting material 8.54 g (0.048 mole) of the (XV-15) obtained in the Starting-material Preparation Example 15, 20 ml of tetrahydrofuran and 60 ml of dimethylformamide were charged, followed by cooling to 0° to 10° C. After 1.28 g (0.052 mole) of sodium hydride were added thereto, the resulting mixture was maintained at the same temperature for 1 hour and further at 20° C. for 2 hours.

Next, 17.06 g (0.06 mole) of 1R-methylheptyl tosylate were added thereto at 15° C. over 3 hours. The resulting mixture was maintained at the same temperature for 1 hour and then at 30° C. for 1 hour. After completion of the reaction, post-treatment and purification were carried out similarly to in the Starting-material Preparation Example 12 to obtain 6.68 g (yield 48%) of 4-{3-(1S-methylheptyloxy)propyl}acetophenone (VI-16).

$[\alpha]_D^{20} = +3.1°$ (c=1, CHCl$_3$),
$n_D^{20} = 1.5020$.

Next, 2.9 g (0.01 mole) of (VI-16) obtained above, 4.3 g (0.025 mole) of methachloroperbenzoic acid and 15 ml of dichloromethane were charged to react with each other at 20° to 30° C. for 24 hours. After completion of the reaction, the reaction mixture was washed subsequently with 3% sodium hydroxide and water. The organic phase was concentrated and then purified by column chromatography to obtain 2.83 g (yield: 92.4%) of 4-{3-(1S-methylheptyloxy)propyl}acetate (VIII-16).

$[\alpha]_D^{20} = +2.8°$ (c=1, CHCl$_3$),
$n_D^{20} = 1.5019$.

Next, 1.53 g (5 millimole) of the (VIII-16) obtained above, 3 g (0.015 mole) of 20% sodium hydroxide and 5 ml of methanol were stirred at 20° to 30° C. for 5 hours. After completion of the reaction, the methanol was distilled off and the residue was adjusted to weak acidic with 2N-aqueous hydrochloric acid solution and extracted with 20 ml of ethyl acetate. The organic phase was washed with water and then concentrated under reduced pressure. The concentrated residue was purified by column chromatography with toluene:ethyl acetate (5:1) to obtain 1.27 g (yield: 96.5%) of 4-{3-(1S-methylheptyl)propyl}phenol (V-16).

$[\alpha]_D^{20} = +4.3°$ (c=1, CHCl$_3$),
$n_D^{20} = 1.5051$.

PREPARATION EXAMPLES 17 to 22

Starting-material

Reaction, post-treatment and purification were carried out similarly to in the Starting-material Preparation Example 16 except that sulfornate shown in Table-(iv) was used in place of 1R-methylheptyltocylate, to obtain the results as shown in Table-(iv).

TABLE (iv)

| Preparation Example (starting material) | Alkylating agent (XI) Name | Amount used | Optically active acetophenone (VI) Name | Yield and Physical properties |
|---|---|---|---|---|
| 17 | 2S-butyl-tosylate | 13.7 g (0.06 mole) | 4-{3-(2R-butoxy)propyl}-acetophenone (VI-17) | 4.5 g (yield 40%) $[\alpha]_D^{20}$ −5.4° $n_D^{20}$ 1.5118 |
| 18 | 4S-methyl-hexyl tosylate | 13.52% (0.05 mole) | 4-{3-(4S-methylhxyloxy)-propyl}aceto-phenone (VI-18) | 8.36 g (yield 63%) $[\alpha]_D^{20}$ +1.5° $n_D^{20}$ 1.4908 |
| 19 | 2S-fluoro-heptyl tosylate | 17.28% (0.06 mole) | 4-{3-(2S-fluoroheptyl)-propyl}aceto-phenone (VI-19) | 6.36 g (yield 45%) $[\alpha]_D^{20}$ −6.2° $n_D^{20}$ 1.5002 |
| 20 | 2S-methoxy-propyl tosylate | 14.66% (0.06 mole) | 4-{3-(2S-methoxypropoxy)-propyl}aceto-phenone (VI-20) | 6.25 g (yield 52%) $[\alpha]_D^{20}$ +6.2° $n_D^{20}$ 1.5108 |
| 21 | 2S-propoxy-propyl tosylate | 16.34% (0.06 mole) | 4-{3-(2S-propoxypropoxy)-propyl}aceto-phenone (VI-21) | 6.41 g (yield 48%) $[\alpha]_D^{20}$ +4.6° $n_D^{20}$ 1.4999 |
| 22 | 2S-octyl-oxypropyl tosylate | 20.55% (0.06 mole) | 4-{3-(2S-octyloxypropoxy)-propyl}aceto-phenone (VI-22) | 6.86 g (yield 41%) $[\alpha]_D^{20}$ +4.0° $n_D^{20}$ 1.4973 |

| Preparation Example (starting material) | Optically active acetoyloxybenzene (VIII) Name | Yield and Physical properties | Optically active phenol (V) Name | Yield and Physical property |
|---|---|---|---|---|
| 17 | 4-{3-(2R-butoxy)propyl}-phenol acetate (VIII-17) | 2.29 g (yield 1.5%) $[\alpha]_D^{20}$ +19.6° $n_D^{20}$ 1.5063 | 4-{3-(2R-butoxy)phenyl}-phenol (V-17) | 1.01 g (yield 97.0%) $[\alpha]_D^{20}$ +19.6° $n_D^{20}$ 1.5076 |
| 18 | 4-{3-(4S-methylhexyloxy)-propyl}phenyl | 2.72 g (yield 93.1%) $[\alpha]_D^{20}$ +1.5° | 4-{3-(4S-methylhexyloxy)-propyl}phenol | 1.22 g (yield 7.5%) $[\alpha]_D^{20}$ +2.3° |

TABLE (iv)-continued

| | | | | |
|---|---|---|---|---|
| | acetate (VIII-18) | $n_D^{20}$ 1.4912 | (V-18) | $n_D^{20}$ 1.5002 |
| 19 | 4-{3-(2S-fluoroheptyloxy)-propyl}phenyl acetate (VIII-19) | 2.81 g (yield 90.4%) $[\alpha]_D^{20}$ −7.2° $n_D^{20}$ 1.4928 | 4-{3-(2S-fluoroheptyloxy)-propyl}phenol (V-19) | 1.27 g (yield 94.5%) $[\alpha]_D^{20}$ −7.3° $n_D^{20}$ 1.5010 |
| 20 | 4-{3-(2S-methoxypropyl)-propyl}phenyl acetate (VIII-20) | 2.50 g (yield 94%) $[\alpha]_D^{20}$ +5.9° $n_D^{20}$ 1.5010 | 4-{3-(2S-methoxypropoxy)-propyl}phenol (V-20) | 1.18 g (yield 98%) $[\alpha]_D^{20}$ +10.1° $n_D^{20}$ 1.5112 |
| 21 | 4-{3-(2S-propoxypropoxy)-propyl}phenyl acetate (VIII-21) | 2.71 g (yield 92%) $[\alpha]_D^{20}$ +3.9° $n_D^{20}$ 1.4927 | 4-{3-(2S-methoxypropoxy)-propyl}phenol (V-21) | 1.30 g (yield 97%) $[\alpha]_D^{20}$ +7.0° $n_D^{20}$ 1.5012 |
| 22 | 4-{3-(2S-propoxypropoxy)-propyl}phenyl acetate (VIII-21) | 3.32 g (yield 91%) $[\alpha]_D^{20}$ +3.6° $n_D^{20}$ 1.4915 | 4-{3-(2S-octyloxypropoxy)-propyl}phenol (V-22) | 1.62 g (yield 96%) $[\alpha]_D^{20}$ +5.6° $n_D^{20}$ 1.5004 |

Optical rotation was each measured under conditions of (c = 1, CHCl₃).

PREPARATION EXAMPLE 23

Starting-material

Similarly to in Preparation Example 12 (starting material), 84.0 g (0.63 mole) of aluminum chloride and 500 ml of dichloroethane were charged, followed by adding 51.8 g (0.66 mole) of acetyl chloride at 10° to 15° C. over 3 hours. After maintained at the same temperature for 1 hour, 57.6 g (0.3 mole) of 4-phenylbutyl acetate were added thereto at 10° to 20° C. over 3 hours. After maintained at 20° to 25° C. for 3 hours, the reaction mixture was poured into ice-water and dichloromethane was added thereto to effect extraction. Subsequently, similarly to in the Preparation Example 12 (starting material), post-treatment and purification were carried out to obtain 59.0 g (yield: 84%) of 4-(4-acetoxybutyl)acetophenone (XVI-23).

58.5 g (0.25 mole) of the (XVI-23) obtained above, 75 g of 20% sodium hydroxide and 150 ml of methanol were charged, followed by stirring at room temperature for 5 hours. Subsequently, similarly to in the Preparation Example 12 (starting material), post-treatment and purification were carried out to obtain 40.8 g (yield: 85%) of 4-(4-hydroxybutyl)acetophenone (XV-23).

Next, 9.22 g (0.048 mole) of the (XV-23) obtained above, 60 ml of dimethylformamide and 15 ml of tetrahydrofuran were charged, followed by cooling to 0° to 5° C. After 1.16 g (0.048 mole) of sodium hydride were added thereto, the resulting mixture was maintained at the same temperature for 1 hour and further at 25° to 30° C. for 2 hours. Subsequently, 12.1 g (0.05 mole) of 2S-methylbutyl tosylate were added at 15° to 25° C. over 3 hours. The reaction mixture was maintained at the same temperature for 1 hour and further at 30° to 35° C. for 2 hours. After completion of the reaction, post-treatment and purification were carried out similarly to in the Preparation Example 12 (starting material), to obtain 8.94 g (yield: 71%) of 4-{4-(2S-methylbutoxy)butyl}acetophenone (VI-23).

$[\alpha]_D^{20}$ = +1.6° (c=1, CHCl₃),
$n_D^{20}$ = 1.5020

Next, 2.62 g (0.01 mole) of the (VI-23) obtained above, 3.44 g (0.02 mole) of metha-chloroperbenzoic acid and 12 ml of ethyl acetate were charged to react with each other at 25° to 35° C. for 20 hours. After completion of the reaction, the reaction mixture was washed subsequently with 3% sodium carbonate and water. The organic phase was concentrated and then purified by column chromatography to obtain 2.52 g (yield: 90.5%) of 4-{4-(2S-methylbutoxy)butyl}phenyl acetate (VIII-23).

$[\alpha]_D^{20}$ = +1.3° (c=1, CHCl₃),
$n_D^{20}$ = 1.4896.

Next, 1.39 g (5 millimole) of the (VIII-23) obtained above, 3 g (0.015 mole) of 20% sodium hydroxide and 3 ml of methanol were stirred at 25° to 30° C. for 5 hours. Subsequently, similarly to in Preparation Example 12 (starting material), post-treatment and purification were carried out to obtain 1.13 g (yield: 95.5%) of 4-{4-(2S-methylbutoxy)butyl}phenol (V-23).

$[\alpha]_D^{20}$ = +2.9° (c=1, CHCl₃),
$n_D^{20}$ = 1.5030.

PREPARATION EXAMPLE 24

Starting material 9.22 g (0.048 mole) of the (XV-23) obtained in Preparation Example 23 (starting material) and 80 ml of dimethylformamide were charged, followed by cooling to 0° to 5° C. After 1.16 g (0.048 mole) of sodium hydride were added thereto and the resulting mixture was maintained at the same temperature for 1 hour, the temperature was raised to room temperature. Subsequently, 16.34 g (0.06 mole) of 2S-propoxypropyl tosylate were added dropwise. The resulting mixture was maintained at room temperature for 1 hour and then at 25° to 30° C. for 3 hours. After completion of the reaction, post-treatment and purification were carried out similarly to in the Preparation Example 12 (starting material), to obtain 8.7 g (yield: 62%) of 4-{4-(2S-propoxypropoxy)butyl}acetophenone (VI-24).

$[\alpha]_D^{20}$ = +4.2° (c=1, CHCl₃),
$n_D^{20}$ = 1.4990.

Next, 2.92 g (0.01 mole) of the (VI-24) obtained above, 4.3 g (0.025 mole) of meta-chloroperbenzoic acid and 20 ml of 1,2-dichloroethane were charged, followed by stirring at 20° to 30° C. for 20 hours. After completion of the reaction, post-treatment and purification were carried out similarly to in the Preparation Example 12 starting material, to obtain 2.84 g (yield: 92%) of 4-{4-(2S-propoxypropoxy)butyl}phenyl acetate (VIII-24).

$[\alpha]_D^{20}$ = +3.8° (c=1, CHCl₃),
$n_D^{20}$ = 1.4927

Next, 1.54 g (5 millimole) of the (VIII-24) obtained above, 3 g (0.015 mole) of 20% sodium hydroxide and 5 ml of methanol were stirred at room temperature for 3 hours. Subsequently, similarly to the Preparation Example 12 (starting material), post-treatment and purification were carried out to obtain 1.38 g (yield: 98%) of 4-{4-(2S-propoxypropoxy)butyl}phenol (V-24).

$[\alpha]_D^{20} = +6.6°$ (c=1, CHCl$_3$),
$n_D^{20} = 1.5080$

PREPARATION EXAMPLE 25

Starting material

Alkylating reaction, post-treatment and purification were carried out similarly to in Preparation Example 15 (starting material) except that 10.88 g (0.072 mol) of 2S-methylbutyl bromide was used in place of 2S{ketyl-butyl tosylatece to obtain 7.62 g (yield 64%) of 4-{3-(2S-methylbutoxy)propyl}acetophenone (VI-25). 2.48 g (0.01 mole) of the (VI-25) obtained above was subjected to oxidizing reaction similarly to in the Preparation Example 15 (starting material) to give 4-{3-(2S-methylbutoxy)phenyl}phenyl acetate (VIII-25). The obtained amount was 2.46 g (yield: 93%).

Further, 1.32 g (5 millimole) of the (VIII-25) mentioned above was subjected to hydrolyzing reaction similarly to the Preparation Example 14 (starting material), to give 4-{3-(2S-methylbutoxy)propyl}phenol (V-25). The obtained amount was 1.06 g (yield: 95.3%).

PREPARATION EXAMPLE 26

Starting material

Into a four necked flask equiped with a stirrer and a thermometer, 84.0 g (0.63 mole) of aluminum chloride and 400 ml of dichloroethane were charged, followed by adding 51.8 g (0.66 mole) of acetyl chloride at 10° to 20° C. over 2 hours. After maintained at the same temperature for 1 hour, 49.2 g (0.3 mole) of β-phenetyl acetate were added thereto at 10° to 25° C. over 3 hours. After maintained at 20° to 30° C., the reaction mixture was poured in to ice-water and 100 ml of dichloromethane was added thereto to separate the organic phase. The organic phase was washed subsequently with water, 3% aqueous sodium carbonate solution and water. The organic phase was dried over magnesium sulfate to obtain "43.0 g (yield 93%) of" 4-(β-acetoxyethyl)acetophenone (XVI-26).

51.5 g (0.25 mole) of the 4-(β-acetoxyethyl)acetophenone (XVI-26) obtained above, 65 g of 20% sodium hydroxide and 150 ml of methanol were charged, followed by stirring at room temperature for 4 hours. After completion of the reaction, the reaction mixture was poured into water to extract with 200 ml of toluene. The organic phase as washed with water and then concentrated under reduced pressure to obtain 40.6 g (yield: 99%) of 4-(β-hydroxyethyl)acetophenone (XV-26).

Next, 7.88 g (0.048 mole) of the (XV-26) obtained above and 80 ml of dimethylformamide were charged, followed by cooling to 0° to 5° C. After 1.16 g (0.048 mole) of sodium hydride were added thereto, the resulting mixture was maintained at the same temperature for 1 hour and further at 20° C. for 2 hours. Subsequently, 12.1 g (0.05 mole) of 2S-methylbutyl tosylate were added at 15° to 25° C. over 2 hours. The reaction mixture was maintained at the same temperature for 30 minutes and further at 30° to 35° C. for 2 hours. After completion of the reaction, the reaction mixture was poured into ice and extracted twice with 60 ml of ethyl acetate. The organic phase was separated, washed with water and concentrated under reduced pressure. The concentrated residue was purified by column chromatography with toluene to obtain 7.30 g (yield: 65%) of 4-{2-(2S-methylbutoxy)ethyl}-acetophenone (VI-26).

$[\alpha]_D^{20} = +4.5°$ (c=1, CHCl$_3$),
$n_D^{20} = 1.5118$.

Next, 2.34 g (0.0o mole) of the (VI-26) obtained above was added at room temperature to a mixed solution previously obtained by adding 11 g (0.07 mole) of bromine to 16 g of 20% aqueous sodium hydroxide solution and further adding 30 ml of dioxane, followed by stirring for 15 hours. After completion of the reaction, the reaction mixture was poured into ice-water, adjusted to weak acidic with 10% sulfuric acid and extracted with 100 ml of ethyl acetate. The organic phase was separated and further washed with water and then concentrated. The concentrated residue was purified by chromatography with toluene-acetic acid (20:1) to obtain 2.1 g (yield: 90%) of 4-{2-(2S-methylbutoxy)ethyl}benzoic acid (III-26).

$[\alpha]_D^{20} = +6.1°$ (c=1, CHCl$_3$),
m.p. 60° to 62° C.

PREPARATION EXAMPLE 27

Starting material 7.88 g (0.048 mole) of the (XV-26) obtained in the Preparation Example 26 (starting material) and 70 ml of N-methylpyrrolidone were charged followed by cooling to 0° to 5° C. After 1.16 g of (0.048 mole) of sodium hydride were added thereto, the resulting mixture was maintained at the same temperature for 1 hour and further at 20° C. for 2 hours. Subsequently, 17.06 g (0.06 mole) of 1R-methylheptyl tosylate were added at 15° to 20° C. over 2 hours. The resulting mixture was maintained at the same temperature for 1 hour and then at 30° to 35° C. for 2 hours. After completion of the reaction, post-treatment and purification were carried out similarly to in the Preparation Example 26 (starting material), to obtain 5.96 g (yield: 45%) of 4-{2-(1S-methylheptyloxy)ethyl}acetophenone (VI-27).

$[\alpha]_D^{20} = +3.8°$ (c=1, CHCl$_3$),
$n_D^{20} = 1.5047$.

Next, 2.76 g (0.01 mole) of the (VI-27) obtained above was added at room temperature to a mixed solution of 16 ml of 20% aqueous sodium hydroxide solution, 11 g (0.07 mole) of bromine and 20 ml of dioxane, followed by stirring for 20 hours. After completion of the reaction, post-treatment and purification were carried out similarly to in the Preparation Example 12 (starting material), to obtain 2.56 g (yield: 92%) of 4-(β-(1S-methylheptyloxy)ethyl)benzoic acid (III-27).

$[\alpha]_D^{20} = +4.9°$ (c=1, CHCl$_3$),
m.p. 41° to 43° C.

PREPARATION EXAMPLE 28

Starting material 7.88 g (0.048 mole) of the (XV-26) obtained in Preparation Example 26 (starting material) and 80 ml of dimethylformamide were charged, followed by cooling to 0° to 5° C. After 1.16 g (0.048 mole) of sodium hydride were added thereto and the resulting mixture was maintained at the same temperature for 1 hour, the temperature was raised to room temperature. Subsequently, 16.34 g (0.06 mole) of 2S-propoxypropyl tosylate were added dropwise. The resulting mixture as maintained at room temperature for 1 hour and then at 25° to 30° C. for 3 hours. After completion of the reaction, post-treatment and purification were carried out similarly to in the Preparation Example 12 (starting material), to obtain 6.98 g (yield: 55%) of 4-{2-(2S-propoxypropoxy)ethyl}acetophenone (VI-28).

$[\alpha]_D^{20} = +4.8°$ (c=1, CHCl$_3$),
$n_D^{20} = 1.5003$.

Next, 2.64 g (0.01 mole) of the (VI-28) obtained above were added at room temperature to a mixed solution of 16 ml of 20% aqueous sodium hydroxide solution, 11 g (0.07 mole) of bromine and 20 ml of dioxane, followed by stirring for 20 hours. After completion of the reaction, post-treatment and purification were carried out similarly to in the Preparation Example 26 (starting-material), to obtain 2.47 g (yield: 93%) of 4-{2-(2S-propoxyproozy)ethyl}benzoic acid (III-28).

$[\alpha]_D^{20} = +6.0°$ (c=1, CHCl$_3$),
m.p. 51° to 52° C.

PREPARATION EXAMPLE 29

Starting material

Into an apparatus similar to in the Preparation Example 26 (starting material), 84.0 g (0.63 mole) of aluminum chloride and 450 ml of dichloromethane were charged followed by adding 51.8 g (0.66 mole) of acetyl chloride at 10° to 15° C. over 2 hours. After maintained at the same temperature for 1 hour, 53.4 g (0.3 mole) of 3-phenylproyl acetate were added thereto 10° to 20° C. over 3 hours. After maintained at 25° C. for 4 hours, the reaction mixture was poured into ice-water, followed by addition of 100 ml of dichloromethane to separate the organic phase. The organic phase was washed subsequently with water, 3% aqueous sodium carbonate solution and water. The organic phase was dried over magnesium sulfate and then concentrated under reduced pressure to obtain 62.4 g (yield: 94.5%) of 4-(3-acetoxypropyl)acetophenone (XVI-29).

55.0 g (0.25 mole) of the (XVI-29) obtained above, 65 g of 10% potassium hydroxide, 20 ml of tetrahydrofuran and 60 ml of methanol were charged, followed by stirring at room temperature for 5 hours. After completion of the reaction, the reaction mixture was concentrated under reduced pressure to distill the tetrahydrofuran and methanol off. The residue was extracted with toluene. The organic phase was further washed with water and then concentrated under reduced pressure to obtain 43.9 g (yield: 98.5%) of 4-(3-hydroxypropyl)acetophenone (XV-29).

Next, 8.54 g (0.048 mole) of the (XV-29) obtained above and 80 ml of dimethylformamide were charged, followed by cooling to 0° to 5° C. After 1.16 g (0.048 mole) of sodium hydride were added thereto, the resulting mixture was maintained at the same temperature for 1 hour and further at 25° C. for 2 hours. Subsequently, 12.1 g (0.05 mole) of 2S-methylbutyl tosylate were added at 20° to 30° C. over 3 hours. The resulting mixture was maintained at the same temperature for 30 minutes and then at 30° to 40° C. for 2 hours.

After completion of the reaction, post-treatment and purification were carried out similarly to in the Preparation Example 26 (starting material), to obtain 8.44 g (yield: 71%) of 4-{3-(2S-methylbutoxy)propyl}acetophenone (VI-29).

$[\alpha]_D^{20} = +3.3°$ (c=1, CHCl$_3$),
$n_D^{20} = 1.5048$.

Next, similarly to in Preparation Example 26 (starting material) 2.48 g (0.01 mole) of the (VI-29) obtained above were added to a mixed solution of 18 ml of 20% aqueous sodium hydroxide solution, 11 g (0.07 mole) of bromine and 20 ml of dioxane, followed by stirring for 24 hours.

Subsequently, similarly to in the Preparation Example 26 (starting material), post-treatment and purification were carried out to obtain 2.25 g (yield: 90.5%) of 4-{3-(2S-methylbutoxy)propyl}-benzoic acid (III-29).

$[\alpha]_D^{20} = +4.6°$ (c=1, CHCl$_3$),
m.p. 49.5° to 51° C.

PREPARATION EXAMPLE 30

Starting material 8.54 g (0.048 mole) of the (XV-29) obtained in Preparation Example 29 (starting material), 10 ml of tetrahydrofuran and 30 ml of dimethylformamide were charged, followed by cooling to 0° to 5° C. After 1.28 g (0.052 mole) of sodium hydride were added thereto, the resulting mixture was maintained at the same temperature for 1 hour and further at 20° C. for 2 hours.

Subsequently, 17.06 g (0.06 mole) of 1R-methylheptyl tosylate were added at 15° C. over 3 hours. The resulting mixture was maintained at the same temperature for 1 hour and then at 30° C. for 1 hour. After completion of the reaction, post-treatment and purification were carried out similarly to in the Preparation Example 26 (starting material), to obtain 6.68 g (yield: 48%) of 4-{3-(1S-methylheptyloxy)propyl}acetophenone (VI-30).

$[\alpha]_D^{20} = +3.1°$ (c=1, CHCl$_3$),
$n_D^{20} = 1.5020$.

Next, 2.9 g (0.01 mole) of the (VI-30) obtained above were added to a mixed solution of 18 ml of 20% aqueous sodium hydroxide solution, 11 g (0.07 mole) of bromine and 30 ml of dioxane, followed by stirring for 24 hours.

Subsequently, similarly to in the Preparation Example 26 (starting material), post-treatment and purification were carried out to obtain 2.66 g (yield: 91%) of 4-{3-(1S-methylheptyloxy)propyl}benzoic acid (III-30).

$[\alpha]_D^{20} = +3.6°$ (c=1, CHCl$_3$),
m.p. 39° to 40° C.

PREPARATION EXAMPLES 31 TO 36

Starting material

Reaction, post-treatment and purification were carried out similarly to in the Preparation Example 30 (starting-material) except that a sulfonate as shown in Table-(v) was used in place of IR-methylheptyl tosylate, to obtain the results as shown in Table-(v).

TABLE (v)

| Preparation Example (starting material) | Alkylating agent (XI) | | Acetophenone (VI) | | Optically active carboxylic acid compound (III) | |
|---|---|---|---|---|---|---|
| | Name | Amount used | Name | Yield and Physical properties | Name | Yield and Physical properties |
| 31 | 2S-butyl-tosylate | 13.7 g (0.06 mmol) | 4-{3-(2R-butoxy)-propyl}-acetophenone (VI-31) | 4.5 g (yield 40%) $[\alpha]_D^{20}$ −5.4° $n_D^{20}$ 1.5058 | 4-{3-(2R-butoxy)propyl}- (III-31) (III-31) | 2.13 g (yield 90%) $[\alpha]_D^{20}$ −6.2° m.p. 63~65° C. |
| 32 | 4S-methyl-hexyl | 13.52 g (0.05 mmol) | 4-{3-(4S-methyl-hexyloxy)propyl}- | 8.36 g (yield 63%) | 4-{3-(4S-methylhexyloxy)- | 2.59 g (yield 93%) |

TABLE (v)-continued

| Preparation Example (starting material) | Alkylating agent (XI) Name | Alkylating agent (XI) Amount used | Acetophenone (VI) Name | Acetophenone (VI) Yield and Physical properties | Optically active carboxylic acid compound (III) Name | Optically active carboxylic acid compound (III) Yield and Physical properties |
|---|---|---|---|---|---|---|
| | tosylate | | benzoic acid (VI-32) | $[\alpha]_D^{20}$ +1.4°<br>$n_D^{20}$ 1.4998 | propyl}-benzoic acid (III-32) | $[\alpha]_D^{20}$ +2.3°<br>$n_D^{20}$ 1.4996 |
| 33 | 2S-fluoro-heptyl tosylate | 17.28 g (0.06 mmol) | 4-{3-(2S-fluoro-heptyloxy)propyl}-aceto-phenone (VI-33) | 6.36 g (yield 45%)<br>$[\alpha]_D^{20}$ −6.9°<br>$n_D^{20}$ 1.4986 | 4-{3-(2S-fluoroheptyloxy)-propyl}-benzoic acid (III-33) | 2.64 g (yield 89%)<br>$[\alpha]_D^{20}$ −7.1°<br>$n_D^{20}$ 1.5046 |
| 34 | 2S-methyl-propyl tosylate | 14.66 g (0.06 mmol) | 4-{3-(4S-methoxy-propoxy)propyl}-acetophenone (VI-34) | 6.25 g (yield 52%)<br>$[\alpha]_D^{20}$ +6.2°<br>$n_D^{20}$ 1.5108 | 4-{3-(2S-methoxypropoxy)-propyl}-benzoic acid (III-34) | 2.37 g (yield 94%)<br>$[\alpha]_D^{20}$ +6.8°<br>m.p. 62~64° C. |
| 35 | 2S-propoxy-propyl tosylate | 16.34 g (0.06 mmol) | 4-{3-(2S-propoxy-propoxy)propyl}-acetophenone (VI-35) | 6.41 g (yield 48%)<br>$[\alpha]_D^{20}$ +4.6°<br>$n_D^{20}$ 1.4999 | 4-{3-(2S-propoxypropoxy)-propyl}-benzoic acid (III-35) | 2.55 g (yield 91%)<br>$[\alpha]_D^{20}$ +5.7°<br>m.p. 43~44° C. |
| 36 | 2S-octyl-oxypropyl tosylate | 20.55 g (0.06 mmol) | 4-{3-(2S-octyl-oxypropoxy)-propyl}aceto-phenone (VI-36) | 6.86 g (yield 41%)<br>$[\alpha]_D^{20}$ +4.0°<br>$n_D^{20}$ 1.4973 | 4-{3-(2S-octyl-oxypropoxy)-propyl}-benzoic acid (III-36) | 3.15 g (yield 90%)<br>$[\alpha]_D^{20}$ +4.9°<br>$n_D^{20}$ 1.5027 |

Optical rotation was each measured under conditions of (c = 1, CHCl₃).

PREPARATION EXAMPLE 37

Starting material

Similarly to in the Preparation Example 26 (starting-material), 84.0 g (0.63 mole) of aluminum chloride and 500 ml of dichloroethane were charged, followed by adding 51.8 g (0.66 mole) of acetyl chloride at 10° to 15° C. over 3 hours. After maintained at the same temperature for 1 hour, 57.6 g (0.3 mole) of 4-phenylbutyl acetate were added thereto at 10° to 20° C. over 3 hours. After maintained at 20° to 25° C. for 3 hours, the reaction mixture was poured into ice-water and dichloroethane was added thereto to effect extraction. Subsequently, similarly to in the Preparation Example 26(starting material), post-treatment and purification were carried out to obtain 56.2 g (yield: 80%) of 4-(4-acetoxybutyl)acetophenole (XVI-37).

58.5 g (0.25 mole) of the (XVI-37) obtained above, 75 g of 20% sodium hydroxide and 150 ml of methanol were charged, followed by stirring at room temperature for 5 hours. Subsequently, similarly to in Preparation Example 26 (starting material) post-treatment and purification were carried out to obtain 40.8 g (yield: 85%) of 4-(4-hydroxybutyl)acetophenone (XV-37).

Next, 9.22 g (0.048 mole) of the (XV-37) obtained above, 60 ml of dimethylformamide and 15 ml of tetrahydrofuran were charged, followed by cooling to 0° to 5° C. After 1.16 g (0.048 mole) of sodium hydride were added thereto, the resulting mixture was maintained at the same temperature for 1 hour and further at 25° to 30° C. for 2 hours. Subsequently, 12.1 g (0.05 mole) of 2S-methylbutyl tosylate were added at 15° to 25° C. over 3 hours. The reaction mixture was maintained at the same temperature for 1 hour and further at 30° to 35° C. for 2 hours.

After completion of the reaction, post-treatment and purification were carried out similarly to in the Preparation Example 26 (starting material), to obtain 8.94 g (yield: 71%) of 4-{4-(2S-methylbutoxy)butyl}acetophenone (VI-37).

$[\alpha]_D^{20}$ = +1.6° (c=1, CHCl₃),
$n_D^{20}$ = 1.5020.

Next, 2.62 g (0.01 mole) of the (VI-37) obtained above were added similarly to in the Preparation Example 26 (starting material), to a solution of 20% aqueous sodium hydroxide solution, 11 g of (0.07 mole) of bromine and 20 ml of dioxane, followed by stirring for 24 hours. Subsequently, similarly to in the Preparation Example 26 (starting material), post-treatment and purification were carried out to obtain 2.43 g (yield: 92%) of 4-{-(2S-methylbutoxy)butyl}benzoic acid (III-37).

$[\alpha]_D^{20}$ = +2.2° (c=1, CHCl₃),
$n_D^{20}$ = 1.5046.

PREPARATION EXAMPLE 38

Starting material 9.22 g (0.048 mole) of the (XV-37) obtained in the Preparation Example 37 (starting material) and 80 ml of dimethylformamide were charged, followed by cooling to 0° to 5° C. After 1.16 g (0.048 mole) of sodium hydride were added thereto and the resulting mixture was maintained at the same temperature for 1 hour, the temperature was raised to room temperature. Subsequently, 16.34 g (0.06 mole) of 2S-propoxypropyl tosylate were added dropwise. The resulting mixture was maintained at room temperature for 1 hour and then at 25° to 30° C. for 3 hours. After completion of the reaction, post-treatment and purification were carried out similarly to in the Preparation Example 26 (starting material), to obtain 8.7 g (yield: 62%) of 4-{4-(2S-propoxypropoxy)butyl}acetophenone (VI-38).

$[\alpha]_D^{20}$ = +4.2° (c=1, CHCl₃),
$n_D^{20}$ = 1.4990.

Next, 2.92 g (0.01 mole) of the (VI-38) obtained above were added at room temperature to a mixed solution of 16 ml of 20% aqueous sodium hydroxide solution, 11 g (0.07 mole) of bromine and 20 ml of dioxane, followed by stirring at room temperature for 20 hours. After completion of the reaction, post-treatment and purification were carried out similarly to in the Preparation Example 26 (starting material), to obtain 2.71 g (yield: 92%) of 4-{4-(2S-propoxypropoxy)butyl} benzoic acid (III-38).

$[\alpha]_D^{20}$ = +4.2° (c=1, CHCl₃),
m.p. 39° to 41° C.

PREPARATION EXAMPLE 39

Starting material

Alkylating reaction, post-treatment and purification were carried out similarly to in Preparation Example 29

(starting material) except that 5.44 g (0.036 mole) of 2S-methylbutyl bromide were used in place of 2S-methylbutyl tosylate to obtain 3.8 (yield: 64%) of 4-{3-(2S-methylbutoxy)propyl}acetophenone (VI-39).

2.48 g (0.01 mole) of the (VI-39) obtained above were subjected to reaction similarly to in the Preparation Example 28 (starting material), to obtain 4-{3-(2S-methylbutoxy)propyl}benzoic acid (III-39). Amount obtained was 2.26 g (yield: 91%).

PREPARATION EXAMPLE 40

Starting material

Into a four-necked flask equipped with a stirrer and a thermometer, 2.96 g (0.04 mole) of 2S-butanol and 15 ml of dimethylformamide were added, followed by cooling to 5° C. or lower. 0.48 g (0.02 mole) of sodium hydride was added, followed by stirring at the same temperature for 1 hour and further at 20° to 25° C. for 2 hours. Subsequently, 4.58 g (0.02 mole) of methyl 4-bromomethylbenzoate were added thereto at 20° to 25° C. over 1 hour, followed by stirring at the same temperature for 2 hours and further at 30° to 35° C. for 2 hours. After completion of the reaction, the reaction mixture was poured into ice-water and extracted with 50 ml of toluene. The organic phase was washed with water and then dried over magnesium sulfate. After the drying agent was filtered off, the solvent was distilled off. The concentrated residue was purified by column chromatography with toluene to obtain 3.20 g (yield: 72%) of methyl 4-(2S-butoxymethyl)benzoate (IX-40).

$[\alpha]_D^{20} = +2.1°$ (c=1, CHCl$_3$),
$n_D^{20} = 1.5032$.

Next, 1.11 g (5 millimole) of the (IX-40) obtained above, 1.5 g (7.5 millimole) of 20% sodium hydroxide and 5 ml of methanol were charged into a four-necked flask, followed by stirring at room temperature for 4 hours. After completion of the reaction, the methanol was distilled off, the resulting mixture was adjusted to weak acidic with 2N-aqueous hydrochloric acid solution and extracted with 20 ml of ethyl acetate. The organic phase was washed with water and then concentrated under reduced pressure. The concentrated residue was purified by chromatography with an eluting solvent of toluene:ethyl acetate=5:1, to obtain 1.01 g (yield: 97%) of 4-(2S-butoxymethyl)benzoic acid (III-40).

$[\alpha]_D^{20} = +6.7°$ (c=1, CHCl$_3$),
m.p. 46° to 48° C.

PREPARATION EXAMPLE 41

Starting material

As the optically active alcohol, 3.52 g (0.04 mole) of 2S-methylbutanol was used in place of 2S-butanol, 3.52 g (0.04 mole) of 2S-methylbutanol, 15 ml of N-methylpyrrolidone and 3 ml of tetrahydrofuran were added, followed by cooling to 5° C. or lower. 0.5 g (0.025 mole) of sodium hydride was added thereto, followed by stirring at the same temperature for 1 hour and further at 20° to 25° for 2 hours. Subsequently, 4.86 g (0.02 mole) of ethyl 4-bromomethylbenzoate were added thereto at 20° C. or lower over 1 hour, followed by stirring at the same temperature for 2 hours and further at 30° to 35° C. for 2 hours. After completion of the reaction, the reaction mixture was poured into ice and extracted with 50 ml of toluene. Subsequently, post treatment and purification were carried out similarly to in the Preparation Example 40 (starting material) to obtain 4.08 g (yield: 76%) of ethyl (4-(2S-methylbutoxymethyl)benzoate (IX-41).

$[\alpha]_D^{20} = +4.3°$ (c=1, CHCl$_3$),
$n_D^{20} = 1.4987$.

Next, 1.34 g (5 millimole) of the (IX-41) obtained above, 2.1 g (7.5 millimole) of 20% potassium hydroxide, 3 ml of methanol and 1 ml of tetrahydrofuran were stirred at 30° C. for 4 hours. After completion of the reaction, the methanol and tetrahydrofuran were distilled off and the resulting mixture was adjusted to weak acidic with 2N-aqueous hydrochloric acid solution. Subsequently, post treatment and purification were carried out similarly to in the Preparation Example 40 (starting material) to obtain 1.07 g (yield: 96.5%) of 4-(2S-methylbutoxymethyl)benzoic acid (III-41).

$[\alpha]_D^{20} = +5.3°$ (c=1, CHCl$_3$),
m.p. 66° to 68° C.

PREPARATION EXAMPLE 42

Starting material

Reaction, post-treatment and purification were carried out similarly to in Preparation Example 40 (starting material) except that 6.41 g (0.02 mole) of p-toluenesulfonic acid 4-hydroxymethylbenzoate were used in place of ethyl 4-bromomethylbenzoate to obtain 3.56 g (yield: 70%) of methyl 4-(2S-methylbutoxy)benzoate (IX-42).

$[\alpha]_D^{20} = +5.5°$ (c=1, CHCl$_3$),
$n_D^{20} = 1.5004$.

Next, 1.27 g (5 millimole) of the (IX-42) obtained above, 2 g (0.01 mole) of 20% sodium hydroxide and 0.1 g of tetrabutylammonium bromide were stirred at 30° C. for 10 hours. After completion of the reaction, the resulting mixture was adjusted to weak acidic with 2N-aqueous hydrochloric acid solution, followed by extraction with 20 ml of ethyl acetate. Subsequently, post treatment and purification were carried out similarly to in the Preparation Example 40 (starting material) to obtain 1.06 g (yield: 95.8%) of 4-(2S-methylbutoxymethyl)benzoic acid (III-42).

$[\alpha]_D^{20} = +5.4°$ (c=1, CHCl$_3$),
m.p. 64° to 66° C.

PREPARATION EXAMPLE 43

Starting material

A solution of 3.32 g (0.02 mole) of methyl 4-hydroxymethylbenzoate and 20 ml of dimethylformamide was cooled to 5° C. and 0.48 g (0.02 mole) of sodium hydride was added, followed by stirring at the same temperature for 1 hour and further at 20° C. for 2 hours. Subsequently, 6.49 g (0.024 mole) of 4S-methylhexyl tosylate were added thereto at 20° to 25° C. over 1 hour, followed by stirring at the same temperature for 2 hours and further at 30° to 35° C. for 3 hours. After completion of the reaction, the reaction mixture was poured into ice-water and extracted with 50 ml of toluene. Subsequently, post treatment and purification were carried out similarly to in the Preparation Example 40 (starting material) to obtain 3.49 g (yield: 66%) of methyl 4-(4S-methylhexyloxymethyl)benzoate (IX-43).

$[\alpha]_D^{20} = +2.1°$ (c=1, CHCl$_3$),
$n_D^{20} = 1.4958$.

Next, 1.32 g (5 millimole) of the (IX-43) obtained above, 3 g (0.015 mole) of 20% sodium hydroxide and 5 ml of methanol were stirred at 20° to 30° C. for 5 hours. After completion of the reaction, the methanol was distilled off, the resulting mixture was adjusted to weak acidic with 2N-aqueous hydrochloric acid solution and extracted with 20 ml of ethyl acetate. The organic phase was washed with water and then concentrated under reduced pressure. The concentrated residue was purified by column chromatography with toluene:ethyl acetate=5:1, to obtain 1.22 g (yield: 97.3%) of 4-(4S-methylhexyloxymethyl)benzoic acid (III-43).

$[\alpha]_D^{20} = +3.8°$ (c=1, CHCl$_3$),
m.p. 44° to 45° C.

PREPARATION EXAMPLES 44 to 49

Starting material

Reaction, post-treatment and purification were carried out similar to in Preparation Example 43 (starting material) except that alkylating agents shown in Table-VI were used in place of 4S-methylhexyl tosylate to obtain the results shown in Table-VI.

PREPARATION EXAMPLES 50 and 51

Starting material

Reaction, post-treatment and purification were carried out similarly to in the Preparation Example 40 (starting material) except that optically active alcohols shown in Table-VII were used in place of 2S-butanol to obtain the results shown in Table-VII.

TABLE (VII)

| Preparation Example (starting material) | Optically active alcohols (XII) | | Optically active benzoate (IX) | | Optically active (III) | |
|---|---|---|---|---|---|---|
| | Name | Amount used | Name | Yield and Physical properties | Name | Yield and Physical property |
| 50 | 2R-octanol | 5.21 g (0.04 mole) | Methyl 4-(2R-octyloxymethyl)-benzoate (IX-51) | 3.56 g (yield 64%) $[\alpha]_D^{20}$ −6.9° (c=1, CHCl$_3$) $n_D^{20}$ 1.4971 | 4-(2R-octyloxymethyl)benzoic acid (III-50) | 1.28 g (yield 96%) $[\alpha]_D^{20}$ −5.5° (c=1, CHCl$_3$) m.p. 41~43° C. |
| 51 | 2R-decanol | 6.33 g (0.04 mole) | Methyl 4-(2R-decyloxymethyl)-benzoate (IX-50) | 3.55 g (yield 58%) $[\alpha]_D^{20}$ −4.1° (c=1, CHCl$_3$) $n_D^{20}$ 1.4946 | 4-(2R-decyloxymethyl)benzoic acid (III-51) | 1.40 g (yield 95.5%) $[\alpha]_D^{20}$ −3.9° (c=1, CHCl$_3$) waxy solid |

Optical rotation was each measured under conditions of (c=1, CHCl$_3$).

PREPARATION EXAMPLE 52

Starting material

Into a four-necked flask equipped with a stirrer and thermometer, 2.96 g (0.04 mole) of 2S-butanol and 15 ml of dimethylformamide were added, followed by cooling to 5° C. or lower. 0.48 g (0.02 mole) of sodium hydride was added, followed by stirring at the same temperature for 1 hour and further at 20° to 25° C. for 2 hours. Subsequently, 6.64 g (0.02 mole) of 3-(4-acetylphenyl)pro-

TABLE (VI)

| Preparation Example (starting material) | Optically active alkylating agent (XI) | | Optically active benzoate (IX) | | Optically active carboxylic acid compound (III) | |
|---|---|---|---|---|---|---|
| | Name | Amount used | Name | Yield and Physical properties | Name | Yield and Physical property |
| 44 | 2S-methylheptyl tosylate | 6.83 g (0.024 mole) | Methyl 4-(2S-methylheptyloxymethyl)-benzoate (IX-44) | 3.40 g (yield 61%) $[\alpha]_D^{20}$ +3.9° (c=1, CHCl$_3$) $n_D^{20}$ 1.5108 | 4-(2S-methylheptyloxymethyl)-benzoic acid (III-44) | 1.27 g (yield 96%) $[\alpha]_D^{20}$ +4.3° (c=1, CHCl$_3$) $n_D^{20}$ 1.5006 |
| 45 | 2S-methylheptyl tosylate | 6.83 g (0.024 mole) | Methyl 4-(5S-methylheptyloxymethyl)-benzoate (IX-45) | 3.56 g (yield 64%) $[\alpha]_D^{20}$ +2.0° (c=1, CHCl$_3$) $n_D^{20}$ 1.4951 | 4-(2S-methylheptyloxymethyl)-benzoic acid (III-45) | 1.28 g (yield 96%) $[\alpha]_D^{20}$ +2.1° (c=1, CHCl$_3$) $n_D^{20}$ 1.4998 |
| 46 | 2S-fluoroheptyl tosylate | 7.21 g (0.025 mole) | Methyl 4-(2S-fluoroheptyloxymethyl)-benzoate (IX-46) | 2.71 g (yield 48%) $[\alpha]_D^{20}$ −5.1° (c=1, CHCl$_3$) $n_D^{20}$ 1.4900 | 4-(2S-fluoroheptyloxymethyl)-benzoic acid (III-46) | 1.28 g (yield 95.5%) $[\alpha]_D^{20}$ −4.3° (c=1, CHCl$_3$) $n_D^{20}$ 1.5030 |
| 47 | 2S-methylpropyl tosylate | 5.86 g (0.025 mole) | Methyl 4-(2S-methoxypropoxymethyl)benzoate (IX-47) | 3.10 g (yield 65%) $[\alpha]_D^{20}$ +6.8° (c=1, CHCl$_3$) $n_D^{20}$ 1.4960 | 4-(2S-methylpropoxymethyl)-benzoic acid (III-47) | 1.08 g (yield 96%) $[\alpha]_D^{20}$ +7.1° (c=1, CHCl$_3$) m.p. 64–66° C. |
| 48 | 2S-propoxypropyl tosylate | 6.54 g (0.024 mole) | Methyl 4-(2S-propoxypropoxymethyl)benzoate (IX-48) | 3.30 g (yield 62%) $[\alpha]_D^{20}$ +6.5° (c=1, CHCl$_3$) $n_D^{20}$ 1.4944 | 4-(2S-propoxypropoxymethyl)-benzoic acid (III-48) | 1.22 g (yield 97%) $[\alpha]_D^{20}$ +6.8° (c=1, CHCl$_3$) m.p. 57–59° C. |
| 49 | 2S-octyloxypropyl tosylate | 8.22 g (0.024 mole) | Methyl 4-(2S-octyloxypropoxymethyl)benzoate (IX-49) | 3.57 g (yield 53%) $[\alpha]_D^{20}$ +4.3° (c=1, CHCl$_3$) $n_D^{20}$ 1.4907 | 4-(2S-octyloxypropoxymethyl)-benzoic acid (III-49) | 1.53 g (yield 95%) $[\alpha]_D^{20}$ +4.9° (c=1, CHCl$_3$) $n_D^{20}$ 1.5024 | pyl tosylate were added thereto at 20° to 25° C. over 1 hour, followed by stirring at the same temperature for 2 2S-butanol to obtain the results as shown in Table-VIII.

TABLE (VIII)

| Preparation Example (starting material) | Optically active alcohols (XII) | | Optically active acetophenone (VI) | | |
|---|---|---|---|---|---|
| | Name | Amount used | Name | Yield | Physical property |
| 54 | 2S-methylbutanol | 3.52 g (0.04 mole) | 4-{3-(2S-methylbutoxy)-propyl}acetophenone (VI-54) | 3.67 g (74%) | $[\alpha]_D^{20}$ +3.1° $n_D^{20}$ 1.5048 |
| 55 | 4S-methylhexanol | 2.91 g (0.025 mole) | 4-{3-(4S-hexyloxy)-propyl}acetophenone (VI-55) | 4.31 g (78%) | $[\alpha]_D^{20}$ +1° $n_D^{20}$ 1.4997 |
| 56 | 2S-fluoroheptyl alcohol | 5.37 g (0.04 mole) | 4-{3-(2S-fluoroheptyloxy)-propyl}acetophenone (VI-56) | 2.06 g (35%) | $[\alpha]_D^{20}$ −6.4° $n_D^{20}$ 1.5004 |
| 57 | 2S-methylpropanol | 2.70 g (0.03 mole) | 4-{3-(2S-methylpropoxy)-propyl}acetophenone (VI-57) | 3.75 g (72%) | $[\alpha]_D^{20}$ +6.2° $n_D^{20}$ 1.5108 |
| 58 | 4S-methylpropanol | 3.54 g (0.03 mole) | 4-{3-(4S-propoxypropoxy)-propyl}acetophenone (VI-58) | 4.34 g (78%) | $[\alpha]_D^{20}$ +4.6° $n_D^{20}$ 1.4999 |
| 59 | 2S-octyloxypropanol | 5.65 g (0.03 mole) | 4-{3-(2S-octyloxypropoxy)-propyl}acetophenone (VI-59) | 4.39 g (63%) | $[\alpha]_D^{20}$ +4.0° $n_D^{20}$ 1.4973 |

Optical rotation was each measured under conditions of (c=1, CHCl₃).

hours and further at 30° to 35° C. for 2 hours. After completion of the reaction, the reaction mixture was poured into ice-water and extracted with 50 ml of toluene, sine organic phase was washed with water and then dried over anhydrous magnesium sulfate, followed by distillation of the solvent. The concentrated residue was purified by column chromatography with toluene to obtain 3.04 g (yield: 65%) of 4-{3-(2S-butoxy)propyl}acetophenone (VI-52).

$[\alpha]_D^{20}$ = +7.5° (c=1, CHCl₃),
$n_D^{20}$ = 1.5123.

PREPARATION EXAMPLE 53

Starting material 5.21 g (0.04 mole) of 2R-octanol, 15 ml of N-methylpyrollidone and 3 ml of tetrahydrofuran were added, followed by cooling to 5° C. or lower. 0.5 g (0.25 mole) of sodium hydride was added, followed by stirring at the same temperature for 1 hour and further at 20° to 25° C. for 2 hours. Subsequently, 6.64 g (0.02 mole) of 3-(4-acetylphenyl)propyl tosylate were added thereto at 20° or lower over 1 hour, followed by stirring at the same temperature for 2 hours and further at 30° to 35° C. for 2 hours. After completion of the reaction, the reaction mixture was poured into ice and extracted with 50 ml of toluene. Subsequently, purification was carried out similarly to in the Preparation Example 52 (starting material) to obtain 3.48 g (yield: 60%) of 4{3-(2R-octyloxy)propyl}acetophenone (VI-53).

$[\alpha]_D^{20}$ = +4.1° (c=1, CHCl₃),
$n_D^{20}$ = 1.5027.

PREPARATION EXAMPLES 54 to 59

Starting material

Reaction, post treatment and purification were carried out similarly to in the Preparation Example 52 (starting-material) except that optically active alcohols (XII) as shown in Table-VIII were used in place of 2S-butanol to obtain the results as shown in Table-VIII.

PREPARATION EXAMPLE 60

Starting material

Into an apparatus similar to in Preparation Example 52 (starting material) were added 4.4 g (0.05 mole) of 2S-methylbutanol and 20 ml of dimethylformamide, and 0.48 g (0.02 mole) of sodium hydride was added at 5° C. or lower, followed by stirring at the same temperature for 1 hour and further at 20° to 25° C. for 2 hours. Subsequently, 4.82 g (0.02 mole) of 3-(4-acetylphenyl)propyl bromide were added thereto at 15° to 20° C., followed by maintaining the temperature at the same temperature for 2 hours and further at 35° to 45° C. for 1 hour. After completion of the reaction, the reaction mixture was poured into ice and extracted with 50 ml of toluene. Subsequently, purification was carried out similarly to in the Preparation Example 52 (starting -material) to obtain 1.84 g (yield: 37%) of 4-{3-(2S-methylbutoxy)propyl}acetophenone (VI-60).

PREPARATION EXAMPLE 61

Starting material 3.52 g (0.04 mole) of 2S-methylbutanol and 15 ml of dimethylformamide were added, and 0.48 g (0.02 mole) of sodium hydride was added thereto at 5° C. or lower, followed by maintaining the temperature at the same temperature for 1 hour and further at 20° to 25° C. for 2 hours. Subsequently, 6.36 g (0.02 mole) of 2-(4-acetylphenyl)ethyl tosylate were added thereto at 20° C. or lower, followed by stirring at the same temperature for 1 hour and further at 20° to 30° C. for 1 hour.

After completion of the reaction, post-treatment and purification were carried out similarly to in the Preparation Example 52 (starting material) to obtain 1.36 g (yield: 29%) of 4-{2-(2S-methylbutoxy)ethyl}acetophenone (VI-61).

$[\alpha]_D^{20}$ = +4.6° (c=1, CHCl₃), $n_D^{20} = 1.5115$.

PREPARATION EXAMPLE 62

Starting material

Reaction, post-treatment and purification were carried out similarly to in the Preparation Example 61 (starting material) except that 5.21 g (0.04 mole) of 2R-octanol were used in place of 2S-methylbutanol to obtain 1.33 g (yield: 24%) of 4-{2-(2R-octyloxy)ethyl}acetophenone (VI-62).

$[\alpha]_D^{20} = -6.3°$ (c=1, CHCl$_3$),
$n_D^{20} = 1.5051$.

PREPARATION EXAMPLE 63

Starting material

Reaction, post-treatment and purification were carried out similarly to in the Preparation Example 61 (starting material) except that 3.54 g (0.03 mole) of 2S-propoxypropanol were used in place of 2S-methylbutanol to obtain 3.86 g (yield: 73%) of 4-{2-(2S-propoxypropoxy)ethyl}acetophenone (VI-63).

$[\alpha]_D^{20} = +4.8°$ (c=1, CHCl$_3$),
$n_D^{20} = 1.5003$.

PREPARATION EXAMPLE 64

Starting material

Reaction, post treatment and purification were carried out similarly to in the Preparation Example 52 (starting material) except that 6.93 g (0.02 mole) of 4-(4-acetylphenyl)butyl tosylate were used in place of 3-(4-acetylphenyl)propyl tosylate to obtain 3.13 g (yield: 63%) of 4-{4-(2S-butoxy)butyl}-acetophenone (VI-64).

$[\alpha]_D^{20} = +9.1°$ (c=1, CHCl$_3$),
$n_D^{20} = 1.5030$.

PREPARATION EXAMPLE 65 to 68

Starting material

Reaction, post treatment and purification were carried out similarly to in the Preparation Example 60 (starting material) except that optically active alcohols (XII) as shown in Table (IX) were used in place of 2S-butanol to obtain the results as shown in Table (IX).

REFERENCE EXAMPLE

Into a four-necked flask equipped with a stirrer and a thermometer, 84.0 g (0.63 mole) of aluminum chloride and 450 ml of dichloromethane were charged, followed by adding 51.8 g (0.66 mole) of acetyl chloride were added at 10° to 15° C. over 2 hours. After maintained at the same temperature for 1 hour, 53.4 g (0.3 mole) of 3-phenylpropyl acetate were added thereto at 10° to 20° C. over 3 hours. After maintained at 25° C. for 4 hours, the reaction mixture was poured into ice-water, followed by addition of 100 ml of dichloromethane to separate the organic phase. The organic phase was washed subsequently with water, 3% aqueous sodium carbonate solution and water. The organic phase was dried over magnesium sulfate and then concentrated under reduced pressure to obtain 62.4 g (yield: 94.5%) of 4-(3-acetoxypropyl)acetophenone.

55.0 g (0.25 mole) of the 4-(3-acetoxypropyl)acetophenone obtained above, 65 g of 10% potassium hydroxide, 20 ml of tetrahybofuran and 60 ml of methanol were charged, followed by stirring at room temperature for 5 hours. After completion of the reaction, the reaction mixture was concentrated under reduced pressure to distill the tetrahydrofuran and methanol off. The residue was extracted with toluene. The organic phase was further washed with water and then concentrated under reduced pressure to obtain 43.9 g (yield: 98.5%) of 4-(3-hydroxypropyl)acetophenone.

Next, (a) to a mixture of 17.8 g (0.01 mole) of the 4-(3-hydroxypropyl)acetophenone obtained above and 50 ml of pyridined, were added 21.7 g (0.105 mole) of toluenesulfonyl chloride at 10° C. or lower over 2 hours. After maintained at the same temperature for 2 hours, the reaction mixture was poured into ice-water, adjusted to weak acidic with 20% aqueous hydrochloric acid solution and extracted with 100 kl of toluene. The organic phase was washed with water, dried over magnesium sulfate and concentrated under reduce pressure to obtain 32.7 g (yield: 98.5%) of 3-(4-acetylphenyl)propyl tosylate.

Further, (b) 17.8 g (0.1 mole) of the 4-(3-hydroxypropyl)acetophenone obtained above were dissolved in 7.91 g of pyridine and 70 ml of toluene, and then 2.71 g (0.01 mole) of phosphorus tribromide were added thereto at 0° to 10° C. After maintained at the same

TABLE (IX)

| Preparation Example (starting material) | Optically active alcohols (XII) | | Optically active acetophenone (VI) | | |
|---|---|---|---|---|---|
| | Name | Amount used | Name | Yield | Physical property |
| 65 | 2S-methyl-butanol | 3.52 g (0.04 mole) | 4-{4-(2S-methylbutoxy)-butyl}aceto-phenone (VI-65) | 3.57 g (68%) | $[\alpha]_D^{20}$ +1.5° $n_D^{20}$ 1.5016 |
| 66 | 2R-octanol | 5.21 g (0.04 mole) | 4-{4-(2R-octyloxy)-butyl}aceto-phenone (VI-66) | 3.71 g (61%) | $[\alpha]_D^{20}$ −2.4° $n_D^{20}$ 1.4992 |
| 67 | 2S-methyl-decanol | 5.16 g (0.03 mole) | 4-{4-(2S-methylundecyloxy)-butyl}aceto-phenone (VI-67) | 3.88 g (56%) | $[\alpha]_D^{20}$ +3.6° $n_D^{20}$ 1.4816 |
| 68 | 2S-propoxy-propanol | 3.54 g (0.03 mole) | 4-{4-(2S-propoxy)butyl}-acetophenone (VI-68) | 4.04 g (69%) | $[\alpha]_D^{20}$ +4.2° $n_D^{20}$ 1.4990 |

Optical rotation was each measured under conditions of (c=1, CHCl$_3$).

temperature for 3 hours, the reaction mixture was poured into ice-water. Subsequently, washing with water, 2% aqueous sodium hydrogen carbonate solution and water was carried out, and after the organic phase was dried over magnesium sulfate, the solvent was distilled off to obtain 21.7 g (yield: 90%) of 3-(4-acetylphenyl)propyl bromide.

Next, 4-phenylbutyl acetate and 2-phenylethyl acetate were used, respectively, in place of 3-phenylpropyl acetate, followed by treatment according to the methods of (a) and (b) to obtain the following compounds:

4-(4-acetylphenyl)butyl tosylate, 4-(4-acetylphenyl)-butyl bromide, 2-(4-acetylphenyl)ethyl tosylate and 2-(4-acetylphenyl)ethyl bromide.

EXAMPLE 1

Into a four-necked flask equipped with a stirrer and a thermometer were charged 1.04 g (5 millimole) of (+)-4-[2-{2(S)-methylbutoxy}ethyl]phenol, 1.67 g (6 millimole) of 4-decyloxybenzoic acid and 30 ml of anhydrous dichloromethane, and 1.22 g (6 millimole) of N,N'-dicyclohexylcarbodiimide and 0.1 g of 4-pyrrolidinopyridine were added thereto, followed by stirring at room temperature for one day.

After completion of the reaction, precipitates formed were filtered off and diluted with 200 ml of toluene. The organic phase was washed with water, 5% aqueous acetic acid solution, 5% aqueous sodium hydrogen carbonate solution and water in this order and then dried over anhydrous magnesium sulfate, followed by concentration under reduced pressure. The obtained residue was purified by silica gel column chromatography (eluent: toluene-ethyl acetate) to obtain 2.10 g (yield: 90%) of (+)-4-[2-{2(S)-methylbutoxy}ethyl]phenyl 4-decyloxybenzoate.

EXAMPLE 2

Into a four-necked flask equipped with a stirrer and a thermometer were charged 1.14 g (5 millimole) of (+)-4-[2-{2(S)-octyloxy}ethyl]phenol and 20 ml of pyridine, and 1.78 g (6 millimole) of 4-decyloxybenzoic chloride were added thereto at 20° to 25° C., followed by stirring at the same temperature and thereafter at 40° C. for 4 hours.

After completion of the reaction, the reaction mixture was poured into 4N hydrochloric acid, followed by extraction with 200 ml of toluene. The organic phase was washed with water, 5% aqueous sodium hydrogen carbonate solution and water in this order and then dried over anhydrous magnesium sulfate, followed by concentration under reduced pressure. The obtained residue was purified by silica gel column chromatography (eluent: toluene-etypl acetate) to obtain 2.33 g (yield: 95.5%) of (+)-4-{2-[2S-octyloxy}ethyl]phenyl 4-decyloxybenzoate.

EXAMPLE 3

Into a four-necked flask were charged 1.18 g (5 millimole) of (+)-4-[2-{2(S)-methylbutoxy}ethyl]benzoic acid, 1.50 g (6 millimole) of 4-decyloxyphenol and 30 ml of dichloromethane, and 1.13 g (5.5 millimole) of N,N'-dicyclohexylcarbodiimide and 0.1 g of 4-pyrrolidinopyridine were added thereto, followed by stirring at 25° to 30° C. for 24 hours. After completion of the reaction, precipitates were filtered off and subsequently, post-treatment and purification were carried out similarly to in Example 1 to obtain 2.08 g (yield: 89%) of (+)-4-decyloxyphenyl 4-[2-{2S-methylbutoxy}ethyl]benzoate.

EXAMPLE 4

Reaction, post-treatment and purification were carried out similarly to in Example 3 except that 1.11 g (5 millimole) of (+)-4-[{2(S)-methylbutoxy}methyl]benzoic acid were used in place of (+)-4-[2-{2(S)-methylbutoxy}ethyl]benzoic acid to obtain 2.0 g (yield: 88%) of (+)-4-decyloxyphenyl 4-[{2(S)-methylbutoxy}methyl]benzoate.

EXAMPLE 5

Into an apparatus similar to in Example 1, were charged 1.04 g (5 millimole) of (+)-4-[2-{2(S)-methylbutoxy}ethyl]phenol, 2.12 g (6 millimole) of 4'-decyloxy-4-biphenylcarboxylic acid and 40 ml of dichloromethane, and then 1.22 g (6 millimole) of N,N'-dicyclohexylcarbodiimide and 0.1 g of 4-pyrrolidinopyridine were added thereto, followed by stirring at room temperature for one day.

Subsequently, post-treatment and purification were carried out similarly to in Example 1 to obtain 2.45 g (yield: 90%) of (+)-4-[2-{2(S)-methylbutoxy}ethyl]phenyl 4'-decyloxy-4-biphenylcarboxylate.

EXAMPLES 6 to 33

Reaction, post-treatment and purification were carried out similarly to in Example 1 or 3 except that a starting-material used is placed with those shown in Table-1, to obtain the results shown in Table 1.

TABLE 1

In the column of phase transition temperature $S_1$ represents smectic phase unidentified

| Example | Optically active compound (III) or (V) R₁ | R'** | n | k | Starting material compound (II) or (IV) R₁ | Y | l | m | R'*** | Optically active esters (I) R₁ | Y | X | R₂ | l | m | n | k | Yield (%) | $[\alpha]_D^{20}$ Angle of rotation (c=1, CHCl₃) | Phase transition temperature (°C.) |
|---|---|---|---|---|---|---|---|---|---|---|---|---|---|---|---|---|---|---|---|---|
| 1 | 2(S)-methyl-butyl | | 2 | 0 | n-C₁₀H₂₁ | —O— | 1 | 1 | —OH | n-C₁₀H₂₁ | —O— | —COO— | 2(S)-methyl-butyl | 1 | 1 | 2 | 0 | 90 | +2.5° | K —35— I, Sc* —−2— S_A, —22— I |
| 2 | 2(S)-octyl | | 2 | 0 | n-C₁₀H₂₁ | —O— | 1 | 1 | —Cl | n-C₁₀H₂₁ | —O— | —COO— | 2(S)-Octyl | 1 | 1 | 2 | 0 | 95.5 | +2.8° | |
| 3 | 2(S) methyl-butyl | —OH | 2 | 0 | n-C₁₀H₂₁ | —O— | 1 | 1 | | n-C₁₀H₂₁ | —O— | —OCO— | 2(S)-methyl-butyl | 1 | 1 | 2 | 0 | 89 | +2° | K —33°— I |
| 4 | 2(S) methyl-butyl | —OH | 1 | 0 | n-C₁₀H₂₁ | —O— | 1 | | | n-C₁₀H₂₁ | —O— | —OCO— | 2(S)-methyl-butyl | 1 | 1 | 1 | 0 | 88 | +2.9° | K —48°— I |
| 5 | 2(S) methyl-butyl | —OH | 2 | 0 | n-C₁₀H₂₁ | —O— | 2 | 1 | —OH | n-C₁₀H₂₁ | —O— | —COO— | 2(S)-methyl-butyl | 2 | 1 | 2 | 0 | 90 | +1.9° | |
| 6 | 2(S)butyl | —OH | 1 | 0 | n-C₈H₁₇ | —COO— | 1 | | | n-C₈H₁₇ | —COO— | —OCO— | 2(S)-butyl | 1 | 1 | 1 | 0 | 87 | −1.5° | |
| 7 | 2(S)methyl-butyl | —OH | 2 | 0 | n-C₁₀H₂₁ | —O— | 2 | 1 | | n-C₁₀H₂₁ | —O— | —OCO— | 2(S)-methyl-butyl | 2 | 1 | 2 | 0 | 90.5 | +2.8° | K —79.5— Sc* —115.5— I, —75— S₁ |
| 8 | 2(S)methyl-butyl | —OH | 2 | 0 | n-C₉H₁₉ | — | 1 | 0 | —OH | n-C₉H₁₉ | — | —COO— | 2(S)-methyl-butyl | 1 | 0 | 0 | 0 | 89 | +2.2° | |
| 9 | 2(R)-butyl | —OH | 2 | 0 | n-C₁₀H₂₁ | —O— | 1 | 1 | —OH | n-C₁₀H₂₁ | —O— | —COO— | 2(R)-butyl | 1 | 1 | 2 | 0 | 88 | +5.3° | |
| 10 | 2(S)-methyl-butyl | —OH | 2 | 0 | n-C₁₆H₃₃ | —O— | 1 | 1 | —OH | n-C₁₀H₂₁ | —O— | —COO— | 2(S)-methyl-butyl | 1 | 1 | 2 | 0 | 86 | +1.5° | |
| 11 | 2(S)-butyl | —OH | 1 | 0 | n-C₁₀H₂₁ | —OCO— | 1 | 1 | | n-C₁₀H₂₁ | —OCO— | —OCO— | 2(S)-butyl | 1 | 1 | 1 | 0 | 90 | +4° | |
| 12 | 2(S)-butyl | —OH | 1 | 0 | n-C₁₀H₂₁ | —O— | 2 | 1 | | n-C₁₀H₂₁ | —O— | —OCO— | 2(S)-butyl | 2 | 1 | 1 | 0 | 88 | | |
| 13 | 4(S)-methyl-hexyl | —OH | 1 | 0 | n-C₁₀H₂₁ | —O— | 1 | 1 | | n-C₁₀H₂₁ | —O— | —OCO— | 4(S)-methyl-hexyl | 1 | 1 | 1 | 0 | 88 | +3.1° | K —35— I |
| 14 | 2(S)methyl-butyl | | 2 | 0 | n-C₆H₁₃ | —O— | 2 | 1 | —OH | n-C₆H₁₃ | —O— | —COO— | 2(R)-butyl | 2 | 1 | 2 | 0 | 87 | | |
| 15 | 2(S)-Fluoro-heptyl | | 2 | 0 | n-C₁₀H₂₁ | —O— | 1 | 1 | —OH | n-C₁₀H₂₁ | —O— | —COO— | 2(S)-fluoro-keptyl | 1 | 1 | 2 | 0 | 89 | | |
| 16 | 4(S)-methyl-hexyl | —OH | 1 | 0 | n-C₁₀H₂₁ | —O— | 1 | 1 | —OH | n-C₁₀H₂₁ | —O— | —OCO— | 4(S)-methyl-hexyl | 1 | 1 | 1 | 0 | 85 | +1° | K —95— Sc* —128— S_A —131— I |
| 17 | 2(S)-butyl | —OH | 1 | 0 | n-C₁₀H₂₁ | —O— | 1 | 1 | | n-C₁₀H₂₁ | —O— | —OCO— | 2(S)-butyl | 1 | 1 | 1 | 0 | 90 | −1.3° | K —65— I |

TABLE 1-continued

In the column of phase transition temperature S₁ represents smectic phase unidentified

| Example | Optically active material compound (III) or (V) | | | | | Starting material compound (II) or (IV) | | | | | Optically active esters (I) | | | | | | | | Yield (%) | $[\alpha]_D^{20}$ Angle of rotation (c = 1, CHCl₃) | Phase transition temperature (°C.) |
|---|---|---|---|---|---|---|---|---|---|---|---|---|---|---|---|---|---|---|---|---|---|
| | R₁ | R'** | n | k | R₁ | Y | l | m | R''** | R₁ | Y | X | R₂ | l | m | n | k | | | |
| 18 | 2(S)-butyl | —OH | 1 | 0 | n-C₈H₁₇ | —O— | 2 | 1 | | n-C₈H₁₇ | —O— | —OCO— | 2(S)-butyl | 2 | 1 | 1 | 0 | 88 | +4.4° | K $\xrightarrow{135}$ Ch $\xrightarrow{147}$ I<br>132<br>Sc* $\xrightarrow{97}$ Sc* $\xrightarrow{135}$ |
| 19 | 4(S)-methyl hexyl | —OH | 1 | 0 | n-C₁₀H₂₁ | —O— | 2 | 1 | | n-C₁₀H₂₁ | —O— | —OCO— | 4(S)-methyl hexyl | 2 | 1 | 1 | 0 | 85 | +1.2° | K———I |
| 20 | 2(S)-propoxypropyl | | 1 | 0 | n-C₁₀H₂₁ | —O— | 1 | 1 | —OH | n-C₁₀H₂₁ | —O— | —COO— | 2(S)-propoxypropyl | 1 | 1 | 1 | 0 | 91 | +4.1° | K———I |
| 21 | 2(S)-propoxypropyl | | 2 | 0 | n-C₈H₁₇ | —O— | 1 | 1 | —OH | n-C₈H₁₇ | —O— | —COO— | 2(S)-propoxypropyl | 1 | 1 | 2 | 0 | 90 | +3.7° | K———I |
| 22 | 2(S)-propoxypropyl | | 2 | 0 | n-C₈H₁₇ | — | 1 | 0 | —OH | n-C₈H₁₇ | — | —COO— | 2(S)-propoxypropyl | 1 | 1 | 2 | 0 | 90 | +3.9° | K———I |
| 23 | 2(S)-propoxypropyl | —OH | 2 | 0 | n-C₈H₁₇ | —O— | 1 | 1 | | i-C₈H₁₇ | —O— | —OCO— | 2(S)-propoxypropyl | 1 | 1 | 2 | 0 | 87 | +3.8° | K———I |
| 24 | 2(S)-propoxypropyl | | 2 | 0 | n-C₁₀H₂₁ | —O— | 2 | 1 | | n-C₁₀H₂₁ | —O— | —COO— | 2(S)-propoxypropyl | 2 | 1 | 2 | 0 | 88 | +2.7° | K———I |
| 25 | 2(S)-propoxypropyl 2(S)-butyl | | 1 | 1 | n-C₁₀H₂₁ | —O— | 1 | 1 | —OH | n-C₁₀H₂₁ | —O— | —COO— | 2(S)-butyl | 1 | 1 | 1 | 1 | 90 | −3.2° | |
| 26 | 2(S)-butyl | —OH | 2 | 1 | n-C₁₀H₂₁ | —O— | 1 | 1 | | n-C₁₀H₂₁ | —O— | —OCO— | 2(S)-butyl | 1 | 1 | 2 | 1 | 85 | −3.4° | K———I |
| 27 | 1(S)-chloro-2(S)methylbutyl | | 1 | 1 | n-C₁₀H₂₁ | —O— | 1 | 1 | —OH | n-C₁₀H₂₁ | —O— | —COO— | 1(S)-chloro-2(S)-methylbutyl | 1 | 1 | 1 | 1 | 89 | −6.7° | K———I |
| 28 | 1(S)-chloro-2(S)methylbutyl | | 2 | 1 | n-C₈H₁₇ | —O— | 1 | 1 | —OH | n-C₈H₁₇ | —O— | —COO— | 1(S)-chloro-2(S)-methylbutyl | 1 | 1 | 2 | 1 | 87 | −6.2° | K———I |
| 29 | 1(S)-chloro-2(S)methylbutyl | | 1 | 1 | n-C₁₀H₂₁ | —O— | 1 | 1 | | n-C₁₀H₂₁ | —O— | —OCO— | 1(S)-chloro-2(S)-methylbutyl | 1 | 1 | 2 | 1 | 84 | −5.9° | K———I |
| 30 | 1(S)-propoxyethyl | | 2 | 1 | n-C₁₀H₂₁ | —O— | 1 | 1 | —OH | n-C₁₀H₂₁ | —O— | —COO— | 1(S)-propoxyethyl | 1 | 1 | 2 | 1 | 88 | +2.9° | K———I |
| 31 | 1(S)-propoxyethyl | —OH | 2 | 1 | n-C₁₀H₂₁ | —O— | 1 | 1 | | n-C₁₀H₂₁ | —O— | —OCO— | 1(S)-propoxyethyl | 1 | 1 | 2 | 1 | 90 | +3.1° | K———I |

TABLE 1-continued

In the column of phase transition temperature S₁ represents smectic phase unidentified

| Example | Optically active material compound (II) or (V) | | | | Starting material compound (II) or (IV) | | | | | | Optically active esters (I) | | | | | | | Yield (%) | $[\alpha]_D^{20}$ Angle of rotation (c = 1, CHCl₃) | Phase transition temperature (°C.) |
|---|---|---|---|---|---|---|---|---|---|---|---|---|---|---|---|---|---|---|---|---|
| | R₁ | R'** | n | k | R₁ | Y | l | m | R'*** | R₁ | Y | X | R₂ | l | m | n | k | | | |
| 32 | 1(S)-propoxyethyl | | 1 | 1 | n-C₁₀H₂₁ | — | 1 | 0 | —OH | n-C₁₀H₂₁ | — | —COO— | 1(S)-propoxyethyl | 1 | 0 | 1 | 1 | 92 | +3.2° | K——I |
| 33 | 1(S)-propoxyethyl | | 2 | 1 | n-C₈H₁₇ | —O— | 2 | 1 | —OH | n-C₈H₁₇ | —O— | —COO— | 1(S)-propoxyethyl | 2 | 1 | 2 | 1 | 85 | +1.8° | |

In the column of R'/—OH represents optically active carboxylic acid compounds (III), and /represents optically active phenols (V).
*In the column of R'*/represents phenols (II), and —OH or —Cl represents carboxylic acid compounds (IV).

As shown in the Examples described above, the compounds of the present invention in which l=2 have a comparatively broad temperature range for the Sc* phase, and by using said compounds as a formulation component of a liquid crystal composition, it is possible to extend the temperature range for the Sc* phase of the liquid crystal composition.

Further, viscosity coefficients of the representative compounds among the compounds obtained in the Examples described above are as shown in Table 1-b. The compounds of the present invention in which l=1 have a small viscosity coefficient and is found to be useful as a component for enhansing the response speed of the liquid crystal composition.

TABLE 1-b

| Example No. | l | Viscosity coefficient* (Pa.sec) |
|---|---|---|
| 1 | 1 | 0.32 |
| 7 | 2 | 0.98 |
| 16 | 1 | 0.40 |
| 19 | 2 | 1.05 |

*Extrapolated value at 20° C.

EXAMPLE 34

A liquid crystal composition was formulated from a known liquid crystal compound (A) having the following phase transition temperature (°C.) and spontaneous polarization value and a liquid crystal compound described in the Example 1:

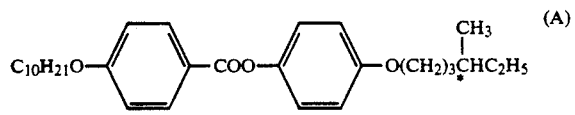

(A)

Phase transition
temperature (°C.) $K \xrightarrow{35} Sc^* \xrightarrow{70.5} S_A \xrightarrow{73.7} I$
$\diagup 30.5$
$S_B$ Spontaneous polarization —OnC/cm²

The formulation of the liquid crystal composition was carried out by weighing a respective compound so as to give a formulation rate of 80 mole % of the known liquid crystal compound and 20 mole % for the liquid crystal compound described in the Example 1 and by melting the resulting mixture by heating in a sample bottle. The phase transition temperature and voluntary polarization value at 20° C. of the thus obtained liquid crystal composition are shown below.

Phase transition
temperature (°C.) $K \xrightarrow{-1}_{B} S \xrightarrow{14} Sc^* \xrightarrow{57}_{A} S \xrightarrow{62} I$ spontaneous polarization + 7.2 nC/cm²

The liquid crystal composition described above exhibits Sc* phase in a lower temperature range than in the known liquid crystal compound (A) and has a broader temperature range of Sc* phase (i.e., a difference between a temperature at which transited from Sc* phase to $S_A$ phase and a temperature at which transited from $S_B$ phase to Sc* phase) and moreover has an increased spontaneous polarization value.

PREPARATION METHOD FOR LIQUID CRYSTAL ELEMENT

On a glass substrate provided with an indium oxide transparent electrode was provided a polyimide type polymer coating film, followed by effecting of rubbing treatment toward a predetermined direction. A liquid crystal cell was assembled by employing glass fibers (diameter: 6 μm) as a spacer so as to maintain the rubbing directions of two pieces of the glass paralleled, and the liquid crystal composition described above was charged thereinto and sealed under vacuum to obtain a liquid crystal element.

The liquid crystal element was combined with a polarizer. When 20 V was applied in electrolysis, change in intensity of transmitted light was observed. The response speed obtained from the change in intensity of transmitted light was found to be 110 sec at 20° C.

Thus, it has been confirmed that a liquid crystal composition having Sc* phase in a lower temperature range and excellent in high speed response can be obtained by adding the liquid crystal compounds of the present invention.

EXAMPLE 35

Into a four-necked flask equipped with a stirrer and a thermometer were charged 1.11 g (5 millimole) of (+)-4-[3-{2(S)-methylbutoxy}propyl]phenol, 1.67 g (6 millimole) of 4-decyloxybenzoic acid and 30 ml of anhydrous dichlomethane, and then 1.22 g (6 millimole) of N,N'-dicyclohexylcarbodiimide and 0.1 g of 4-pyrrolidinopyridine were added thereto, followed by stirring at room temperature for one day. After completion of the reaction, precipitates formed were filtered off and diluted with 200 ml of toluene. The organic phase was washed with water, 5% aqueous acetic acid solution, water, 5% aqueous sodium hydrogen carbonate solution and water in this order and then dried over anhydrous magnesium sulfate, followed by concentration under reduced pressure. The obtained residue was purified by silica gel column chromttography (eluent: toluene-ethyl acetate) to obtain 2.18 g (yield: 90.4%) of (+)-4-[3-{2(S)-methylbutoxy}propyl]phenyl 4-decyloxybenzoate.

EXAMPLE 36

Into a four-necked flask equipped with a stirrer and a thermometer were charged 1.18 g (5 millimole) of (+)-4-[4-{2(S)-methylbutoxy}butyl]phenol and 20 ml of pyridine, and then 1.7 g (6 millimole) of 4-octyloxybenzoic chloride were added thereto at 20° to 25° C., followed by stirring at the same temperature and thereafter at 40° C. for 4 hours.

After completion of the reaction, the reaction mixture was poured into 4N hydrochloric acid, followed by extraction with 200 ml of toluene. The organic phase was washed with water, 5% aqueous sodium hydrogen carbonate solution and water in this order and then dried over anhydrous magnesium sulfate, followed by concentration under reduced pressure. The obtained residue was purified by silica gel column chromatography (eluent: toluene-ethyl acetate) to obtain 2.28 g (yield: 95%) of (+)-4-[4-(2S-methylbutoxy)butyl]phenyl 4-octyloxybenzoate.

EXAMPLE 37

Into an apparatus similar to in Example 1 were charged 1.04 g (5 millimole) of (+)-4-[3-(2(S)-butoxy)- propyl]phenol, 1.95 g (6 millimole) of 4'-octyloxy-4-biphenylcarboxylic acid and 40 ml of chloroform, and into this mixture 1.22 g (6 millimole) of N,N'-dicyclohexylcarbodiimide and 0.1 g of 4-pyrrolidino-pyridine were added, followed by stirring at room temperature for one day.

Subsequently, post-treatment and purification were carried similarly to in Example 1 to obtain 2.30 g (yield: 89%) of (+)-4-[3-(2S-butoxy)propyl]phenyl 4'-octyloxy-biphenylcarboxylate.

EXAMPLE 38

Into a four-necked flask were charged 1.25 g (5 millimole) of (+)-4-[3-{2(S)-methylbutoxy}propyl]benzoic acid, 1.50 g (6 millimole) of 4-decyloxyphenol, 25 ml of anhydrous dichloromethane and 5 ml of tetrahydrofuran, and then 1.13 g (5.5 millimole) of N,N'-dicyclohexylcarbodiimide and 0.05 g of 4-pyrrolidinopyridine were added thereto, followed by stirring at 25° to 35° C. for 20 hours.

After completion of the reaction, precipitates were filtered off and subsequently post-treatment and purification were carried out similarly to in Example 1 to obtain 2.19 g (yield: 91%) of (+)-4-decyloxyphenyl 4-[3-(2(S)-methylbutoxy)propyl]benzoate.

EXAMPLE 39

Into a four-necked flask were charged 1.18 g of (+)-4-[3-(2(S)-butoxy)propyl]benzoic acid, 1.96 g (6 millimole) of 4'-decyloxy-4-biphenol and 40 ml of anhydrous dichloromethane, and then 1.13 g (5.5 milimole) of N,N'-dicyclohexylcarbodiimide and 0.1 g of pyridine were added thereto, followed by stirring at 30° to 35° C. for 20 hours. Subsequently, post-treatment and purification were carried out similarly to in Example 1 to obtain 2.39 g (yield: 88%) of (+)-4'-decyloxybiphenylyl 4-[3-(2(S)-butoxy)-propyl]benzoate.

EXAMPLES 40 TO 86

Reaction and post-treatment were carried out similarly to in Example 35 or 38 except that the starting material compounds used were placed with those as shown in Table 2, to obtain results as shown in Table 2.

TABLE 2

| Example | Starting-material Compound (II) or (IV) | | | | | | Optically active starting-material compound (III) or (V) | | | | Optically active ester derivative (I) | | | | | | Yield (%) | $[\alpha]_D^{20}$ Angle of rotation (c = 1, CHCl$_3$) | Phase transition temperature (°C) |
|---|---|---|---|---|---|---|---|---|---|---|---|---|---|---|---|---|---|---|---|
| | R$_1$ | Y | l | n | k | R$_2$ | Y | l | x | | n | k | R$_2$ | | | | | | |
| 35 | n-C$_{10}$H$_{21}$ | —O— | 1 | 3 | 0 | 2(S)-methyl-bytyl | —O— | 1 | —COO— | | 3 | 0 | 2(S)-methyl-bytyl | | | | 95 | +2° | K —12.5→ S$_1$ —16.5*→ Sc* —29.5*→ I |
| 36 | n-C$_8$H$_{17}$ | —O— | 1 | 4 | 0 | 2(S)-methyl-bytyl | —O— | 1 | —COO— | | 4 | 0 | 2(S)-methyl-bytyl | | | | 95 | +1.1° | K —29→ I; 24.5 S$_A$ |
| 37 | n-C$_8$H$_{17}$ | —O | 2 | 3 | 0 | 2(S)-butyl | —O— | 2 | —COO— | | 3 | 0 | 2(S)-butyl | | | | 89 | +6.0° | K —69→ S$_2$ —69→ S$_1$ —90→ Sc* —137→ S$_A$ —154→ I |
| 38 | n-C$_{10}$H$_{21}$ | —O— | 1 | 3 | 0 | 2(S)-methyl-butyl | —O— | 1 | —OCO— | | 3 | 0 | 2(S)-methyl-butyl | | | | 91 | +1.6° | K —32.7→ I |
| 39 | n-C$_{10}$H$_{21}$ | —O— | 2 | 3 | 0 | 2(S)-butyl | —O— | 2 | —OCO— | | 3 | 0 | 2(S)-butyl | | | | 88 | +5.9° | |
| 40 | n-C$_{10}$H$_{21}$ | —O— | 1 | 4 | 0 | " | —O— | 1 | —COO— | | 4 | 0 | 2(S)-butyl | | | | 90 | +4.8° | K —29→ I; 13 S$_A$ |
| 41 | n-C$_8$H$_{17}$ | —O— | 1 | 3 | 0 | 2(R)-octyl | —O— | 1 | —COO— | | 3 | 0 | 2(R)-octyl | | | | 88.5 | -2.4° | Sc* —24→ I; 0 S$_A$ |
| 42 | n-C$_{10}$H$_{21}$ | —O— | 2 | 3 | 0 | 2(S)-methyl-butyl | —O— | 2 | —COO— | | 3 | 0 | 2(S)-methyl-bytyl | | | | 89 | -1.5° | K —72→ Sc* —120→ S$_A$ —134→ I; 68° S$_1$ |
| 43 | n-C$_8$H$_{17}$ | —O— | 1 | 3 | 0 | 4(S)methylhexyl | —O— | 1 | —COO— | | 3 | 0 | 4(S)-methyl hexyl | | | | 90 | | |
| 44 | n-C$_8$H$_{17}$ | —O— | 1 | 3 | 0 | 2(R)-octyl | —O— | 1 | —OCO— | | 3 | 0 | 2(R)-octyl | | | | 87 | -2° | |
| 45 | n-C$_{10}$H$_{21}$ | —O— | 1 | 5 | 0 | 2(S)-butyl | —O— | 1 | —OCO— | | 5 | 0 | 2(S)-butyl | | | | 86 | +2.5° | |
| 46 | n-C$_9$H$_{19}$ | —*— | 2 | 4 | 0 | " | —*— | 2 | —COO— | | 4 | 0 | " | | | | 88 | +5.1° | |
| 47 | n-C$_8$H$_{17}$ | —COO— | 1 | 4 | 0 | " | —COO— | 1 | —COO— | | 4 | 0 | " | | | | 86 | +4.1° | K —4→ I |
| 48 | n-C$_8$H$_{17}$ | —OCO— | 1 | 3 | 0 | " | —OCO— | 1 | —OCO— | | 3 | 0 | " | | | | 90 | +6.1° | |
| 49 | n-C$_{10}$H$_{21}$ | —O— | 1 | 3 | 0 | 2(S)-fluoroheptyl | —O— | 1 | —COO— | | 3 | 0 | 2(S)-fluoroheptyl | | | | 89 | -4° | |
| 50 | n-C$_6$H$_{18}$ | —O— | 2 | 3 | 0 | 2(S)-butyl | —O— | 2 | —COO— | | 3 | 0 | 2(S)-butyl | | | | 88 | +6° | |
| 51 | n-C$_{16}$H$_{33}$ | —O— | 1 | 3 | 0 | 2(S)-methyl-butyl | —O— | 1 | —COO— | | 3 | 0 | 2(S)-methyl-butyl | | | | 86 | +6° | |

TABLE 2-continued

| | Starting-material Compound (II) or (IV) | | | Optically active starting-material compound (III) or (V) | | | | | | Optically active ester derivative (I) | | | | | | Yield (%) | $[\alpha]_D^{20}$ Angle of rotation (c = 1, CHCl$_3$) | Phase transition temperature (°C.) |
|---|---|---|---|---|---|---|---|---|---|---|---|---|---|---|---|---|---|---|
| Example | R$_1$ | Y | l | n | k | R$_2$ | | R$_1$ | Y | | l | x | | n | k | R$_2$ | | | |
| 52 | n-C$_{10}$H$_{21}$ | —O— | 1 | 3 | 0 | 2(S)-butyl | | n-C$_{10}$H$_{21}$ | —O— | | 1 | —COO— | | 3 | 0 | 2(S)-butyl | 92 | +3.1° | K —22→ Sc* —32→ I ↓7 S$_1$ |
| 53 | n-C$_8$H$_{17}$ | —O— | 2 | 3 | 0 | 2(S)-butyl | | n-C$_8$H$_{17}$ | —O— | | 2 | —OCO— | | 3 | 0 | 2(S)-butyl | 88 | +5.8° | K —94→ Sc* —123→ Ch —135→ I ↓88 S$_1$ |
| 54 | n-C$_8$H$_{17}$ | —O— | 2 | 3 | 0 | 2(R)-octyl | | n-C$_8$H$_{17}$ | —O— | | 2 | —OCO— | | 3 | 0 | 2(R)-octyl | 87 | −3.8° | K —80→ Sc* —115→ Ch —117→ I ↓68 S$_1$ |
| 55 | n-C$_{10}$H$_{21}$ | —O— | 1 | 3 | 0 | 2(S)-butyl | | n-C$_{10}$H$_{21}$ | —O— | | 1 | —OCO— | | 3 | 0 | 2(S)-butyl | 91 | +5.2° | K —37→ I |
| 56 | n-C$_8$H$_{17}$ | —O— | 1 | 3 | 0 | 2(R)-octyl | | n-C$_8$H$_{17}$ | —O— | | 1 | —OCO— | | 3 | 0 | 2(R)-octyl | 93 | −1.7° | K —28→ I |
| 57 | n-C$_{10}$H$_{21}$ | —O— | 1 | 4 | — | 2(S)-methyl-butyl | | n-C$_{10}$H$_{21}$ | —O— | | 1 | —OCO— | | 4 | 0 | 2(S)-methyl-butyl | 90 | +2.0° | K —39→ I ↓17.5 Sc* |
| 58 | n-C$_8$H$_{17}$ | —O— | 1 | 3 | 0 | 2(S)-butyl | | n-C$_8$H$_{17}$ | —O— | | 1 | —COO— | | 3 | 0 | 2(S)-butyl | 93 | +3.9° | K —32→ I ↓5 Sc* —18→ S$_A$ |
| 59 | n-C$_{10}$H$_{21}$ | —*— | 1 | 3 | 0 | " | | n-C$_{10}$H$_{21}$ | —*— | | 1 | —COO— | | 3 | 0 | " | 94 | +3.3° | K —21→ I |
| 60 | n-C$_7$H$_{15}$ | —O— | 1 | 3 | 0 | " | | n-C$_7$H$_{15}$ | —O— | | 1 | —COO— | | 3 | 0 | " | 92 | +4.2° | K —38→ I ↓15 Ch |
| 61 | n-C$_9$H$_{19}$ | —O— | 1 | 3 | 0 | " | | n-C$_9$H$_{19}$ | —O— | | 1 | —COO— | | 3 | 0 | " | 90 | +3.5° | K —31→ I ↓24 Sc* |

TABLE 2-continued

| Example | Starting-material Compound (II) or (IV) | | | | | | Optically active starting-material compound (III) or (V) | | | | Optically active ester derivative (I) | | | | | Yield (%) | $[\alpha]_D^{20}$ Angle of rotation (c = 1, CHCl$_3$) | Phase transition temperature (°C.) |
|---|---|---|---|---|---|---|---|---|---|---|---|---|---|---|---|---|---|---|
| | R$_1$ | Y | l | n | k | R$_2$ | R$_1$ | Y | l | x | n | k | R$_2$ | | | | | |
| 62 | n-C$_{11}$H$_{23}$ | —O— | 1 | 3 | 0 | " | n-C$_{11}$H$_{23}$ | —O— | 1 | —COO— | 3 | 0 | " | 92 | +3.2° | K $\xrightarrow{36}$ Sc* $\xrightarrow{32}$ |
| 63 | n-C$_{12}$H$_{25}$ | —O— | 1 | 3 | 0 | " | n-C$_{12}$H$_{25}$ | —O— | 1 | —COO— | 3 | 0 | " | 90 | +2.8° | K $\xrightarrow{38}$ Sc* $\xrightarrow{35}$ |
| 64 | n-C$_{10}$H$_{21}$ | —O— | 1 | 3 | 0 | 2(R)-octyl | n-C$_{10}$H$_{21}$ | —O— | 1 | —COO— | 3 | 0 | 2(R)-octyl | 88 | −2.2° | K $\xrightarrow{19}$ I, S$_I$ $\xrightarrow{7}$ Sc* |
| 65 | n-C$_8$H$_{17}$ | —O— | 2 | 3 | 0 | " | n-C$_8$H$_{17}$ | —O— | 2 | —COO— | 3 | 0 | " | 86 | −4.1° | K $\xrightarrow{85}$ S$_I$ $\xrightarrow{118}$ Sc* $\xrightarrow{132}$ S$_A$ I |
| 66 | n-C$_8$H$_{17}$ | —O— | 1 | 4 | 0 | " | n-C$_8$H$_{17}$ | —O— | 1 | —OCO— | 4 | 0 | " | 86 | −1.6° | K $\xrightarrow{20}$ I, Ch $\xrightarrow{-4}$ |
| 67 | n-C$_8$H$_{17}$ | —O— | 2 | 4 | 0 | " | n-C$_8$H$_{17}$ | —O— | 2 | —OCO— | 4 | 0 | " | 84 | −3.7° | K $\xrightarrow{55}$ Sc* $\xrightarrow{100}$ Ch $\xrightarrow{110}$ I, S$_I$ $\xrightarrow{50}$ |
| 68 | n-C$_8$H$_{17}$ | —O— | 1 | 4 | 0 | " | n-C$_8$H$_{17}$ | —O— | 1 | —COO— | 4 | 0 | " | 87 | −2.5° | K $\xrightarrow{23}$ I, S$_A$ $\xrightarrow{8}$ |
| 69 | n-C$_8$H$_{17}$ | —O— | 2 | 4 | 0 | " | n-C$_8$H$_{17}$ | —O— | 2 | —COO— | 4 | 0 | " | 86 | −3.5° | K $\xrightarrow{50}$ Sc* $\xrightarrow{89}$ S$_A$ $\xrightarrow{132}$ I, S$_I$ $\xrightarrow{56}$ |
| 70 | n-C$_{10}$H$_{21}$ | —O— | 1 | 3 | 0 | 2(R)-fluoropropyl | n-C$_{10}$H$_{21}$ | —O— | 1 | —COO— | 3 | 0 | 2(R)-fluoropropyl | 87 | −0.7° | K $\xrightarrow{33}$ I, Sc* $\xrightarrow{8}$ S$_A$ $\xrightarrow{30}$ |

TABLE 2-continued

| Example | Starting-material Compound (II) or (IV) | | | | Optically active starting-material compound (III) or (V) | | | | | Optically active ester derivative (I) | | | | | Yield (%) | $[\alpha]_D^{20}$ Angle of rotation (c = 1, CHCl$_3$) | Phase transition temperature (°C.) |
|---|---|---|---|---|---|---|---|---|---|---|---|---|---|---|---|---|---|
| | $R_1$ | Y | l | n | k | $R_2$ | $R_1$ | Y | l | x | n | k | $R_2$ | | | |
| 71 | n-C$_8$H$_{17}$ | —O— | 1 | 3 | 0 | 2(S)-propoxy | n-C$_8$H$_{17}$ | —O— | 1 | —COO— | 3 | 0 | 2(S)-propoxy-propyl | 92 | +3.2° | K —17— I / Sc* —15— S$_A$ —10— |
| 72 | n-C$_{10}$H$_{21}$ | —O— | 1 | 3 | 0 | 2(S)-propoxy | n-C$_{10}$H$_{21}$ | —O— | 1 | —COO— | 3 | 0 | 2(S)-propoxy-propyl | 92 | +3.0° | K —15— S$_A$ —18— I / Sc* —8— |
| 73 | n-C$_{10}$H$_{21}$ | —O— | 1 | 4 | 0 | 2(S)-propoxy | n-C$_{10}$H$_{21}$ | —O— | 1 | —COO— | 4 | 0 | 2(S)-propoxy-propyl | 89 | +2.9° | |
| 74 | n-C$_{10}$H$_{21}$ | —O— | 1 | 3 | 0 | 2(S)-propoxy | n-C$_{10}$H$_{21}$ | —O— | 1 | —OCO— | 3 | 0 | 2(S)-propoxy-propyl | 90 | +3.3° | |
| 75 | n-C$_{10}$H$_{21}$ | —O— | 1 | 3 | 1 | 2(S)-butyl | n-C$_{10}$H$_{21}$ | —O— | 3 | —COO— | 3 | 1 | 2(S)-butyl | 87 | −2.6° | K —22— I / S$_I$ —15— Sc* —10— S$_A$ |
| 76 | n-C$_8$H$_{17}$ | —O— | 2 | 3 | 1 | " | n-C$_8$H$_{17}$ | —O— | 2 | —COO— | 3 | 1 | " | 85 | −1.9° | K —76— S$_1$ —78— Sc* —104— S$_A$ —139— I |
| 77 | n-C$_{10}$H$_{21}$ | —O— | 1 | 3 | 1 | " | n-C$_{10}$H$_{21}$ | —O— | 1 | —OCO— | 3 | 1 | " | 86 | −3.0° | K —— I |
| 78 | n-C$_8$H$_{17}$ | —O— | 1 | 4 | 1 | " | n-C$_8$H$_{17}$ | —O— | 1 | —OCO— | 4 | 1 | " | 85 | −2.2° | K —— I |
| 79 | n-C$_8$H$_{17}$ | —O— | 2 | 3 | 1 | " | n-C$_8$H$_{17}$ | —O— | 2 | —OCO— | 3 | 1 | " | 83 | −1.7° | |
| 80 | n-C$_8$H$_{17}$ | —O— | 1 | 3 | 1 | 1(S)-chloro-2(S)-methyl-butyl | n-C$_8$H$_{17}$ | —O— | 1 | —COO— | 3 | 1 | 1(S)-chloro-2(S)-methyl-butyl | 82 | −5.3° | —5— I |
| 81 | n-C$_{10}$H$_{21}$ | —O— | 1 | 3 | 1 | 1(S)-chloro-2(S)-methyl-butyl | n-C$_{10}$H$_{21}$ | —O— | 1 | —COO— | 3 | 1 | 1(S)-chloro-2(S)-methyl-butyl | 85 | −4.2° | K —12— I |
| 82 | n-C$_{10}$H$_{21}$ | —O— | 1 | 4 | 1 | 1(S)-chloro-2(S)-methyl-butyl | n-C$_{10}$H$_{21}$ | —O— | 1 | —COO— | 4 | 1 | 1(S)-chloro-2(S)-methyl-butyl | 83 | −3.9° | K —— I |
| 83 | n-C$_8$H$_{17}$ | —O— | 2 | 3 | 1 | (S)-chloro-2(S)-methyl-butyl | n-C$_8$H$_{17}$ | —O— | 2 | —COO— | 3 | 1 | 1(S)-chloro-2(S)-methyl-butyl | 81 | −2.2° | |

TABLE 2-continued

| | Starting-material Compound (II) or (IV) | | Optically active starting-material compound (III) or (V) | | | | | | Optically active ester derivative (I) | | | | | Yield (%) | $[\alpha]_D^{20}$ Angle of rotation (c = 1, CHCl$_3$) | Phase transition temperature (°C.) |
|---|---|---|---|---|---|---|---|---|---|---|---|---|---|---|---|---|
| Example | R$_1$ | Y | R$_1$ | n | k | R$_2$ | | l | x | Y | n | k | R$_2$ | | | |
| 84 | n-C$_{10}$H$_{21}$ | —O— | n-C$_{10}$H$_{21}$ | 3 | 1 | 1(S)-chloro-2(S)-methyl-butyl | | 1 | —OCO— | —O— | 3 | 1 | 1(S)-chloro-2(S)-methyl-butyl | 85 | −4.6° | K——I |
| 85 | n-C$_{10}$H$_{21}$ | —O— | n-C$_{10}$H$_{21}$ | 3 | 1 | 1(S)-propoxy-ethyl | | 1 | —COO— | —O— | 3 | 1 | 1(S)-propoxy-ethyl | 88 | +2.3° | K——I |
| 86 | n-C$_{10}$H$_{20}$ | —O— | n-C$_{10}$H$_{21}$ | 3 | 1 | 1(S)-propoxy-ethyl | | 1 | —OCO— | —O— | 3 | 1 | 1(S)-propoxy-ethyl | 90 | +2.5° | K——I |

As shown in the Examples 35 to 86 described above, the compounds of the present invention in which l=2 have a comparatively wide temperature range for the Sc* phase, and by using said compounds as a formulation component of a liquid crystal composition, it is possible to extend the temperature range for the Sc* phase.

Further, viscosity coefficients of the representative compounds among the compounds obtained in the Examples 35 to 86 described above are as shown in Table 2-b. As is apparent from this Table, the compounds of the present invention in which l=1 have a small viscosity coefficient and is found to be useful as a component for enhancing the response speed of the liquid crystal.

TABLE 2-b

| Example No. | l | Viscosity coefficient* (Pa.sec) |
|---|---|---|
| 24 | 1 | 0.39 |
| 27 | 1 | 0.30 |
| 29 | 1 | 0.47 |
| 30 | 1 | 0.32 |
| 31 | 2 | 0.95 |

*Extrapolated value at 20° C.

PREPARATION METHOD OF LIQUID CRYSTAL ELEMENT

On a glass substrate provided with an indium oxide transparent electrode was provided a polyimide type polymer coating film, followed by rubbing treatment in a predetermined direction. A liquid crystal cell was assembled by employing glass fibers (diameter: 6 μm) as a spacer so as to maintain the rubbing directions of two pieces of the glass paralleled, and the liquid crystal composition described above was charged thereinto and sealed under vacuum to obtain a liquid crystal element.

This liquid crystal element was combined with a polarizer. When 20 V was applied in electrolysis, changes in intensity of transmitted light was observed. The response time was obtained from the changes in intensity of transmitted light at this time, the results of which are as shown in Table-3.

Thus, it has been confirmed that a liquid crystal composition having a phase transition temperature in a lower temperature range and excellent in high speed response can be obtained by adding the liquid crystal compounds of the present invention.

TABLE 3

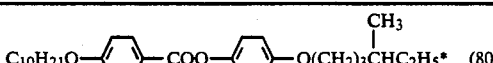

*Known compound (A)

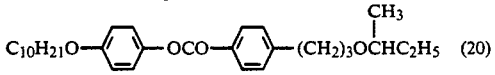

spontaneous polarization −0 nC/cm²

EXAMPLES 87 AND 88

Liquid crystal compositions as shown in Table-3 were formulated by employing the liquid crystal compounds in the Examples 55 and 63. The formulation of the liquid crystal compositions were carried out by weighing a predetermined amount of predetermined compound and mixing the compounds under heat-melting in a sample bottle. The phase transition temperature (°C.) and spontaneous polarization value at 20° C. of the thus obtained liquid crystal compositions are shown in Table-3.

We claim:

1. An optically active phenol represented by the formula (V):

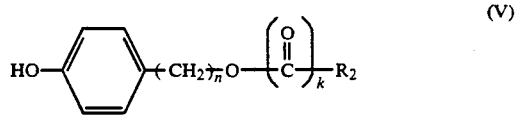

wherein $R_2$ represents an optically active alkyl or alkoxyalkyl group having 3 to 15 carbon atoms optionally substituted by halogen atoms; k represents a number of 0 or 1; n represents a number of 1 to 6.

2. An optically active phenol according to claim 1, wherein k is 0.

3. An optically active phenol according to claim 1, wherein k is 1.

* * * * *